United States Patent
Fujita et al.

(10) Patent No.: US 8,236,867 B2
(45) Date of Patent: Aug. 7, 2012

(54) POLYMER COMPLEX HAVING CHANNELS AND METHOD FOR CHEMICALLY MODIFYING INNER SURFACES OF CHANNELS OF POLYMER COMPLEX

(75) Inventors: Makoto Fujita, Chiba (JP); Masaki Kawano, Chiba (JP); Takehide Kawamichi, Tokyo-to (JP); Kiyoshi Nakanishi, Susono (JP); Takahiro Kojima, Tokyo-to (JP); Tomoki Kodama, Toyota (JP)

(73) Assignees: The University of Tokyo, Tokyo-to (JP); Toyota Jidosha Kabushiki Kaisha, Aichi-ken (JP)

(*) Notice: Subject to any disclaimer, the term of this patent is extended or adjusted under 35 U.S.C. 154(b) by 151 days.

(21) Appl. No.: 12/449,925

(22) PCT Filed: Mar. 7, 2008

(86) PCT No.: PCT/JP2008/054697
§ 371 (c)(1),
(2), (4) Date: Sep. 10, 2010

(87) PCT Pub. No.: WO2008/111665
PCT Pub. Date: Sep. 18, 2008

(65) Prior Publication Data
US 2010/0324249 A1 Dec. 23, 2010

(30) Foreign Application Priority Data
Mar. 7, 2007 (JP) ................. 2007-057601

(51) Int. Cl.
*C08G 79/00* (2006.01)
*C07C 249/02* (2006.01)
*C08L 101/02* (2006.01)
*C08K 5/3492* (2006.01)

(52) U.S. Cl. ........ 521/153; 521/123; 521/125; 521/156; 525/326.7; 524/612; 544/181

(58) Field of Classification Search ............ 521/123, 521/125, 153, 156; 544/181; 524/612; 525/326.7
See application file for complete search history.

(56) References Cited

U.S. PATENT DOCUMENTS
5,019,263 A 5/1991 Haag et al.
(Continued)

FOREIGN PATENT DOCUMENTS
JP 7-185275 7/1995
(Continued)

OTHER PUBLICATIONS

O. Ohmori et al., "Crystal-to-Crystal Guest Exchange of Large Organic Molecules within a 3D Coordination Network," Journal of the American Chemical Society, vol. 126, No. 50, pp. 16292-16293 (2004).

(Continued)

*Primary Examiner* — Irina S Zemel
(74) *Attorney, Agent, or Firm* — Finnegan, Henderson, Farabow, Garrett & Dunner, LLP

(57) ABSTRACT

An embodiment of the present invention includes a method for chemically modifying inner surfaces of channels capable of further regulating characteristics of the internal environment of channels, by forming a polymer complex having a specific channel group B, the channel environmental characteristics of which are regulated by substituents A, followed by utilizing the channels of the channel group B as a reaction field to convert the substituent A to a different substituent. The method may comprise including a guest molecule in the channel of the channel group B in which the substituents A are arranged; and reacting the guest molecule with the substituent A in the channel to convert the substituent A to a substituent A', and to arrange the substituent A' regularly directing to the inside of the channel of the channel group B or any channel of other channel groups.

20 Claims, 21 Drawing Sheets
(20 of 21 Drawing Sheet(s) Filed in Color)

U.S. PATENT DOCUMENTS

2011/0098414 A1 * 4/2011 Fujita et al. ............... 525/326.7

FOREIGN PATENT DOCUMENTS

| JP | 8-318141 | 12/1996 |
|----|----------|---------|
| JP | 2001-232156 | 8/2001 |
| JP | 2003-55271 | 2/2003 |
| JP | 2003-210950 | 7/2003 |
| JP | 2005-255545 | 9/2005 |
| JP | 2006-188560 | 7/2006 |

OTHER PUBLICATIONS

M. Fujita et al., U.S. Appl. No. 12/224,805, filed Sep. 5, 2008.

* cited by examiner (2A)

(2B)

(3A)

(3B)

(4 A)

(4 B)

C        D$_4$ (a)

C            D₁'

(b)

(8A)

(8B)

(9 A)

(9 B)

Orthorhombic *Pbca*
$a\,/\,\text{Å} = 28.073(3)$, $b\,/\,\text{Å} = 13.8598(14)$
$c\,/\,\text{Å} = 44.387(4)$, $V\,/\,\text{Å}^3 = 17270(3)$
$R_1 = 0.093$, $T\,/\,K = 80$
Size / mm = 0.15 X 0.15 X 0.10

Orthorhombic *Pbca*
$a / Å = 28.102(5)$, $b / Å = 13.700(2)$
$c / Å = 45.448(8)$, $V / Å^3 = 17497(5)$
$R_1 = 0.090$, $T / K = 80$
Size / mm = 0.08 X 0.08 X 0.08

POLYMER COMPLEX HAVING CHANNELS AND METHOD FOR CHEMICALLY MODIFYING INNER SURFACES OF CHANNELS OF POLYMER COMPLEX

CROSS-REFERENCE TO RELATED APPLICATIONS

This application is a national phase application of International Application No. PCT/JP2008/054697, filed Mar. 7, 2008, and claims the priority of Japanese Application No. 2007-057601, filed Mar. 7, 2007, the contents of both of which are incorporated herein by reference.

TECHNICAL FIELD

The present invention relates to a polymer complex provided with two or more kinds of channel groups each composed of channels identical with one another and having inherent affinity for guest molecules, and a method for chemically modifying inner surfaces of channels of at least one kind of channel group in the polymer complex.

BACKGROUND ART

By allowing a mixture containing many kinds of organic compounds to be passed through, or in contact with, a material having a pore structure which takes a guest compound in, a specific organic compound can be selectively taken out. As such material, an organic metal complex having organic ligands complexed with a transition metal, or zeolite or the like, is known and used in many applications as a selective reversible adsorbent, a catalyst carrier, etc.

SUMMARY OF INVENTION

Technical Problem

However, the environments of channels (internal environments of channels) contained in a structure of zeolite or the like are uniform, and relatively large channels different in environment hardly coexist in a single zeolite material. Accordingly, two or more kinds of channels capable of selective incorporation of compounds having a relatively large molecular size, such as organic compounds, conventionally hardly coexist in a single material having an action of incorporating guest compounds.

In view of the circumstances described above, some of the present inventors have developed a polymer complex having an aromatic compound having two or more coordinating sites as a ligand, a metal ion as a central metal, and an uncoordinating aromatic compound, wherein the polymer complex has a three-dimensional lattice-like structure containing a stack structure comprising the uncoordinating aromatic compound intercalated between the aromatic compound ligands in a three-dimensional coordination network formed by coordinating the aromatic compound ligands to the central metal ion, and the three-dimensional lattice-like structure is provided with two or more kinds of channel groups each composed of channels identical with one another and having inherent affinity for guest molecules, and they have already filed a patent application therefor (Japanese Patent Application No. 2004-382152).

The present inventors have further improved the polymer complex for which the patent application (Japanese Patent Application No. 2004-382152) has already been filed, and developed a polymer complex having a specific channel group B modified among the two or more kinds of channel groups having inherent affinity for specific guest molecules by introducing a specific substituent A into an aromatic ring of the uncoordinating aromatic compound to regulate characteristics of the channel environment of the channel group B. They have already filed a patent application therefor (Japanese Patent Application No. 2006-63416).

The present invention has further been developed through the history of development described above. The object of the present invention is to provide a method for chemically modifying the inner surfaces of channels capable of further regulating characteristics of the internal environment of channels, by forming a polymer complex having a specific channel group B, the channel environmental characteristics of which are regulated by a specific substituent A, followed by utilizing the channels of the channel group B as a reaction field to convert the substituent A to a different substituent. Also, the present invention is to provide a polymer complex having highly specific channel environmental characteristics obtained by the chemical modification method.

Solution to Problem

A method for chemically modifying inner surfaces of channels of a polymer complex according to the present invention is a method for chemically modifying inner surfaces of channels of at least one kind of channel group in a polymer complex provided with two or more kinds of channel groups each composed of channels identical with one another and having inherent affinity for a guest molecule, wherein the polymer complex comprises an aromatic compound having two or more coordinating sites as a ligand, a metal ion as a central metal, and an uncoordinating aromatic compound, has a three-dimensional lattice-like structure containing a stack structure comprising the uncoordinating aromatic compound intercalated between aromatic compound ligands in a three-dimensional coordination network formed by coordinating the aromatic compound ligands to the central metal ion, and is provided with two or more kinds of the channel groups in the three-dimensional coordination network, and the uncoordinating aromatic compound has a specific substituent A at a specific position on the aromatic ring thereof, and is arranged regularly such that the substituent A is directed to the inside of a specific channel group B out of the two or more kinds of channel groups;

comprising the steps of: including the guest molecule in the channel of the channel group B in which the substituent A is arranged; and reacting the guest molecule with the substituent A in the channel to convert the substituent A to a substituent A', and to arrange the substituent A' regularly directing to the inside of the channel of the channel group B or any channel of other channel groups.

The chemical modification method of the present invention is a method which chemically modifies the inner surfaces of channels after forming the above polymer complex, in which the two or more kinds of channel groups are formed. The channels of the polymer complex have inherent affinity for guest molecules, and thus selectively incorporate a specific guest molecule. Accordingly, the guest molecule is incorporated into a channel of the channel group B, and a chemical reaction of the substituent A oriented toward the inside of the channel group B with the guest molecule is caused, thereby, the channel can be chemically modified.

In this way, by arranging the substituents A' regularly such that each substituent A' is directed to the inside of a channel group using the chemical modification method after forming a polymer complex, a polymer complex having channels, the affinity of which is changed by the substituents A', wherein the substituent A' cannot be introduced to the uncoordinating aromatic compound constituting the polymer complex due to the electronic state of the uncoordinating aromatic compound, the steric component of the substituent or the like when forming the polymer complex, can be obtained. In addition, the inside of each channel is a specific reaction field due to the effect of minute space of the channel. Therefore, in the channel, a chemical reaction which is not caused in a normal environment outside of the channels can proceed and a certain kind of intermediate product unstable in a normal environment can be produced as a stable final product.

As described above, according to the present invention, the inner surfaces of channels having inherent affinity for specific guest molecules can be more specific by a chemical modification. Therefore, the present invention can provide a polymer complex being capable of more highly selective incorporation, release and/or transportation of guest molecules, and having the channels capable of being utilized as a chemical reaction field which causes a specific chemical reaction.

In the polymer complex, the embodiments of the three-dimensional coordination network include a complexed three-dimensional coordination network comprising two or more independent three-dimensional coordination networks complexed with one another. This complexed three-dimensional coordination network includes, for example, an interpenetrated structure wherein independent three-dimensional structures are intricately intertwined with one another.

Two channel groups selected arbitrarily from the two or more kinds of channel groups are made different from each other in respect of the affinity, for guest molecules, of channels constituting each of the channel groups by making them different in at least one factor selected from the size of a channel, the shape of a channel and the atmosphere in a channel in comparison therebetween.

When the stack structure is formed by sufficiently stacking aromatic compound ligands and uncoordinating aromatic compounds wherein the three-dimensional coordination network is formed with a sufficient three-dimensional extension, the resulting channels are in a long and thin form.

Specific examples of the aromatic compound ligand include aromatic compounds represented by the following formula (1):

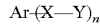   Formula 1 wherein Ar is a structure having an aromatic ring, X is a divalent organic group or a single bond through which Ar and Y are directly bound to each other, Y is a coordinating atom or a coordinating atom-containing atomic group, n is a number of 3 to 6, and a plurality of Xs contained in one molecule may be different from one another, and a plurality of Ys may be different from one another.

Specific examples of the uncoordinating aromatic compound include condensed polycyclic aromatic compounds.

More specifically, the polymer complex is a complex wherein the aromatic compound represented by the formula (1) is tris(4-pyridyl) triazine, and the condensed polycyclic aromatic compound is at least one member selected from triphenylene and perylene.

The substituent A is not particularly limited; for example, the substituent A is preferably one that can exhibit an intramolecular interaction higher than van der Waals' force in the polymer complex.

In the stack structure in the three-dimensional coordination network, by selecting the uncoordinating aromatic compound, a substituent to be introduced into the uncoordinating aromatic compound and the aromatic compound ligand so that the HOMO (highest occupied molecular orbital) of the uncoordinating aromatic compound and the LUMO (lowest unoccupied molecular orbital) of the aromatic compound ligand overlap in the number and position of nodal planes, in electron distribution, and in the orbital shape with respect to energy level and the stack structure to be stabilized, the stack structure to be formed in the polymer complex can be predicted and efficient molecular design is feasible.

By way of example, the substituent A is at least one functional group selected from —W—OH, —W—NH$_2$, —W—NO$_2$, —W—CH$_3$, —W—OCOCH$_3$, —W—CHO, an alkyl ether chain, an alkylthio ether chain, an alkylene glycol chain, and a peptide chain, wherein W represents a divalent organic group or a single bond.

When the uncoordinating aromatic compound has at least one —NH$_2$ as the substituent A, the —NH$_2$ can be converted to —N=Q1, Q1 representing a divalent organic group. Specifically, the guest molecule is an aldehyde compound, and incorporation of the aldehyde compound by a channel of the channel group B can cause a dehydration reaction of —NH$_2$ being the substituent A with the aldehyde compound to convert —NH$_2$ to —N=Q1, Q1 representing a divalent organic group.

Also, when the uncoordinating aromatic compound has at least one —NH$_2$ as the substituent A, the —NH$_2$ can be converted to —NHC(=O)-Q2, Q2 representing a monovalent organic group. Specifically, the guest molecule is acid anhydride or isocyanato, and incorporation of the acid anhydride or the isocyanato by a channel of the channel group B can cause a reaction of —NH$_2$ being the substituent A with the acid anhydride or the isocyanato to convert —NH$_2$ to —NHC(=O)-Q2, Q2 representing a monovalent organic group.

Further, when at least one of the substituents A is —CHO and the guest molecule is an amino compound, incorporation of the amino compound by a channel of the channel group B can cause a dehydration reaction of the —CHO with the amino compound to convert —CHO to —CHN-Q3, Q3 representing a monovalent organic compound.

That is, according to the chemical modification method of the present invention, the inside of the polymer complex can be chemically modified by a substituent which is highly unstable and exists as a short-lived intermediate in a normal environment, and by a substituent which forms a complex with one of metal species to disturb construction of the polymer complex when the substituent is preliminarily introduced to the uncoordinating aromatic compound before constructing the polymer complex.

Particularly, according to the present invention, in the polymer complex, at least one of the substituents A can be converted to -Q4-COOH, Q4 representing a divalent organic group. That is, the inside of channels of the polymer complex can be chemically modified by a substituent containing a carboxyl group. As described above, by orienting an anionic functional group in the channel, a cation such as a metal ion can beheld and applications of the polymer complex such as catalyst materials and electrolyte materials can be expected.

The present invention, for example, can provide a polymer complex comprising an aromatic compound having two or more coordinating sites as a ligand, a metal ion as a central metal, and an uncoordinating aromatic compound, wherein the polymer complex has a three-dimensional lattice-like structure containing a stack structure comprising the uncoordinating aromatic compound intercalated between aromatic compound ligands in a three-dimensional coordination network formed by coordinating the aromatic compound ligands to the central metal ion, and is provided with two or more kinds of channel groups each composed of channels identical with one another and having inherent affinity for guest molecules, and the uncoordinating aromatic compound has a group A'i represented by —N═Q1, Q1 representing a divalent organic group, at a specific position on the aromatic ring thereof, and is arranged regularly such that the group A'i is directed to the inside of a specific channel group B' out of the two or more kinds of channel groups.

Alternatively, the present invention can provide a polymer complex comprising an aromatic compound having two or more coordinating sites as a ligand, a metal ion as a central metal, and an uncoordinating aromatic compound, wherein the polymer complex has a three-dimensional lattice-like structure containing a stack structure comprising the uncoordinating aromatic compound intercalated between aromatic compound ligands in a three-dimensional coordination network formed by coordinating the aromatic compound ligands to the central metal ion, and is provided with two or more kinds of channel groups each composed of channels identical with one another and having inherent affinity for guest molecules, and the uncoordinating aromatic compound has a group A'a represented by —NHC(═O)-Q2, Q2 representing a monovalent organic group, at a specific position on the aromatic ring thereof, and is arranged regularly such that the group A'a is directed to the inside of a specific channel group B' out of the two or more kinds of channel groups.

Alternatively, the present invention can provide a polymer complex comprising an aromatic compound having two or more coordinating sites as a ligand, a metal ion as a central metal, and an uncoordinating aromatic compound, wherein the polymer complex has a three-dimensional lattice-like structure containing a stack structure comprising the uncoordinating aromatic compound intercalated between aromatic compound ligands in a three-dimensional coordination network formed by coordinating the aromatic compound ligands to the central metal ion, and is provided with two or more kinds of channel groups each composed of channels identical with one another and having inherent affinity for guest molecules, and the uncoordinating aromatic compound has a group A'im represented by —CHN-Q3, Q3 representing a monovalent organic group, at a specific position on the aromatic ring thereof, and is arranged regularly such that the group A'im is directed to the inside of a specific channel group B' out of the two or more kinds of channel groups.

Alternatively, the present invention can provide a polymer complex comprising an aromatic compound having two or more coordinating sites as a ligand, a metal ion as a central metal, and an uncoordinating aromatic compound, wherein the polymer complex has a three-dimensional lattice-like structure containing a stack structure comprising the uncoordinating aromatic compound intercalated between aromatic compound ligands in a three-dimensional coordination network formed by coordinating the aromatic compound ligands to the central metal ion, and is provided with two or more kinds of channel groups each composed of channels identical with one another and having inherent affinity for guest molecules, and the uncoordinating aromatic compound has a group A'c represented by -Q4-COOH, Q4 representing a divalent organic group, at a specific position on the aromatic ring thereof, and is arranged regularly such that the group A'c is directed to the inside of a specific channel group B' out of the two or more kinds of channel groups.

ADVANTAGEOUS EFFECTS OF INVENTION

The present invention is an invention which chemically modifies the inside of channels by selectively incorporating guest molecules into the channels formed in a polymer complex and by utilizing progress of a specific chemical reaction proceeding in the channels being a reaction field. Therefore, according to the present invention, as Japanese Patent Application No. 2006-63416, which has been filed by the present inventors, a substituent which prevents construction of a polymer complex in the case that the substituent is preliminarily incorporated into an uncoordinating aromatic compound upon construction of the polymer complex from an aromatic ligand, a metal ion and the uncoordinating aromatic compound, and a substituent which cannot be introduced to an uncoordinating aromatic compound itself not constituting the complex polymer due to its instability, can be introduced to the uncoordinating aromatic compound after the polymer complex is formed. More specifically, the polymer complex provided by the present invention can exhibit highly selective behavior for guest molecules and highly specific characteristics as a reaction field.

COLOR DRAWINGS

The patent or application file contains at least one drawing executed in color.

DESCRIPTION OF EMBODIMENTS

Figure 1:
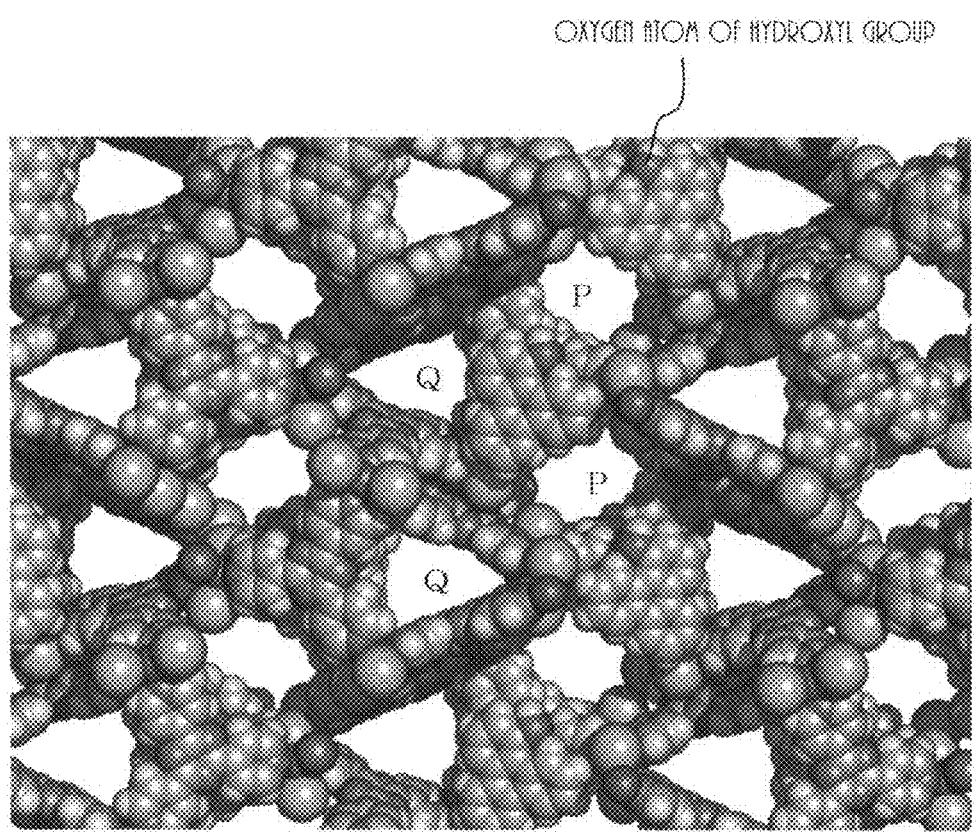
FIG. 1 is a projection view of the main framework of the polymer complex 4 drawn by using its van der Waals' radius, to show a method of calculating the channel size of the polymer complex 4.

A method for chemically modifying inner surfaces of channels of a polymer complex according to the present invention is a method for chemically modifying inner surfaces of channels of at least one kind of channel group in a polymer complex provided with two or more kinds of channel groups each composed of channels identical with one another and having inherent affinity for a guest molecule, wherein the polymer complex comprises an aromatic compound having two or more coordinating sites as a ligand, a metal ion as a central metal, and an uncoordinating aromatic compound, has a three-dimensional lattice-like structure containing a stack structure comprising the uncoordinating aromatic compound intercalated between aromatic compound ligands in a three-dimensional coordination network formed by coordinating the aromatic compound ligands to the central metal ion, and is provided with two or more kinds of the channel groups in the three-dimensional coordination network, and the uncoordinating aromatic compound has a specific substituent A at a specific position on the aromatic ring thereof, and is arranged regularly such that the substituent A is directed to the inside of a specific channel group B out of the two or more kinds of channel groups, the method comprising the steps of: including the guest molecule in the channel of the channel group B in which the substituent A is arranged; and reacting the guest molecule with the substituent A in the channel to convert the substituent A to a substituent A', and to arrange the substituent A' regularly directing to the inside of the channel of the channel group B or any channel of other channel groups.

Firstly, a polymer complex which is a subject of a chemical modification in the present invention will be explained.

A polymer complex which is a subject of a chemical modification in the present invention is the polymer complex in Japanese Patent Application No. 2006-63416 filed by the present inventors. That is, similar to the polymer complex in Japanese Patent Application No. 2004-382152 filed by some of the present inventors, the polymer complex has formed a three-dimensional coordination network by coordinate bonding of aromatic compound ligands to a central metal ion, and has a three-dimensional lattice-like structure containing a stack structure wherein an uncoordinating aromatic compound not involved in coordinate bonding is intercalated between aromatic compound ligands forming the three-dimensional coordination network. It is estimated that a plurality of channels (that is, channel groups) of two or more kinds each having inherent affinity for guest molecules (that is, having a specific molecular inclusion function) are formed in the polymer complex both from the three-dimensional coordination network formed by coordinate bonding of aromatic compound ligands to a central metal ion and from the stack structure formed by uncoordinating aromatic compounds incorporated into the three-dimensional coordination network and the aromatic compound ligands.

In the polymer complex, two or more kinds of channel groups are composed of channels having inherent affinity for guest molecules, and each of the channel groups can, by this inherent affinity, incorporate a different guest molecule selectively. That is, the polymer complex can incorporate one or more kinds of guest molecules into each of two or more kinds of channel groups contained in one polymer complex, that is, the polymer complex as a whole can selectively incorporate two or more kinds of guest molecules. Further, the guest molecules incorporated into the channels can also be selectively released. Selective incorporation of the guest molecule into the channel and/or selective release thereof from the channel includes not only incorporation of a specific component into the channel and/or release of a specific component from the channel, depending on the atmosphere in the channel, the size and shape of the channel, etc. but also selection of a guest molecule incorporated into the channel and/or a guest molecule released from the channel, depending on the temperature condition, atmosphere and time for guest exchange.

By suitably regulating the size of channels contained in channel groups formed in the polymer complex, the polymer complex can incorporate, into the channels, compounds ranging from gaseous small molecules to large molecules such as proteins and other biomolecules. That is, each of the channel groups can selectively incorporate a specific compound from a mixture containing two or more kinds of small-molecule to large-molecule compounds.

Accordingly, the polymer complex can separate specific two or more components, for example, from a mixture containing two or more components and can store them in the polymer complex. From mixture 1 containing one or more components, a specific component only is incorporated into a channel in a certain channel group 1, and while the component is maintained in the channel in channel group 1, another specific component from a mixture containing one or more components different from those of the mixture 1 can be incorporated into a channel in a certain channel group 2. Alternatively, when the polymer complex is used as a material constituting a partition wall, compound "a" selectively incorporated into channel group A can be transported through the channel group A, while compound "b" selectively incorporated into channel group B can be transported through the channel group B, between the areas separated with the partition wall. At this time, when the compound is transferred according to the concentration distribution of each compound or temperature distribution, the transportation direction of Compound a may be the same as the transportation direction of Compound b, or the transportation direction of Compound a may be opposite to the transportation direction of Compound b.

Two or more kinds of guest molecules incorporated respectively into channel groups can be released separately under different conditions. For example, when the polymer complex having the guest molecules incorporated respectively into two or more kinds of channel groups is placed under a predetermined condition, the guest molecule to be released varies depending on the time for which the polymer complex is exposed to this condition. Specifically, when the polymer complex having different components incorporated respectively into the channel groups 1 and 2 is heated, the component incorporated into the channel contained in the channel group 1 is first released, and when heating is further continued, the component incorporated into the channel contained in the channel group 2 can be released.

For the sake of descriptive convenience, expressions such as mixture 1, channel group 1 etc. have been used to describe the action of the polymer complex, but the expressions such as mixture 1 etc. do not refer to a specific mixture, channel group etc.

The polymer complex disclosed in Japanese Patent Application No. 2006-63416 is a polymer complex wherein substituents A are introduced into aromatic rings of uncoordinating aromatic compounds which construct a stack structure in a three-dimensional lattice-like structure together with aromatic compound ligands and form an inner wall of a channel, and is different from the polymer complex disclosed in Japanese Patent Application No. 2004-382152 in respect that channels in channel groups formed in the polymer complex are modified by the substituents A.

The substituents A introduced into aromatic rings of uncoordinating aromatic compounds are regularly oriented toward the inside of a channel in a specific channel group among two or more kinds of channel group, however, the detailed mechanism of the orientation of the substituent A is not completely elucidated. The orientation of the substituents A is determined by a stabilization effect attributable to overlapping of orbital shape ($\pi$-$\pi$ interaction) such as an overlap between the nodal plane of the HOMO of the uncoordinating aromatic compound and the nodal plane of the LUMO of the aromatic compound ligand in the stack structure and an overlap in electron distribution, in addition to the interactions (for example, hydrogen bonding, ionic bonding, electrostatic interactions [dipole interaction, quadrupole coupling], and steric interaction) between the substituents A and a specific channel group among the two or more kinds of channel groups. Apart of the inner face of the specific channel group is constituted by the substituents, thereby the shape, size and atmosphere of the channel group significantly change. As a result, characteristics of the channel environment of the channel group, for example, acidity/basicity, hydrophilicity/hydrophobicity, polarity, chirality, fluidity etc. are simultaneously significantly changed, and the affinity of the channel group for a specific guest molecule is changed.

The environmental characteristics in the channel can be controlled at will according to the properties, number and size of the substituent introduced into an aromatic ring of the uncoordinating aromatic compound, or a combination of substituents when two or more substituents are to be introduced. For example, a guest molecule that cannot be incorporated into the polymer complex comprising an uncoordinating aromatic compound into which no substituent is introduced can be incorporated into the polymer complex by introducing the substituents, or two or more guest molecules that cannot be separated from one another by only the channel atmosphere of each channel group in the polymer complex comprising an uncoordinating aromatic compound into which no substituent is introduced can be separated by the polymer complex wherein the shape or size of the channel is changed by introducing the substituents. Further, two or more kinds of channel groups can be made significantly different in channel environmental characteristics by regulating the type, number, introducing position etc. of substituents introduced to an aromatic ring of the uncoordinating aromatic compound, so that two or more guest molecules significantly different in characteristics can be incorporated into the respective channel groups, released and/or transported.

Specifically, when two channel groups different in hydrophilicity exist in the polymer complex comprising an uncoordinating aromatic compound into which no substituent is introduced, the introduction of substituent(s) into the uncoordinating aromatic compound can lead to (1) an increase in the hydrophilicity of one of the channel groups, (2) a decrease in the hydrophilicity of one of the channel groups, and (3) differentiation and improvement in hydrophilicity for each of the two channel groups. By increasing the difference in hydrophilicity of channels between the two channel groups according to (1) and (2), the affinity and specificity for the guest molecule can further be increased, and the ability to separate the guest molecule by incorporation or release thereof can be increased. A hydrophilic guest molecule that cannot be incorporated into a channel group constituted by the uncoordinating aromatic compound having no substituent introduced into it can be incorporated according to (3), and different guest molecules can be incorporated into the channel groups respectively. By introducing the substituents into the uncoordinating aromatic compound, a polymer complex having channels imparted every characteristic can be constructed to regulate not only the type, amount and arrangement of guest molecules incorporated into channels of the polymer complex, but also the reaction rate, reaction selectivity etc. of the guests, as described above. The polymer complex that has substituents introduced to uncoordinating aromatic compounds is excellent in molecular design given many choices for the type, number and position of substituents.

The introduction of substituents into aromatic rings of the uncoordinating aromatic compounds brings about another effect of increasing the regularity in arrangement of the uncoordinating aromatic compounds in the polymer complex. As described above, the substituents introduced into the uncoordinating aromatic compounds are oriented toward the inside of channels of a specific channel group out of the two or more channel groups, by physicochemical and/or steric interactions around the substituents, thereby conferring inherent characteristics on the channel environment. By such interactions, the regularity in arrangement of the uncoordinating aromatic compounds and aromatic compound ligands that are stacked with one another is increased, so the stack structure having the uncoordinating aromatic compounds and aromatic compound ligands stacked with one another is formed with regularity to form a strong structure.

By such high regularity of the stack structure, that is, by high structural regularity of the channel group, the environmental characteristics of channels in each of the channel groups can be uniformly maintained in the polymer complex. That is, it means that the selectivity of the channel group of the polymer complex for guest molecules is further increased.

In the polymer complex, the three-dimensional coordination network comprising aromatic compound ligands coordinated to a central metal includes a complexed three-dimensional coordination network comprising, for example, two or more independent three-dimensional coordination networks complexed with one another preferably so as to have the same space in common. Specific examples of the complexed three-dimensional coordination network can include an interpenetrated structure comprising two or more independent three-dimensional coordination networks intricately intertwined with one another so as to have the same space in common.

In the present invention, the aromatic compound is a compound having at least one aromatic ring and may have a substituent or may contain an endocyclic heteroatom. The aromatic compound ligand is a multidentate aromatic compound having two or more coordinating sites. Preferably, the aromatic compound ligand is an aromatic compound wherein all coordinating sites constituting the aromatic compound ligand exist in almost the same plane. Particularly, the aromatic compound ligand when viewed as a whole is preferably in the form of a pseudo-plane owing to its π-conjugated system; that is, the aromatic compound ligand is an aromatic compound ligand, at least a part of the molecular structure of which becomes unified by the π-conjugated system to give rise to a stable pseudo-plane structure containing all coordinating sites therein.

By using the aromatic compounds having such a pseudo-plane structure as the ligand, the aromatic compounds are coordinated to a central metal ion to form a three-dimensional coordination network having higher regularity and rigidity. By increasing the regularity of the three-dimensional coordination network, a stack structure comprising the aromatic compound ligands and the uncoordinating aromatic compounds can be stably formed, and simultaneously channels and channel groups having higher regularity can be formed. In addition, a complexed three-dimensional coordination network having two or more independent three-dimensional coordination networks complexed with one another may be formed.

The three-dimensional coordination network has rigidity so that the stability, strength etc. of the three-dimensional lattice-like structure formed therefrom can be kept high. The three-dimensional coordination network has rigidity so that the strength of the resulting polymer complex is made relatively high to render it usable in applications requiring strength, thus broadening the technical range in which the polymer complex can be used.

From the above viewpoint, the aromatic compound ligand that can be preferably used includes, but is not limited to, an aromatic compound ligand having coordinating atoms arranged radially at regular intervals in the extending direction of a plane formed by the π-conjugated system of the aromatic ring as the center.

The uncoordinating aromatic compound is an aromatic compound present in the polymer complex by intercalating between the aromatic compound ligands through a bond or interaction other than coordinate bond, and does not form a coordinate bond in the polymer complex. Accordingly, the uncoordinating aromatic compound as used herein may essentially have an ability to form a coordinate bond. Preferably, the uncoordinating aromatic compound is an aromatic compound in a molecule structure containing all aromatic rings unified in the π-conjugated system to have a stable pseudo-plane shape. By having the pseudo-plane shape, the uncoordinating aromatic compound can be easily intercalated between the aromatic compound ligands in a three-dimensional coordination network formed by the aromatic compound ligands, to form a stable structure having the aromatic compound ligand-uncoordinating aromatic compound-aromatic compound ligand stacked with one another.

When the aromatic compound ligand has also a pseudo-plane shape, the plane of the aromatic compound ligand and the plane of the uncoordinating aromatic compound are opposed to each other and stacked with each other thus allowing the π-π interaction to act on between the aromatic compound ligand-uncoordinating aromatic compound-aromatic compound ligand. As a result, the uncoordinating aromatic compound though having no direct bond to the aromatic compound ligand can be firmly confined between the aromatic compound ligands to form a more stable three-dimensional lattice-like structure.

The uncoordinating aromatic compound thus confined firmly between the aromatic compound ligands will not be extracted even under general guest exchange conditions with an aromatic compound as a guest molecule. Accordingly, the three-dimensional lattice-like structure having a stack structure in which the uncoordinating aromatic compound confined firmly between the aromatic compound ligands can be kept without changing its structure before and after guest molecules incorporated into the channels in the three-dimensional lattice-like structure are exchanged with other guest molecules.

In the polymer complex, which is a subject of a chemical modification of the present invention, the uncoordinating aromatic compound has the specific substituent A at a specific position of the aromatic ring thereof. The substituent A refers to a certain atom or atomic group substituted in place of a hydrogen atom at a specific position of the aromatic ring of the uncoordinating aromatic compound.

The substituent A can be selected appropriately to bring about desired environmental characteristics in a channel of channel group B and is not particularly limited as long as it can be introduced into specific channel group B out of the two or more kinds of channel groups formed in the polymer complex having the uncoordinating aromatic compound as a constituent element. The number of substituents A possessed by the uncoordinating aromatic compound may be 1 or more. When two or more substituents A are to be introduced, the substituents A may consist of one kind of substituent or a combination of two or more kinds of substituents. The position of the substituent A on the aromatic ring of the uncoordinating aromatic compound is not particularly limited, and a plurality of substituents A may be introduced so as to face the inside of channels of one kind of channel group or may be introduced so as to face respectively the inside of channels of two or more channel groups.

The stack structure comprising the uncoordinating aromatic compound intercalated between the aromatic compound ligands may have at least one unit consisting of the uncoordinating aromatic compound intercalated between the aromatic compound ligands, but preferably has a structure having the aromatic compound ligand and the uncoordinating aromatic compound stacked alternately with each other to a certain extent. In polymer complexes 1 to 17 described later, this stack structure is infinitely continued, but may not infinitely continued as long as the number of stacking units is sufficient for formation of two or more kinds of channel groups.

When the sufficiently three-dimensionally extending three-dimensional coordination network having the aromatic compound ligands coordinated to the metal ion, and the stack structure having the aromatic compound ligand and the uncoordinating aromatic compound stacked sufficiently with each other are formed, channels are formed in a long and thin form.

The two or more kinds of channel groups in the polymer complex are made different from one another in respect of their affinity for guest molecules by making them different in at least one factor selected from the size of a channel, the shape of a channel and the atmosphere in a channel, in comparison between two channel groups selected arbitrarily from the two or more kinds of channel groups. For increasing the affinity, for a specific guest molecule, of channels constituting each channel group in order to allow the channels to more selectively incorporate the specific guest molecule, it is preferable that two channel groups selected arbitrarily from the two or more kinds of channel groups are made different from each other in two or more factors selected from the size of a channel, the shape of a channel and the atmosphere in a channel, in comparison therebetween. Particularly, a channel group different from other channel groups in all the three factors (that is, the size of a channel, the shape of a channel and the atmosphere in a channel) is preferable because of higher selectivity for guest molecules.

A factor causing the atmosphere in channels to be made different among the channel groups is not particularly limited as long as the atmosphere in channels is thereby made different and the affinity for guest molecules is made different, and there are a variety of such factors depending on the properties of each guest molecule (for example, polarity etc.). The atmosphere in channels is significantly varied depending on characteristics of the substituent introduced into the uncoordinating aromatic compound. The atmosphere in channels is varied not only by the modification to channels attributable to characteristics of the substituent but also by a different ratio of the region over which the π-plane of aromatic compounds (aromatic compound ligands and/or uncoordinating aromatic compounds) constituting a wall forming a channel is exposed to an inner face of the wall, to the region over which hydrogen atoms of the aromatic compounds are exposed to the inner face of the wall.

When the size of the channel varies among the channel groups, the type of a guest molecule incorporated into the channel constituting each channel group and the amount of the guest molecule incorporated vary depending on the molecular size of the guest molecule. The size of the channel even in a continuous form varies depending on the position thereof on the polymer complex; that is, the minimum size of the channel significantly influences the minimum molecular size of the guest molecule that can be incorporated into the channel, while the maximum size of the channel significantly influences the maximum molecular size of the guest molecule that can be incorporated into the channel and the amount of the guest molecule that can be incorporated. Accordingly, a range of the size of the channel is an important factor influencing the affinity thereof for the guest molecule.

The channel formed in the three-dimensional lattice-like structure of the polymer complex meanders locally to some extent, but when the three-dimensional lattice-like structure is viewed as a whole, the channel extends in a predetermined direction with directionality. Accordingly, in the present invention, the diameter of an inscribed circle of the channel on a parallel face to a crystal plane most perpendicular to the direction in which the channel extends can be an indicator of channel size. The direction in which the channel extends is the direction of the channel that is regarded as one continuous void as a whole by disregarding local meandering thereof.

Figure 5:
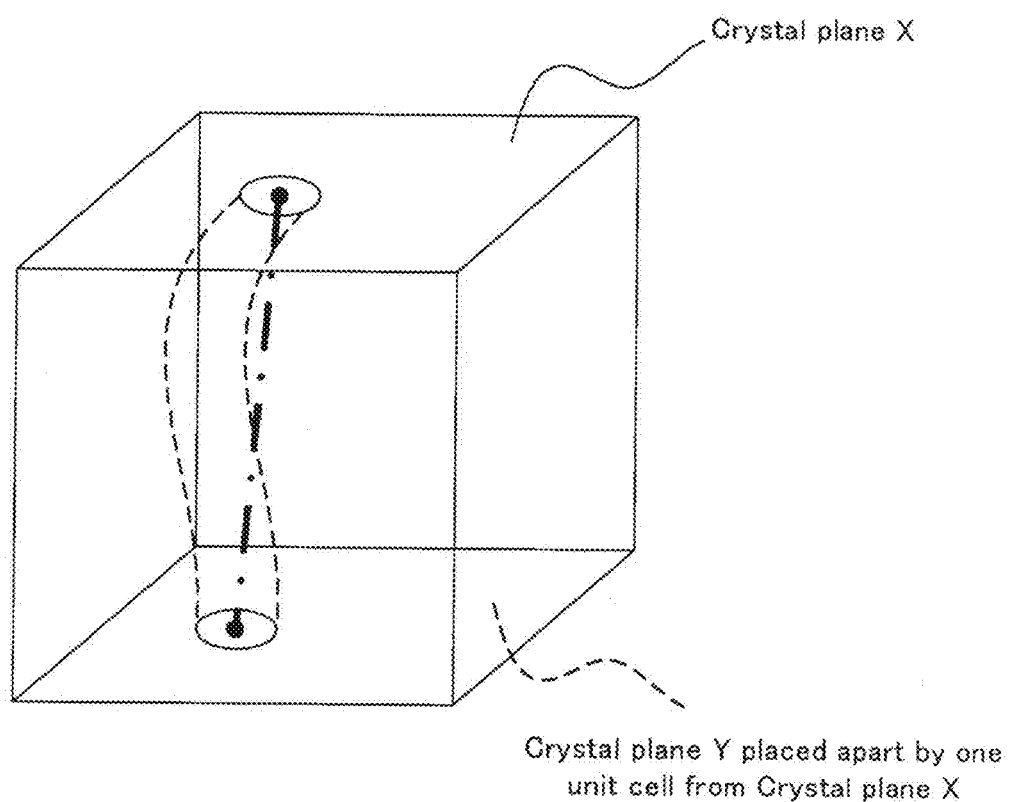
FIG. 5 is a view showing a method of determining the direction in which the channel extends.

The direction in which the channel extends can be determined, for example, as follows. Crystal plane X (plane A, plane B, plane C or its diagonal plane) in a suitable direction across the channel whose size is to be measured, and crystal plane Y placed apart by one unit cell from the crystal plane X, are selected, and sectional views of the channel on the respective crystal planes X and Y are drawn. Then, a straight line (alternate long and short dash line) is drawn from the center of the section of the channel on one crystal plane to the center of the section thereof on another crystal plane (see FIG. 5). The direction of the straight line thus obtained agrees with the direction in which the channel extends. Then, a crystal plane that intersects with the obtained straight line at the nearest angle to 90° is selected, and the diameter of an inscribed circle of the channel on this crystal plane can be regarded as the size of the channel.

If the size of the channel is assumed to be a sole factor that determines the selectivity of the channel for guest molecules, a guest molecule having a smaller molecular size than the diameter of an inscribed circle of the channel can usually be incorporated into the channel without difficulty, and thus the definition of channel size in terms of the diameter of the inscribed circle thereof has a significant meaning. The channel groups may be different from one another in channel size, and there is no limitation to the difference in channel size, etc., among the channel groups.

The size of the channel to be formed in the polymer complex which is a subject of a chemical modification in the present invention may be appropriately designed depending on a component desired to be selectively incorporated, and the channel can, depending on its size, incorporate components ranging from gaseous small molecules to large molecules such as proteins and other biomolecules. Specifically, the diameter of the inscribed circle can be 2 to 70 Å, preferably 2 to 20 Å. Alternatively, the major axis of an inscribed ellipse of the channel on the parallel face can be 5 to 70 Å, and the minor axis of an inscribed ellipse, of the channel can be 2 to 50 Å. When the channel sizes of the respective channel groups are different, the channel sizes of the respective channel groups are different from one another preferably in the range defined above.

It is preferable that as factors to be compared among the different channel groups, the minor and major axes of an inscribed ellipse of the channel, together with the diameter of an inscribed circle of the channel, are considered as measures for specifying the deviation of the channel shape from the inscribed circle.

Now, the method for measurement (calculation) of the size of a channel is described by reference to FIG. 1. FIG. 1 is a projection view, on crystal plane (010), of a main backbone of polymer complex 4, which can be a subject of a chemical modification, $\{[(ZnI_2)_3 \ (C)_2 \ (D_4)](nitrobenzene)_4 \ (methanol)_n\}_z$ (C: tris(4-pyridyl)triazine; $D_4$: 1-hydroxytriphenylene; and n and z are nonstoichiometric composition) drawn by using its van der Waals' radius, wherein guest molecules incorporated into channels P and Q are not shown.

In the polymer complex 4, the channels P and Q extend in a direction (which is not a local direction but an overall direction as described above) perpendicular to the crystal plane (010), that is, in a direction perpendicular to the plane of page of FIG. 1. Because the plane of page of FIG. 1 is the parallel plane described above, the diameter of an inscribed circle of the channel shown in FIG. 1 and/or the major and minor axes of an inscribed ellipse thereof are measured, and these measures can be reduced to the actual size of the channel.

The size of the channel can be regulated by molecular design, for example, by designing the molecular size of the aromatic compound ligand or uncoordinating aromatic compound constituting the three-dimensional lattice-like structure, the coordination force between the central metal ion and the aromatic compound ligand, and the type, number and position of substituents introduced into the uncoordinating aromatic compound.

When the channel groups are different in channel shape, the guest molecule that can be incorporated into channels constituting each channel group varies depending on the shape of the guest molecule, even if the channel groups are almost identical in the diameter of the inscribed circle or in the major and minor axes of the inscribed ellipse. The channels constituting each channel group may be different in channel shape at least in one position and may not be different in the whole of a continuous channel.

The shape of the channel can also be regulated by molecular design, for example, by designing the shape of the aromatic compound ligand or uncoordinating aromatic compound constituting the three-dimensional lattice-like structure, and the type, number and position of substituents introduced into the uncoordinating aromatic compound.

Figure 6:
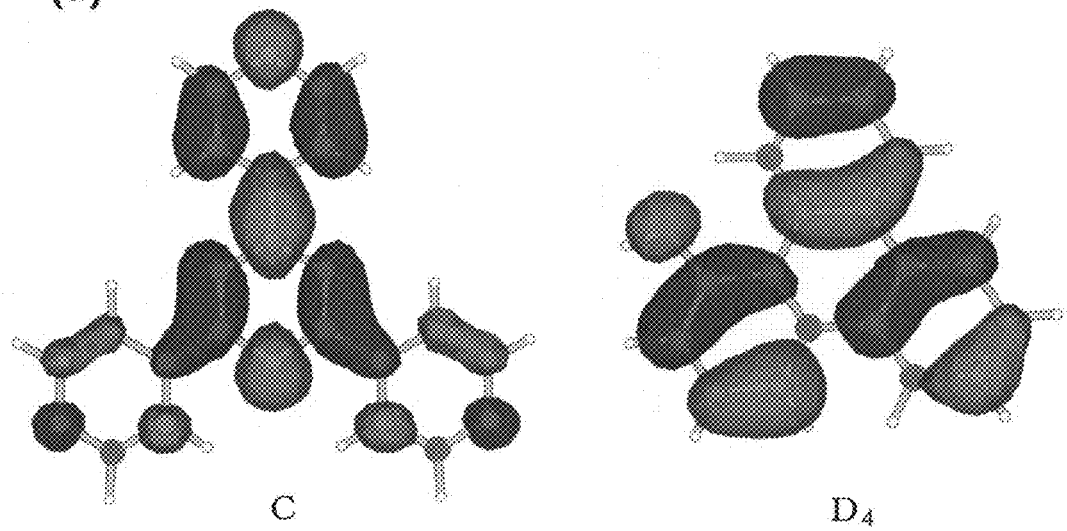
FIG. 6 is a view showing the HOMO of 1-hydroxytriphenylene and the LUMO of tris(4-pyridyl)triazine (FIG. 6a) and a view showing stacking thereof (FIG. 6b).
Figure 6:
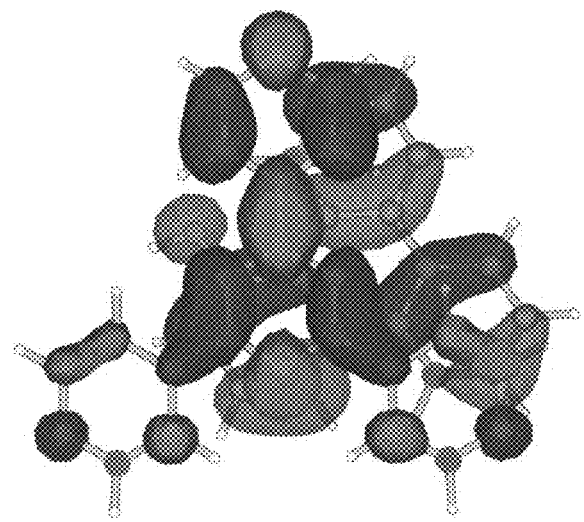
Figure 7:
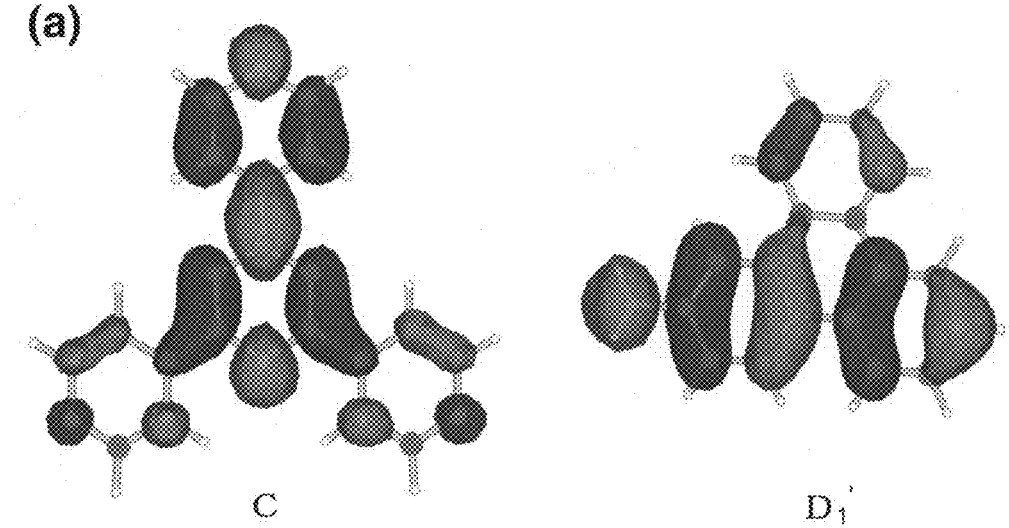
FIG. 7 is a view showing the HOMO of 2-aminotriphenylene and the LUMO of tris(4-pyridyl)triazine (FIG. 7a) and a view showing stacking thereof (FIG. 7b).
Figure 7:
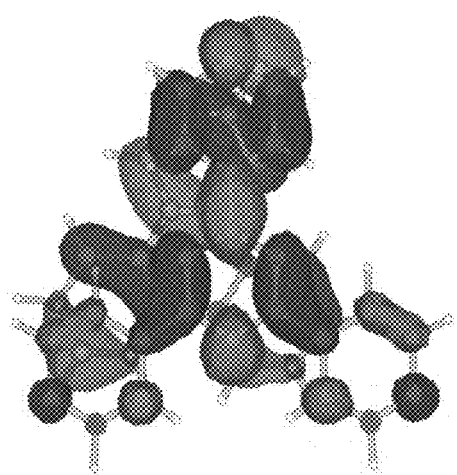

In the stack structure in the three-dimensional coordination network, by selecting the uncoordinating aromatic compound, a substituent to be introduced into the uncoordinating aromatic compound and the aromatic compound ligand so that the HOMO (highest occupied molecular orbital) of the uncoordinating aromatic compound and the LUMO (lowest unoccupied molecular orbital) of the aromatic compound ligand overlap in the number and position of nodal planes, in electron distribution, and in the orbital shape with respect to energy level (see FIG. 6(b) and FIG. 7(b)) and the stack structure to be stabilized, the stack structure to be formed in the polymer complex can be predicted and efficient molecular design is feasible.

FIG. 6(a) is a view showing the LUMO of tris(4-pyridyl)triazine (C) and the HOMO of 1-hydroxytriphenylene ($D_4$) in the polymer complex 4 constructed by using tris(4-pyridyl)triazine (C) [an aromatic compound ligand] and 1-hydroxytriphenylene ($D_a$) [uncoordinating an aromatic compound], and FIG. 6(b) is a view showing stacking of HOMO of $D_4$ and LUMO of C. Also, FIG. 7(a) is a view showing the LUMO of tris(4-pyridyl)triazine (C) and the HOMO of 2-aminotriphenylene ($D'_1$) in the polymer complex constructed by using tris(4-pyridyl)triazine [an aromatic compound ligand] (C) and 2-aminotriphenylene [uncoordinating an aromatic compound] ($D'_1$), and FIG. 7(b) is a view showing stacking of HOMO of $D'_1$ and LUMO of C.

Hereinafter, the aromatic compound ligand, the uncoordinating aromatic compound and the metal ion as a central metal, which constitute the polymer complex, are specifically described.

Specific examples of the aromatic compound ligand include, for example, aromatic compounds represented by the following Formula 1:

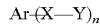     Formula 1 wherein Ar is a structure having an aromatic ring, X is a divalent organic group or a single bond through which Ar and Y are directly bound to each other, Y is a coordinating atom or a coordinating atom-containing atomic group, n is a number of 3 to 6, and a plurality of Xs contained in one molecule may be different from one another, and a plurality of Ys may be different from one another.

In Formula 1, Ar has a π plane forming a pseudo-plane structure and has a π-π interaction with the uncoordinating aromatic compound. Ar is not particularly limited and may be appropriately selected by considering a certain influence of the molecular size of the aromatic compound ligand on the size of a channel to be formed in the polymer complex. Specific examples of Ar include a monocyclic aromatic ring, particularly a 6-membered aromatic ring or a condensed polycyclic aromatic ring bi- to pentacyclic, particularly a condensed polycyclic aromatic ring having two to five 6-membered aromatic rings condensed therein.

For easiness in synthesis, Ar is preferably a monocyclic aromatic ring such as a 6-membered aromatic ring. Examples of the monocyclic 6-membered aromatic ring include a benzene ring, a triazine ring, a pyridine ring, a pyrazine ring etc.

Ar may be a structure having an aromatic ring, and may partially contain an alicyclic cyclic structure or an endocyclic heteroatom. Ar may have a substituent other than —(X—Y).

When X intermediating between Ar and Y in Formula 1 is a divalent organic group, its chain length etc. may be selected appropriately depending on the required size etc. of a channel formed in the polymer complex. For forming a channel that can incorporate an organic compound having a relatively large molecular size, examples of X include a divalent aliphatic group having 2 to 6 carbon atoms, a 6-membered divalent monocyclic aromatic ring, and a condensed polycyclic aromatic ring having two to four 6-membered aromatic rings condensed therein.

The aromatic ring may contain an endocyclic hetero atom or may have a substituent. The aromatic ring may partially contain an alicyclic structure. The alicyclic group may have a branched structure, may contain an unsaturated bond, or may contain a heteroatom.

Specific examples of the divalent organic group includes a monocyclic aromatic ring such as a phenylene group, thiophenylene, or furanylene, a condensed polycyclic aromatic ring having benzene rings condensed therein, such as a naphthyl group or anthracene, an aliphatic group such as an acetylene group, an ethylene group, an amido group, or an ester group, and a group wherein these groups, the number of which is arbitrary, are linked to one another in an arbitrary order. A plurality of Xs contained in one molecule may be the same or different from one another, but is usually preferably the same from the viewpoint of easy synthesis.

Y is a coordinating atom, or a coordinating atom-containing atomic group, which can be coordinated to a central metal ion serving as a central metal, and is not particularly limited as long as it can be coordinated to the central metal ion to form a three-dimensional coordination network. Examples of Y include groups represented by the following Formula 2:

Formula 2

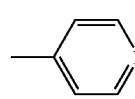

2 (a)

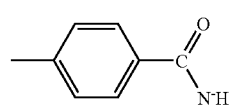

2 (b)

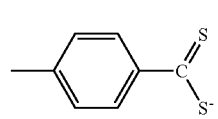

2 (c)

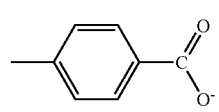

2 (d)

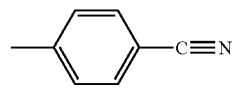

2 (e)

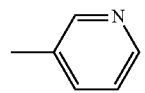

2 (f)

Formulae 2(b), 2(c) and 2(d) have a resonance structure so that a lone electron pair can be given to the central metal ion. Hereinafter, the resonance structure of Formula 2(c) is shown as a typical example.

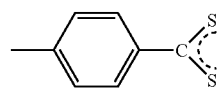

Y may be a coordinating atom itself or may be an atomic group containing a coordinating atom. For example, the above-mentioned 4-pyridyl group (2(a)) is an atomic group containing a coordinating atom (N). From the viewpoint of attaining suitable coordination strength upon coordination bonding to the central metal ion via a lone electron pair possessed by the coordinating atom of Y, the pyridyl group (2(a), 2(f)) is particularly preferable among the groups of the above formulae.

A plurality of Ys contained in one molecule may be the same or different from one another.

As described above, the aromatic compound ligand is preferably an aromatic compound wherein all coordinating sites constituting the aromatic compound ligand exist in almost the same plane. Particularly, the aromatic compound ligand when viewed as a whole is preferably in the form of a pseudo-plane owing to its π-conjugated system. That is, all Ys contained in the aromatic compound ligand (1) represented by Formula 1 above are present preferably in almost the same plane. Particularly, a plurality of —(X—Y) bound to Ar become unified by the π-conjugated system to form a stable pseudo-plane structure in which all Ys exist.

From the viewpoint of exhibiting an effective π-π interaction with the uncoordinating aromatic compound, it is preferable that in the aromatic compound ligand wherein Ar and a plurality of —(X—Y) become unified by the π-conjugated system to form a pseudo-plane structure, —(X—Y) has a rigid linear structure, and in an environment intended to be used, its rotation on the axis is restricted.

From this viewpoint, preferable examples of X among those mentioned above include a single bond through which Ar and Y are directly bound to each other, an aromatic group, for example a monocyclic aromatic ring such as a phenylene group or a condensed polycyclic aromatic ring such as a naphthyl group or anthracene, an aliphatic group such as an acetylene group or an ethylene group, and a group wherein these groups, the number of which is arbitrary, are linked to one another in an arbitrary order. When —(X—Y) is a structure composed of an aromatic ring, an acetylene group or an ethylene group or a structure having these groups linked therein, its axial rotation is restricted due to steric hindrance. When the structure composed of an aromatic ring, an acetylene group or an ethylene group forms a conjugated system where π electrons are delocalized, its axial rotation is restricted by an energy barrier of the conformation. Accordingly, the aromatic compound ligands represented by Formula 1 can become unified to attain a pseudo-plane structure, to form a stable three-dimensional coordination network.

From the viewpoint of ease in design of the polymer complex, the coordinating atom represented by Y or the coordinating atom contained in Y preferably has a lone electron pair in the extending direction of the axis of —(X—Y) having the rigid linear structure described above.

The number of —(X—Y) bound to Ar is usually 3 to 6, depending on the structure of Ar. —(X—Y) is bound to Ar preferably such that its coordinating atoms are arranged radially at regular intervals in almost the same plate with Ar as the center.

The aromatic compound ligand (1) having a structure wherein coordinating atoms are arranged radially at regular intervals in the extending direction of a plane formed by the π-conjugated system of the aromatic ring with the aromatic ring-containing structure Ar as the center as described above includes aromatic compound ligands represented by the following Formula 4:

Formula 4

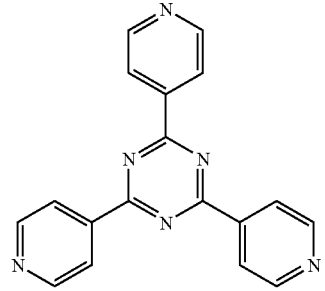

4 (a)

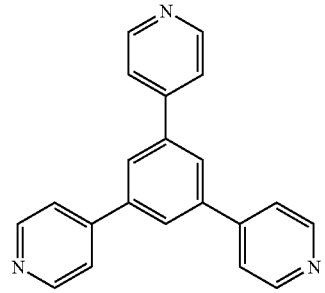

4 (b)

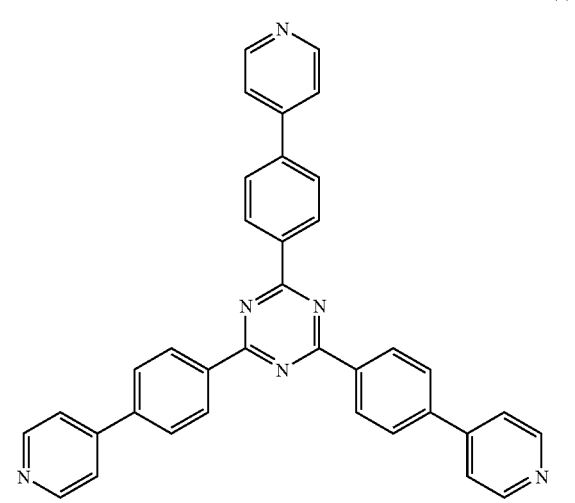

4 (c)

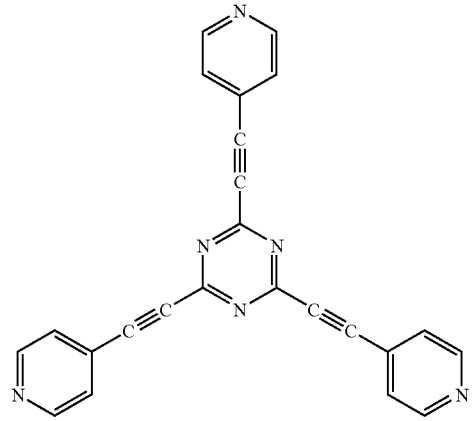

4 (d)

Among compounds in Formula 4 above, tris(4-pyridyl) triazine (Formula 4(a)) [2,4,6-tris(4-pyridyl) 1,3,5-triazine] is particularly preferable because it is deficient in electron and thus has strong interaction attributable to charge transfer with the uncoordinating aromatic compound so that a strongly stabilized stack structure with the uncoordinating aromatic compound can be formed.

As the uncoordinating aromatic compound, on the other hand, a condensed polycyclic aromatic compound can be mentioned. This is because for the reason described above, the uncoordinating aromatic compound is preferably an aromatic compound having all rings contained in a molecular structure unified by the π-conjugated system to have a stable pseudo-plane shape.

The condensed polycyclic aromatic compound includes a bicyclic to heptacyclic compound. For stabilizing the stack structure with the aromatic compound ligands, the condensed polycyclic aromatic compound preferably has a planar shape extending to a certain extent. Such a condensed polycyclic aromatic compound includes compounds represented by the following Formula 5:

Formula 5

5 (a)

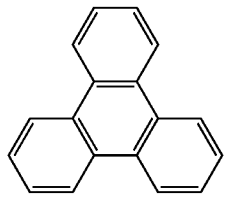

5 (b)

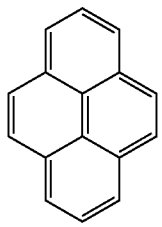

5 (c)

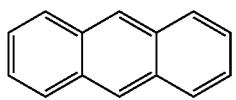

5 (d)

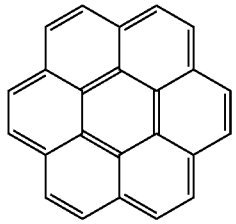

5 (e)

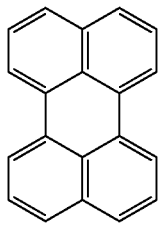

5 (f)

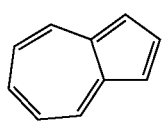

5 (g)

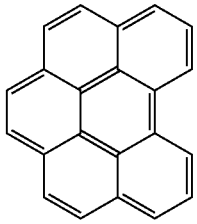

5 (h)

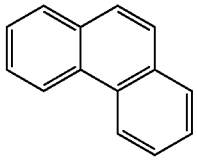

5 (i)

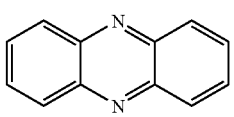

The substituent A introduced into the aromatic ring of the uncoordinating aromatic compound is not particularly limited as long as it has such a size as to permit the substituent A to enter into a channel formed in the polymer complex. Accordingly, the substituent A attaining the effect of substituent introduction varies depending on the size of a channel formed in the polymer complex. For example, the substituent A includes at least one functional group selected from —W—OH, —W—NH$_2$, —W—NO$_2$, —W—CH$_3$, —W—OCOCH$_3$, —W—CHO, an alkyl ether chain, an alkylthio ether chain, an alkylene glycol chain, and a peptide chain, wherein W represents a divalent organic group or a single bond.

Although the divalent organic group W is not particularly limited as long as the obtained substituent A has such a size as to permit it to enter into the specific channel B, the divalent organic group W is preferably a lower carbon chain, specifically a carbon chain having 1 to 5 carbon atoms or a single bond, particularly preferably a carbon chain having 1 to 3 carbon atoms or a single bond. An alkyl or alkylene group of the alkyl ether, alkyl thio ether, or alkylene glycol is preferably a lower carbon chain, specifically a carbon chain having 1 to 5 carbon atoms, particularly preferably a carbon chain having 1 to 3 carbon atoms. The alkylene glycol chain or the peptide chain is preferably a chain containing 1 to 2 alkylene glycol or peptide units.

Specific substituent A can be exemplified by —CH$_2$—OH, —CH$_2$CH$_2$—OH, —OH, —CH$_2$—NH$_2$, —CH$_2$CH$_2$—NH$_2$, —NH$_2$, —CH$_2$—NO$_2$, —CH$_2$ CH$_2$—NO$_2$, —NO$_2$, —CH$_2$—CH$_3$, —CH$_2$ CH$_2$—CH$_3$, —CH$_3$, —CH$_2$—OCOCH$_3$, —CH$_2$CH$_2$—OCOCH$_3$, —OCOCH$_3$, —O—CH$_3$, —O—CH$_2$CH$_3$, —S—CH$_3$, —S—CH$_2$CH$_3$, —O—CH$_2$CH$_2$—OH, —CH$_2$—CHO, —CH$_2$CH$_2$—CHO and —CHO.

Substituents A having relatively strong interactions such as hydrogen bonding, ionic bonding, and electrostatic interactions (dipole interaction, quadrupole coupling) can be selected to regulate the orientation of the substituents and the arrangement of the uncoordinating aromatic compounds. Substituents that can exhibit higher interatomic or intermolecular interactions such as electrostatic interactions and steric effects than van der Waals' force can be introduced into aromatic rings of the uncoordinating aromatic compounds, whereby the molecular arrangement, by self-assembly, of the aromatic compound ligands and the uncoordinating aromatic compounds is more accurately regulated, and the orientation of the substituents A themselves and the regularity of the stack structure composed of the aromatic compound ligand and the uncoordinating aromatic compound can be increased, in the three-dimensional coordination network formed by coordinating the aromatic compound ligands to metal ions.

Among those described above, the substituents A exhibiting relatively strong interactions described above includes —$CH_2$—OH, —$CH_2CH_2$—OH, —OH, —$CH_2$—$NH_2$, —$CH_2CH_2$—$NH_2$, —$NH_2$, —$CH_2$—$NO_2$, —$CH_2CH_2$—$NO_2$, —$NO_2$, —$CH_2$—$OCOCH_3$, —$CH_2CH_2$—$OCOCH_3$, —$OCOCH_3$, and —O—$CH_2CH_2$—OH.

From the viewpoint of constructing a stable network structure by forming a strong π-π stacking structure, the substituent A is preferably a highly electron-donating substituent. The highly electron-donating substituent includes —W—OH, —W—$CH_3$, and an alkyl ether chain, and specific examples include —$CH_2$—OH, —$CH_2CH_2$—OH, —OH, —$CH_2$—$NH_2$, —$CH_2CH_2$—$NH_2$, —$NH_2$, —$CH_2$—$CH_3$, —$CH_2CH_2$—$CH_3$, —$CH_3$, —O—$CH_3$, and —O—$CH_2CH_3$.

It is important that the channel containing the substituents A oriented toward the inner face thereof is not occupied by the substituents A in order to incorporate a guest molecule, that is, to exhibit an inclusion behavior. From this viewpoint, the size of the substituent A is preferably determined so as to be adapted to the size of the channel. Because the size of a space in the channel toward which the substituents A are oriented also varies depending on the size of the substituents A, the size of the substituents A can be determined so as to be adapted to the guest molecule intended to be incorporated.

Accordingly, the size of the preferable substituent A varies depending on the size of the channel and the size of the guest molecule intended to be included, but from the viewpoint of forming the channel showing an inclusion behavior, the substituent A is preferably an atomic group having 3 or less atoms in total excluding hydrogen atoms. Specifically, the above-mentioned W is preferably a carbon chain having 1 to 2 carbon atoms or a single bond, and when an alkyl ether chain is selected as the substituent A, W is preferably a carbon chain having 1 to 2 carbon atoms. Examples of such substituent A include —$CH_2$—OH, —$CH_2CH_2$—OH, —OH, —$CH_2$—$NH_2$, —$CH_2CH_2$—$NH_2$, —$NH_2$, —$NO_2$, —$CH_2$—$CH_3$, —$CH_2CH_2$—$CH_3$, —$CH_3$, —$OCOCH_3$, —O—$CH_3$, —O—$CH_2CH_3$, —S—$CH_3$, and —S—$CH_2CH_3$.

The number of substituents A introduced into the uncoordinating aromatic compound is not limited either, and may be 1 or more. When two or more substituents A are introduced, the substituents A may be the same or different from one another. Depending on the number of substituents A introduced, the shape, size and atmosphere of the channel can be regulated as described above.

The position of the substituent introduced into the aromatic ring of the uncoordinating aromatic compound is not particularly limited. Depending on the position of the substituent introduced, the shape and size of the channel are changed, and the orientation of the substituent itself may also be changed by the steric effect. When a plurality of substituents are introduced into the uncoordinating aromatic compound, the plurality of substituents can, by the positions of the respective substituents introduced, be directed toward the same channel to modify one channel group with the plurality of substituents, or directed toward different channels to modify different channel groups with the respective substituents.

As the central metal ion to which the aromatic compound ligands are coordinated, various metal ions may be appropriately selected and used, among which transition metal ions are preferable. The transition metal in the present invention encompasses zinc, cadmium and mercury in the XII group in the periodic table. Particularly, the VIII to XII group elements are preferable, and specifically zinc, copper, nickel, cobalt, iron, silver etc. are preferable.

In the present invention, the central metal ion exists usually in the form of a compound such as a metal salt in the three-dimensional lattice-like structure. Metal compounds containing these central metal ions include metal halide salts, and specifically, $ZnI_2$, $ZnCl_2$, $ZnBr_2$, $NiI_2$, $NiCl_2$, $NiBr_2$, $CoI_2$, $CoCl_2$, $CoBr_2$ etc. are preferably used.

When the aromatic compound of Formula 1, particularly the aromatic compound of Formula 4, is used as the aromatic compound ligand, and a condensed polycyclic aromatic compound, particularly the aromatic compound of Formula 5, is used as the uncoordinating aromatic compound, the size of a channel contained in a channel group selected from two or more kinds of channel groups formed in the polymer complex can be as follows: the diameter of the inscribed circle in the parallel plane mentioned above is in the range of 3 to 10 Å, particularly 4.5 to 7.0 Å, the major axis of the inscribed ellipse of the channel on the parallel plane is in the range of 5 to 15 Å, particularly 8.5 to 10.0 Å, and the minor axis of the inscribed ellipse of the channel is in the range of 3 to 13 Å, particularly 6.0 to 8.0 Å. The polymer complex in which channels of such sizes are formed can incorporate compounds of relatively large sizes, such as organic compounds.

Now, the process for producing the polymer complex, and the structure of the polymer complex, are described in more detail by reference to the polymer complex obtained by using tris(4-pyridyl)triazine as the aromatic compound ligand, triphenylene having an —OH group introduced at position 1 (1-hydroxytriphenylene) as the uncoordinating aromatic compound, and $ZnI_2$ as a metal compound containing a metal ion as the central atom.

In Formula 6 below, tris(4-pyridyl)triazine (C) is a compound having a pseudo-plane structure having a triazine ring and three pyridyl rings on almost the same plane, and three nitrogen atoms of 4-pyridyl can be coordinated to a metal ion. 1-Hydroxytriphenylene ($D_4$) is also a compound having a pseudo-plane structure, and a hydroxyl group (—OH) is bound to an aromatic ring of the triphenylene skeleton thereof. The polymer complex having a three-dimensional lattice-like structure formed from tris(4-pyridyl) triazine (C) (hereinafter referred sometimes in the following formula to as (C)), $ZnI_2$, and 1-hydroxytriphenylene ($D_4$) (hereinafter referred sometimes in the following formula to as ($D_4$)) is formed by allowing tris(4-pyridyl)triazine (C) and 1-hydroxytriphenylene ($D_4$) in a coexisting state to act on $ZnI_2$ (Formula 6).

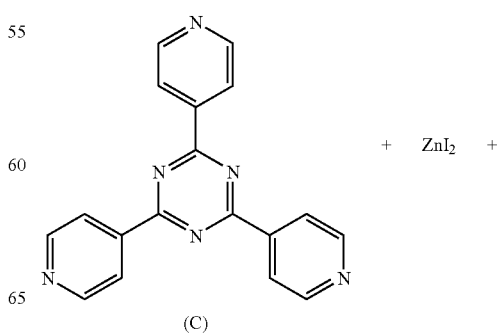

Formula 6

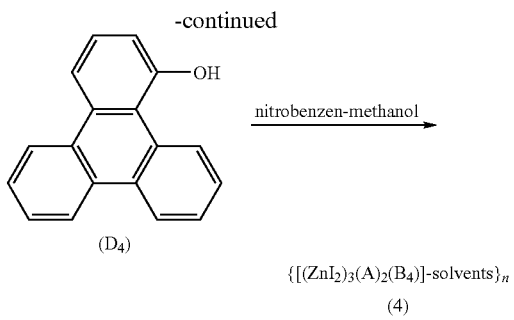

(D4)

$\{[(ZnI_2)_3(A)_2(B_4)]\text{-solvents}\}_n$ (4)

For example, a polymer complex (hereinafter referred to sometimes as polymer complex 4) having a single-crystal structure represented by $\{[(ZnI_2)_3(C)_2(D_4)]$ (nitrobenzene)$_4$ (methanol)$_n\}_z$ (n, z: nonstoichiometric composition)) can be produced by using a triple-layered solution (a top layer: a solution of $ZnI_2$ in methanol; a middle layer: methanol; a bottom layer: a solution of tris(4-pyridyl)triazine and 1-hydroxytriphenylene in nitrobenzene-methanol). At this time, the middle layer that is a methanol layer is a buffer for preventing $ZnI_2$ from being rapidly mixed with tris(4-pyridyl) triazine and 1-hydroxytriphenylene. By being left this triple-layered solution, $ZnI_2$ is mixed gradually with tris(4-pyridyl) triazine and 1-hydroxytriphenylene (double-layer diffusion method), thereby forming polymer complex 4.

Figure 2:
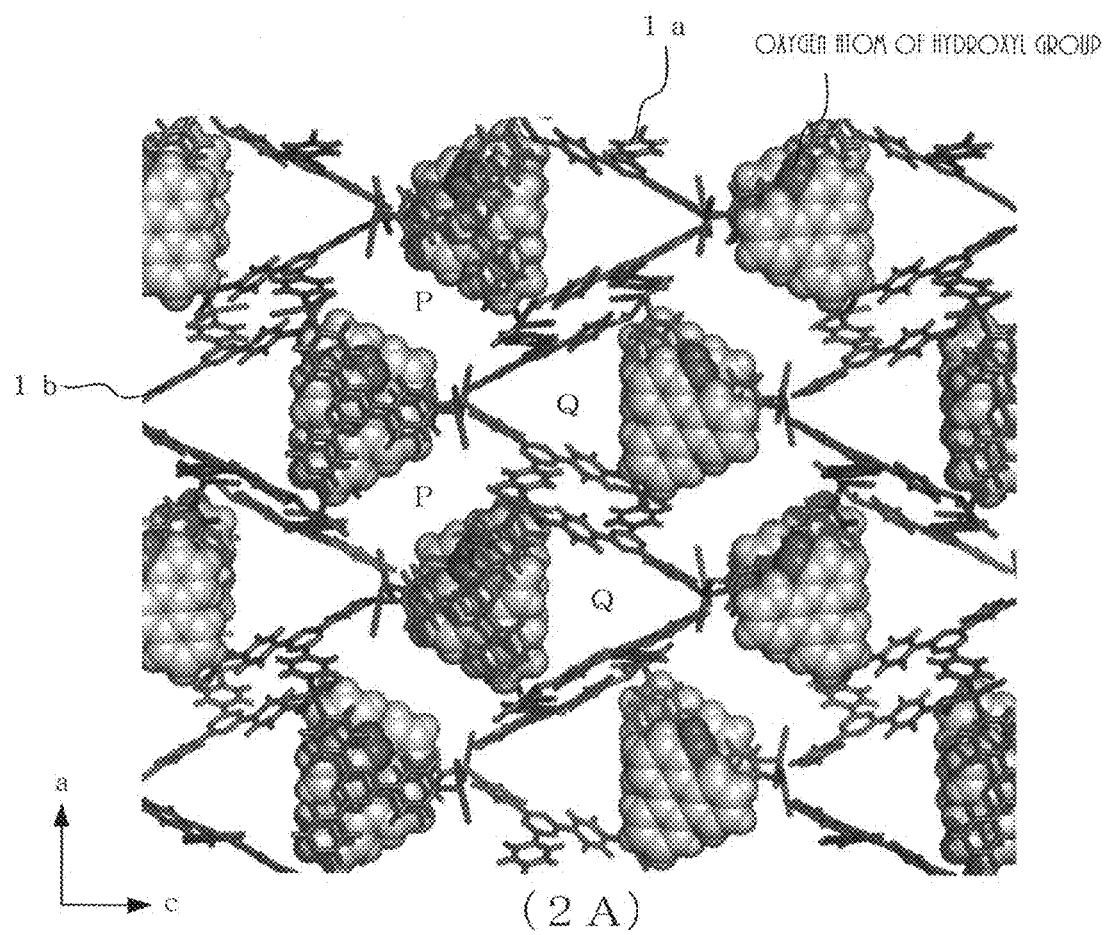
FIG. 2 is a view showing a crystal structure of the polymer complex 4 (FIG. 2A) and a periodic structure having tris(4-pyridyl)triazine and 1-hydroxytriphenylene alternately stacked therein (FIG. 2B).
Figure 2:
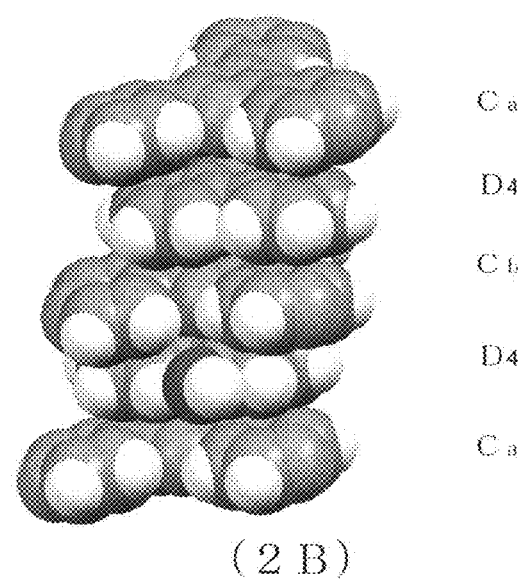

FIG. 2 is a view of the polymer complex 4, which was obtained by X-ray crystal structure analysis. FIG. 2(A) with an axis b in a direction perpendicular to the plane of this figure (crystal 010 plane) shows an interpenetrated structure in the three-dimensional lattice-like structure of the polymer complex 4 on a plane of section perpendicular to the direction (axis b) in which channels P and Q (described later) extend. In FIG. 2(A), guest molecules incorporated into channels P and Q are not shown.

As shown in FIG. 2(A), the polymer complex 4 has a complexed three-dimensional coordination network formed by interpenetration of three-dimensional coordination networks 1a and 1b each having a plurality of tris(4-pyridyl) triazine and $ZnI_2$ bound three-dimensionally to each other via coordinate bonding. The three-dimensional coordination network 1a and the three-dimensional coordination network 1b do not have a direct or indirect bond via which both the networks have $ZnI_2$ in common, and the two networks are independent of each other and are interpenetrated to each other so as to have the same space in common.

Further, 1-hydroxytriphenylene (D$_4$) is intercalated firmly between the π-plane of tris(4-pyridyl)triazine (C$_a$) in the three-dimensional coordination network 1a and the π-plane of tris(4-pyridyl)triazine (C$_b$) in the three-dimensional coordination network 1b (see FIG. 2(B)). At this time, 1-hydroxytriphenylene (D$_4$) is incorporated between tris(4-pyridyl) triazines (C$_a$) and (C$_b$) via the π-π interaction between (C$_a$) and (C$_b$) and does not have a direct bond to tris(4-pyridyl) triazine. However, it is estimated that the solid-state structure of the polymer complex 4 is stabilized by a structure composed of an infinite number of continuing stack structures having triphenylene intercalated between the π-planes of two tris(4-pyridyl)triazines (••C$_a$••D$_4$••C$_b$••D$_4$••). Because triphenylene was not extracted in a guest exchange experiment of the polymer complex consisting of tris(4-pyridyl)triazine, triphenylene and $ZnI_2$ in Japanese Patent Application No. 2004-382152, it is estimated that 1-hydroxytriphenylene (D$_4$) also functions as a part of the main framework of the polymer complex 4.

This firm confinement of 1-hydroxytriphenylene (D$_4$) is ascribed to charge-transfer (CT) interaction among C$_a$-D$_4$-C$_b$. In addition, calculation predicted that the HOMO (highest occupied molecular orbital) of 1-hydroxytriphenylene (D$_4$) and the LUMO (lowest unoccupied molecular orbital) of tris(4-pyridyl)triazine (C) have a suitable overlapping orbital shape with respect to nodal planes, electron distribution and energy level (see FIG. 6(a) and FIG. 6(b)). For convenience of theoretical calculation for this result, the LUMO of molecule C not forming the complex was handled as a model of LUMO of C in the framework of the polymer complex 4.

In the polymer complex 4, two kinds of channels (P and Q) arranged regularly in the three-dimensional lattice-like structure thereof exist as shown in FIG. 2. The channels P and Q are formed regularly between stack structures having tris(4-pyridyl)triazine (C) and 1-hydroxytriphenylene (D$_4$) stacked alternately with one another. The channel P is almost cylindrical and mainly surrounded by hydrogen atoms on the edge of the π-plane of infinitely stacked tris(4-pyridyl)triazine (C) and 1-hydroxytriphenylene (D$_4$). The hydroxy group of 1-hydroxytriphenylene (D$_4$) is directed to an inner face of channel P to form a part of the inner face of channel P. Accordingly, the channel P is modified with the hydroxy group, thus attaining higher hydrophilicity, polarity and acidity than those of channel Q.

On the other hand, channel Q is in the form of a pseudo-triangular prism, where two of the three walls forming the triangular prism are surrounded by the π-plane of tris(4-pyridyl)triazine (C), and the third is surrounded by hydrogen atoms on the edge of the π-plane of infinitely stacked tris(4-pyridyl)triazine (C) and 1-hydroxytriphenylene (D$_4$). The hydroxy group of 1-hydroxytriphenylene (D$_4$) is not oriented toward an inner face of channel Q. The channel P and Q are in a slightly meandering, long and thin form.

X-ray structure analysis revealed that the temperature factor of the atoms constituting the D$_4$ molecule is insignificant and very few disorders in the D$_4$ arrangement in the crystal exist in the stack structure formed from tris(4-pyridyl)triazine (C) as the aromatic compound ligand and 1-hydroxytriphenylene (D$_4$) as the uncoordinating aromatic compound in the polymer complex 4. This result indicates that a structure with extremely high regularity has been constructed in the polymer complex 4.

Further, channels P and Q are different from each other in the diameter of an inscribed circle thereof and in the major and minor axes of an inscribed ellipse thereof (channel P: the major axis of the inscribed ellipse, 8.5 to 10.0 Å; the minor axis of the inscribed ellipse, 6.0 to 8.0 Å; and channel Q: the diameter of the inscribed circle, 4.5 to 7.0 Å).

As described above, the channels P and Q formed in the polymer complex 4 having a single-crystal structure represented by $\{[(ZnI_2)_3(C)_2(D_4)]$ (nitrobenzene)$_4$(methanol)$_n\}_z$ (n, z: nonstoichiometric composition)) are different from each other in 3 aspects that are shape, size and atmosphere, and also in that the hydroxy group of 1-hydroxytriphenylene is orientated toward the inner face of channel P only.

Figure 3:
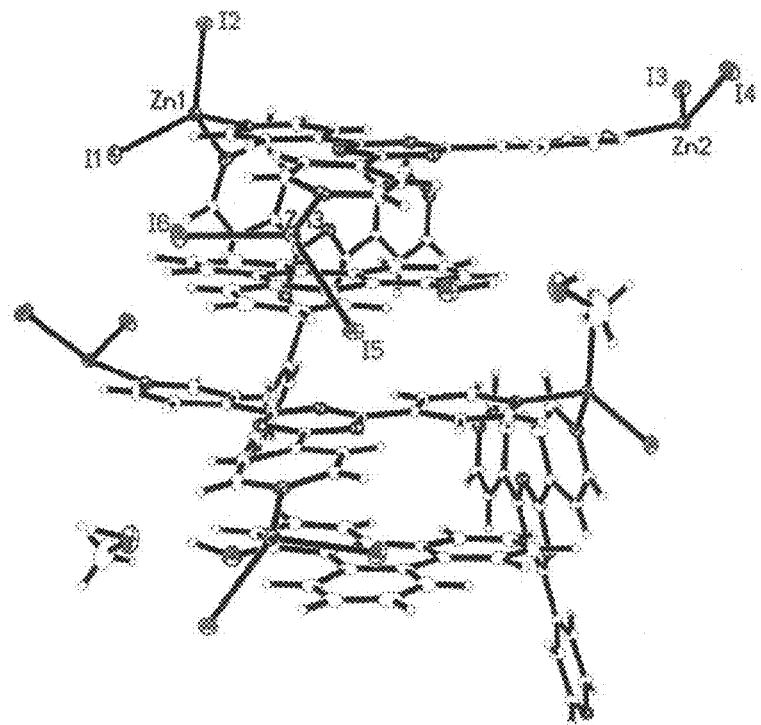
FIG. 3 is a view showing a molecular orientation of tris(4-pyridyl)triazine, 1-hydroxytriphenylene and zinc iodide in a three-dimensional lattice-like structure of the polymer complex 4 and the orientation of methanol included in channel P.
Figure 3:
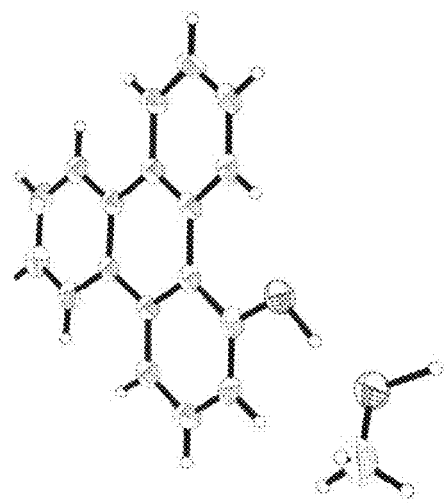

X-ray crystal structure analysis indicates that the channel P in the polymer complex 4 includes methanol in the vicinity of the hydroxy group of 1-hydroxytriphenylene and also includes nitrobenzene so as to fill spaces. On the other hand, the channel Q includes nitrobenzene only. Hydrogen of the hydroxy group of 1-hydroxytriphenylene, which is oriented toward the inner face of the channel P, has also been confirmed by X-ray crystal structure analysis (see FIG. 3; FIG. 3B is a magnification of FIG. 3A). It has also been confirmed that hydrogen of the hydroxy group of 1-hydroxytriphenylene is also directed toward methanol.

Figure 4:
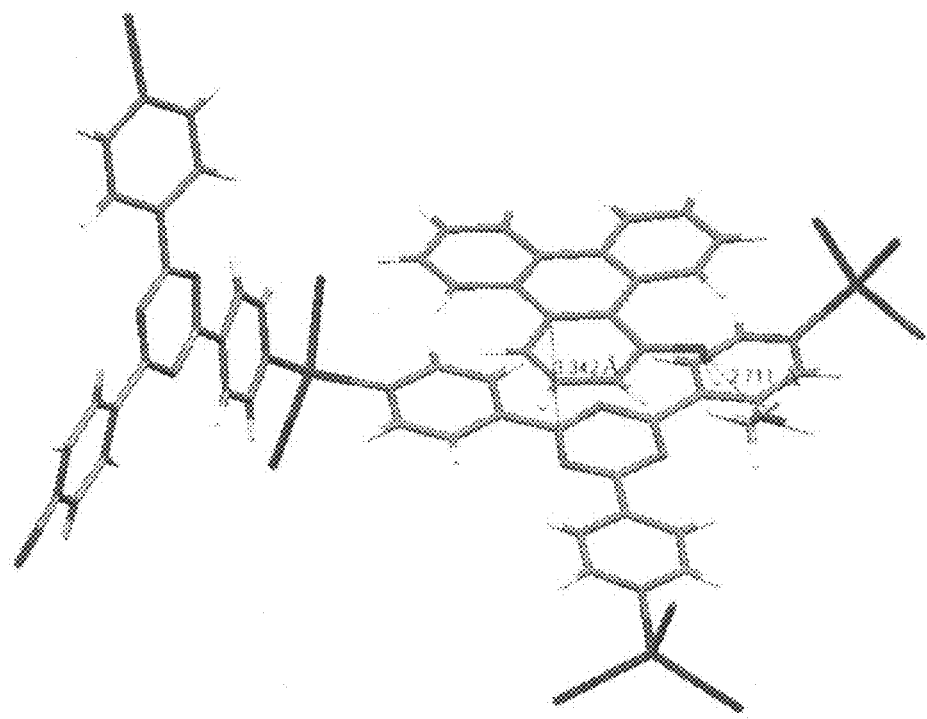
FIG. 4 is a view which shows a molecular orientation of tris(4-pyridyl)triazine, 1-hydroxytriphenylene and zinc iodide in a three-dimensional lattice-like structure of the polymer complex 4 and the orientation of methanol included in channel P, and which shows the stacking distance between tris(4-pyridyl)triazine and 1-hydroxytriphenylene and the distance between an oxygen atom of methanol and an oxygen atom of 1-hydroxytriphenylene.
Figure 4:
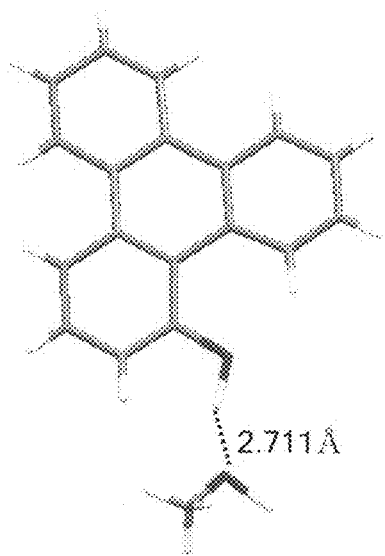

At this time, the distance between an oxygen atom of the hydroxy group of 1-hydroxytriphenylene, and an oxygen atom of methanol included in channel P, is 2.711 Å, that is, the distance is near and thus a strong hydrogen bonding is estimated to be formed between the methanol and the hydroxy group (see FIG. 4; FIG. 4B is a magnification of FIG. 4A). The (shortest) stacking distance between tris(4-pyridyl)triazine [aromatic compound ligand] and 1-hydroxytriphenylene [uncoordinating aromatic compound] in the stack structure is 3.342 Å that is shorter than the atomic distance (3.5 Å) ascribed to van der Waals' force, thus revealing that the interaction between tris(4-pyridyl)triazine as the aromatic compound ligand and 1-hydroxytriphenylene as the uncoordinating aromatic compound is a π-π interaction, that is, an interaction not attributable to van der Waals' force.

In addition, calculation predicted efficient overlap between the HOMO (highest occupied molecular orbital) of 1-hydroxytriphenylene ($D_4$) and the LUMO (lowest unoccupied molecular orbital) of tris(4-pyridyl)triazine (C) (see FIG. 6).

The polymer complex which is a subject of a chemical modification of the present invention represented by the polymer complex 4 described above has, in one molecule thereof, two or more kinds of channel groups different from one another in their affinity for guest molecules and will, upon contacting with a mixture, permit two or more guest molecules in the mixture to be included via guest exchange in different channel groups respectively. The guest molecules incorporated into these channel groups are separated from one another by a rigid main framework of the three-dimensional lattice-like structure. Accordingly, the polymer complex of the present invention enables two or more components that cannot coexist (for example, an acid/base or an oxidizing agent/reducing agent) to be stored in a stable state in one polymer complex or to be transported separately in the polymer complex.

Further, the polymer complex has two or more kinds of channel groups different in their affinity for guest molecules, so that when the channel space of the channel group in the polymer complex is utilized as a reaction field, the reaction field can be accurately regulated by regulation of characteristics of the channel to realize high-degree of regulation of a chemical reaction. For example, a specific catalyst component can be included in a specific channel group, or different catalyst components can be included in two or more kinds of channel groups. When the channel space of the channel group is utilized as a reaction field, reaction materials are introduced into a specific channel group where a channel atmosphere unique to the channel group can be utilized to achieve highly selective material exchange.

The chemical modification method of the present invention is a method for chemically modifying the inner surfaces of channels formed in the polymer complex described above. By allowing the substituent A oriented toward the inside of a channel to convert to a substituent A' without changing a structure of the polymer complex, various functions can be imparted to the polymer complex. The various functions include, for example, regulation and expansion of inclusion characteristics of the polymer complex due to conversion of the substituent A. The conversion of the substituent A causes the change in interaction with a guest molecule, and the change in size and shape of channels or the like, thus, such a polymer complex can exhibit inclusion behavior different from that of the polymer complex having the substituent A.

The inventors of the present invention have found that by dipping a polymer complex, which is obtained by using tris(4-pyridyl)triazine (C) as the aromatic compound ligand, 1-aminotriphenylene ($D_1$) as the uncoordinating aromatic compound and $ZnI_2$ as a metal compound containing a metal ion as the central atom, in a solution containing an aldehyde compound such as salicylaldehyde, acetalldehyde ($CH_3CHO$) etc., an amino group bound to triphenylene in the polymer complex is converted to an imino group represented by —N=Q1 while the polymer complex maintains the three-dimensional structure thereof (see Formulae 7 and 8).

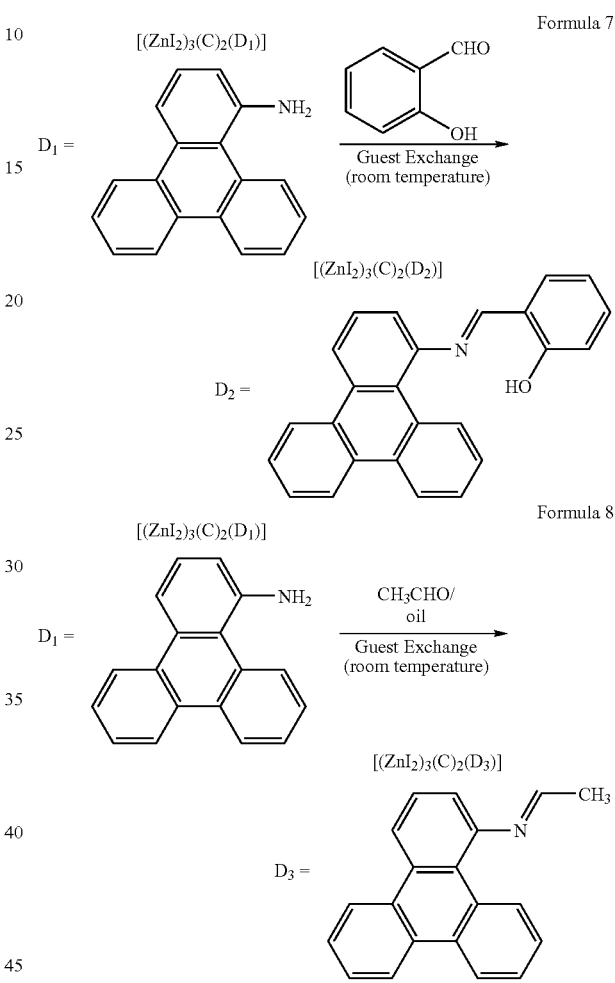

That is, the chemical modification method of the present invention is a method wherein after forming the polymer complex described above, the substituent A oriented toward the inner surface of a channel of channel group B in the polymer complex is reacted with a guest molecule incorporated into the channel of the channel group B to be converted to the substituent A'.

As described above, the polymer complex constructed by using the uncoordinating aromatic compound having substituent A exhibits an inclusion behavior, in which guest molecules are incorporated into channels of the polymer complex. When a guest molecule having reactivity with substituent A is included in a channel in which the substituent A is oriented, the substituent A can be converted to substituent A' by reacting the guest molecule with the substituent A.

"Substituent A converts to substituent A'" as used herein includes the change in part of the structure of the substituent A by a reaction with the guest molecule as well as the replacement of the substituent A as a whole from a part where the substituent A is bound to the uncoordinating aromatic compound.

In Formulae 7 and 8, the amino group of triphenylene being the uncoordinating aromatic compound and the aldehyde compound being a guest molecule causes a dehydration reaction to covert the amino group to a group represented by —N=Q1 (hereinafter it may be referred as group A'i), Q1 representing a divalent organic group.

In Formula 8, triphenylene to which group A'i (N-ethylideneamino group) is introduced is unstable in a normal environment and can be hardly isolated as imine.

However, according to the present invention, an imine having a short carbon chain such as N-ethylideneamino group can be easily introduced to the uncoordinating aromatic compound constituting the polymer complex. It is considered this is because of the following effects: the effect that imine produced by a dehydration reaction of an amino group with aldehyde is sterically protected from reattacking by eliminated water since the imine is located in the vicinity of an inner wall of a channel; and the effect that a side reaction involving a plurality of molecules is suppressed since the above reaction is a single-crystal to single-crystal reaction and thereby molecular motion is reduced to some extent compared to reactions in solution system.

On the other hand, in the reaction of Formula 7, group A'i (salicylideneamino group) is introduced to triphenylene constituting the polymer complex while maintaining the three-dimensional structure of the polymer complex, however, the triphenylene having the salicylideneamino group has coordinating ability owing to a phenolic hydroxyl group and a nitrogen atom thereof. Accordingly, in the case that triphenylene having a salicylideneamino group is used as the uncoordinating aromatic compound upon forming the polymer complex, the triphenylene is coordinated to a metal species. Thus, the above-described polymer complex having the three-dimensional structure in which channels are formed cannot be constructed.

However, in the case of introducing a salicylideneamino group by the chemical modification after forming the polymer complex as the present invention, the salicylideneamino group can be oriented toward the inner surface of a channel without coordinating the salicylideneamino group to a metal species by the contribution of a steric effect of the salicylideneamino group and the crystal to crystal reaction.

As described above, according to the present invention, even a group represented by —N=Q1, which is highly difficult to be introduced to the uncoordinating aromatic compound as substituent A upon forming the polymer complex, can be introduced to the uncoordinating aromatic compound. Herein, Q1 is not particularly limited as long as it is a divalent organic group and may be an aliphatic group or an aromatic group. Q1 may include a heteroatom, a branched structure and/or an unsaturated bond.

Specific examples of Q1 include, for example, an alkyl group having 1 to 5 carbon atoms (it may have a branched structure); a chain hydrocarbon functional group having 1 to 5 carbon atoms with a substituent such as a hydroxy group, a nitro group or an amino group (it may have a branched structure and/or include a hetero atom); and a phenyl group (it may have a substituent such as a hydroxy group, a nitro group and an amino group). When the chain length of Q1 is short as described above, —N=Q1 tends to be highly unstable in a normal environment and can be hardly isolated.

Also, other examples of Q1 include, for example, a chain hydrocarbon functional group having 1 to 5 carbon atoms with a substituent such as a carboxyl group or a nitryl group (it may have a branched structure and/or a heteroatom); a four to twelve membered monocyclic group or a bi- to tetracyclic aromatic group (it may have a condensed structure) having a substituent such as a carboxyl group or a nitryl group; and phenols. In the case of such Q1, —N=Q1 has a possibility of forming a coordinate bonding with a metal species which forms the three-dimensional coordination network of the polymer complex, thus it is difficult to construct the polymer complex in a state that —N=Q1 is preliminarily introduced to the uncoordinating aromatic compound.

That is, the chemical modification method of the present invention is a method utilizing a selective incorporation of guest molecules by the polymer complex and characteristics of channel as a specific reaction field, and is capable of introducing a substituent which is hardly introduced under normal condition to the uncoordinating aromatic compound. Therefore, construction of a channel atmosphere which has been conventionally unfeasible can be realized. It shows that channel environments such as the size, shape and atmosphere of channels can be regulated precisely by the substituent of the uncoordinating aromatic compound.

The salicylideneamino group produced by the reaction of Formula 7 is oriented toward the inner surface of the channel, which is the same as the channel in which the amino group of 1-aminotriphenylene is oriented, while the N-ethylideneamino group produced by the reaction of Formula 8 is oriented toward the inner surface of the channel, which is different from the channel in which the amino group of 1-aminotriphenylene is oriented. The orientational change of such substituents is not elucidated in detail, however, it is considered that triphenylene [uncoordinating aromatic compound] which forms the three-dimensional structure of the polymer complex by stacking with tris(4-pyridyl)triazine [aromatic compound ligand] rotates while maintaining the stacked state, in accordance with the rotation, the substituent (1-salicylidene amino group) introduced to triphenylene also rotates, and thus, the channel being oriented is changed. Accordingly, in the present invention, the orientation of substituent A' converted from substituent A may be the same channel of channel group B in which the substituent A is oriented, or may be a channel of a channel group other than channel group B.

"arrange substituent A' regularly directing to the inside of a channel of channel group B or a channel of a channel group other than channel group B" and "arrange substituent A'i, substituent A'a, substituent A'im or A'c regularly directing to the inside of a specific channel group B'" mean that the substituents A', A'i, A'a, A'im and A'c are substantially arranged regularly directing to the inside of a channel of a specific channel group, and not all of the substituents A', A'i, A'a, A'im and A'c may be arranged directing to the inside of a channel of a specific channel group. That is, there is a substituent which is not oriented only toward the inner surface of a channel of a specific channel group B' but is disordered to the inner surfaces of several kinds of channel groups.

In the reactions of Formulae 7 and 8, aldehydes incorporated into a channel as a guest molecule and an amino group being substituent A causes dehydration condensation, and thus the amino group is converted to imine. However, a form of conversion of the substituent A by the reaction of the substituent A with the guest molecule is not particularly limited. For example, the substituent may be converted by other dehydration condensation reactions such as an acid-base reaction of carboxylic acid with amine or a condensation reaction of carboxylic acid with alcohol. Also, the substituent A may be oxidized or reduced using an oxidant, a reductant or the like as a guest molecule.

Also, by causing an acylation reaction of an amino group (—NH$_2$) being substituent A with acid anhydride (including cyclic acid anhydride) incorporated into a channel as a guest molecule or a nucleophilic addition reaction of an amino group being substituent A to isocyanato incorporated into a channel as a guest molecule, the amino group can be converted to an amido group represented by —NHC(=O)-Q2 (hereinafter, it may be referred as group A'a), Q2 representing a monovalent organic group. Specifically, by a reaction of an amino group being a substituent with acid anhydride being a guest molecule, nitrogen of the amino group and the carbonyl group of the acid anhydride are bound so that the amino group can be acylated [see polymer complexes 5 to 7: Formulae 9 to 11; and polymer complexes 9 to 13: Formulae 13 to 15]. By a nucleophilic addition reaction of an amino group being a substituent to isocyanato being a guest molecule, nitrogen of the amino group and the carbonyl group of isocyanato are bound so that the amino group can be carbamylated [see polymer complex 8: Formula 12; and polymer complex 14: Formula 16].

Particularly, by dipping polymer complex 1', which is obtained by using tris(4-pyridyl)triazine (C) as the aromatic compound ligand, 2-aminotriphenylene ($D_1'$) as the uncoordinating aromatic compound and $ZnI_2$ as a metal compound containing a metal ion as the central atom, in a solution containing cyclic acid anhydride such as succinic anhydride or maleic anhydride, an amino group bound to triphenylene in the polymer complex 1' is converted to amidobutanoic acid or amidobutenoic acid, while the polymer complex 1' maintains the three-dimensional structure thereof (see Formulae 16 and 17 below).

Triphenylene in which amidobutanoic acid or amidobutenoic acid is introduced has coordinating ability owing to the carboxyl group thereof. Accordingly, in the case that triphenylene having an amidobutanoic acid group or an amidobutenoic acid group is used as the uncoordinating aromatic compound upon forming the polymer complex, the triphenylene is coordinated to a metal species. Thus, the above-described polymer complex having the three-dimensional structure in which channels are formed cannot be constructed. However, as in the present invention, in the case that an amino group bound to triphenylene is converted to a carboxyl group such as an amidobutanoic acid group or an amidobutenoic acid group by the chemical modification after forming the polymer complex, the carboxyl group can be oriented toward the inner surface of a channel without coordinating the carboxyl group to a metal species by the contribution of the steric effect of the carboxyl group and the crystal to crystal reaction.

Q2 described above is not particularly limited as long as it is a monovalent organic group and may be an aliphatic group or an aromatic group. Q2 may include a heteroatom, a branched structure and/or an unsaturated bond. In addition, it may have a substituent such as a carboxyl group, a nitryl group, a hydroxyl group, a nitro group, an amino group or a carboxy group. In the case of Q2 having a substituent such as a carboxyl group as described above, further a nitryl group etc., —NHC(=O)-Q2 has a possibility of forming a coordinate bonding with a metal species which forms the three-dimensional coordination network of the polymer complex, thus it is difficult to construct the polymer complex in a state that —NHC(=O)-Q2 is preliminarily introduced to the uncoordinating aromatic compound. However, in the present invention, by introducing —NHC(=O)-Q2 after construction of the polymer complex, channel modification by —NHC(=O)-Q2 having the coordinating ability as described above is feasible.

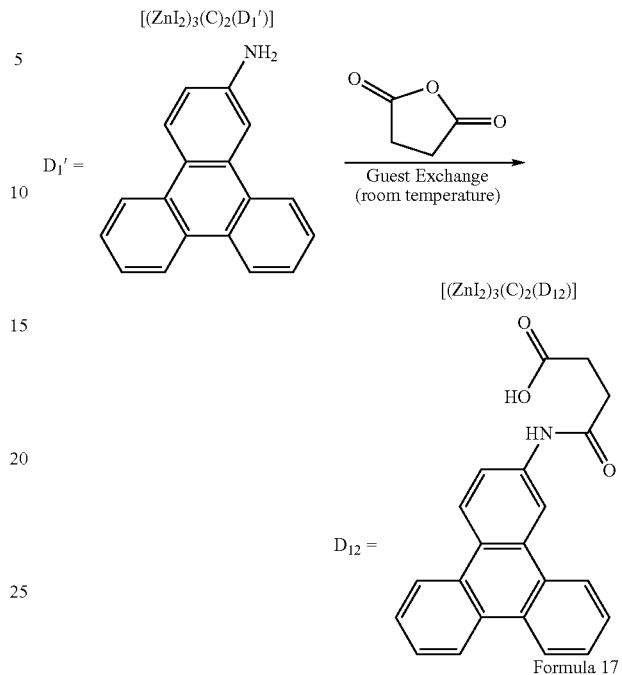

Further, when the uncoordinating aromatic compound has a formyl group (—CHO) as substituent A, the formyl group and an amino compound incorporated into a channel as a guest molecule cause a reaction of dehydration condensation. Thereby, the formyl group can be converted to an imino group represented by —CHN-Q3 (hereinafter, it may be referred as group A'im), Q3 representing a monovalent organic group [see polymer complexes 16 and 17: Formulae 19 and 20 below].

Particularly, by dipping a polymer complex 15, which is obtained by using tris(4-pyridyl)triazine (C) as the aromatic compound ligand, 2-formyl triphenylene ($D_{15}$) as the uncoordinating aromatic compound and $ZnI_2$ as a metal compound containing a metal ion as the central atom, in a solution containing an amino compound containing a carboxyl group such as aminobenzoic acid, a formyl group bound to triphenylene in the polymer complex 15 is converted to aminobenzoic acid, while the polymer complex 15 maintains the three-dimensional structure thereof (see Formula 19 below).

Q3 described above is not particularly limited as long as it is a monovalent organic group and may be an aliphatic group or an aromatic group. Q3 may include a heteroatom, a branched structure and/or an unsaturated bond. In addition, it may have a substituent such as a carboxyl group, a nitryl group, a hydroxyl group, a nitro group or an amino group.

Formula 19

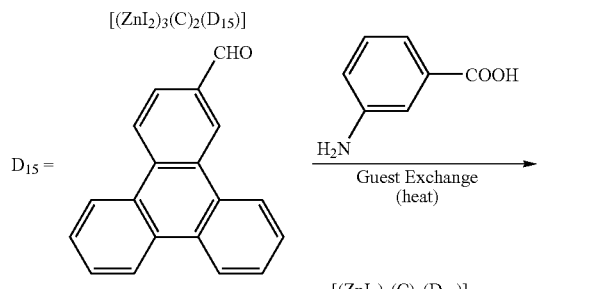

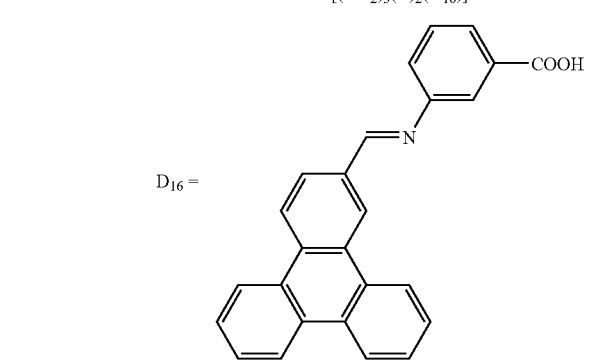

Formula 20

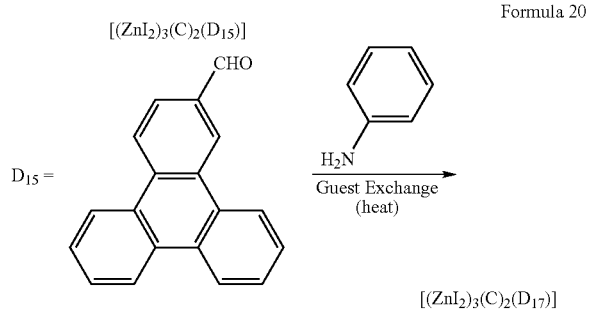

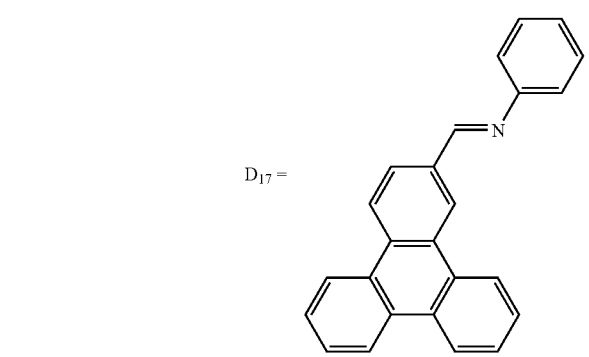

As shown in the above Formulae 16, 17 and 19, when at least one of substituents A such as an amino group and a formyl group is converted to the carboxylic acid group represented by -Q4-COOH group (hereinafter, it may be referred as group A'c), Q4 representing a divalent organic group, such as an amidobutanoic acid group, an amidobutenoic acid group or an aminobenzoic acid group, an anionic functional group such as a carboxyl group is oriented toward the inner surface of a channel. Thus, the polymer complex can hold a cation such as a metal ion or proton in the channel thereof and conduct a cation. That is, it can be expected that the polymer complex is applied for catalyst materials by holding a metal ion in the channel to exhibit catalyst activity, or electrolyte materials by holding lithium ion, proton or the like to exhibit ion conductivity.

Q4 described above is not particularly limited as long as it is a divalent or more organic group and may be an aliphatic group or an aromatic group. Q4 may include a heteroatom, a branched structure and/or an unsaturated bond. In addition, it may have a substituent such as a carboxyl group, a nitryl group, a hydroxyl group, a nitro group or an amino group.

A guest molecule that reacts with substituent A is not limited to one kind, and may be two or more kinds. By the action of two or more kinds of guest molecules among two or more kinds of the guest molecules incorporated into channels of channel group B with substituent A, the substituent A can be converted to substituent A'. Also, a substituent converted by a reaction with a guest molecule is not limited to one kind, and several kinds of substituents can be converted. In this case, the several kinds of substituents include substituents having different chemical structures as well as substituents having different introducing positions in the uncoordinating aromatic compound.

A method for converting substituent A to substituent A' by incorporating a guest molecule and reacting the substituent A with the guest molecule is not particularly limited, and firstly a guest molecule is incorporated into a polymer complex. Usually, a guest molecule is naturally included by bringing the guest molecule into contact with a polymer complex.

Examples of a method for including a guest molecule includes a method of dipping a polymer complex in a solution containing guest molecules or in guest molecules themselves, and a method of bringing a polymer complex into contact with steam of guest molecules. As the need arises, by regulating the concentration, temperature, pressure of guest molecules or the like, the inclusion rate of guest molecules into channels can be adjusted. The contact time of a solution containing guest molecules, guest molecules themselves in the state of solution, or guest molecules themselves in the state of gas with a polymer complex, the concentration of guest molecules in the solution or the like is not particularly limited, and may be appropriately determined.

The reaction of a guest molecule incorporated into a channel with substituent A may be naturally progressed. The reaction rate can be accelerated by heating or increasing the concentration of guest molecules in a guest molecule solution to be contacted with a polymer complex. Also, in the case that the reaction is not progressed selectively or the three-dimensional structure of the polymer complex collapses since the reaction rate is too fast, the reaction rate can be reduced by means such as cooling, reducing the concentration of guest molecules in a guest molecule solution, or using a solvent having high viscosity. Thereby, the reaction can be selectively progressed and the three-dimensional structure of the polymer complex can be maintained.

The chemical modification of the present invention is performed by the reaction of a guest molecule with substituent A oriented toward a channel in which the guest molecule is incorporated. Since incorporation of guest molecules is selective and the guest molecules incorporated into channels exists in very high density, the amount of guest molecules used for modifying inner surfaces of channels of the polymer complex is very small. That is, inner surfaces of channels can be chemically modified efficiently by using a small amount of reagent, therefore, the present invention is a method which is environmentally-friendly and low-cost.

EXAMPLES

Hereinafter, the present invention is described in more detail by reference to Examples.

(Production of Polymer Complex 1)

4 ml of nitrobenzene and 1 ml of methanol were placed in a test tube, and 6.3 mg (0.02 mmol) of 2,4,6-tris(4-pyridyl)-1,3,5-triazine (C) was dissolved therein, and 1-aminotriphenylene ($D_1$) was added thereto.

Then, the solution obtained above was used as a bottom layer, and 0.5 ml of methanol as a buffer was added quietly as a middle layer thereon. Finally, a solution of 9.6 mg (0.03 mmol) $ZnI_2$ in 0.5 ml methanol was added quietly as a top layer, left at about 23 to 25° C. (room temperature) for about 3 days to give a polymer complex 1 [$(ZnI_2)_3(C)_2(D_1)$].

(Analysis of Polymer Complex 1)

Figure 10:
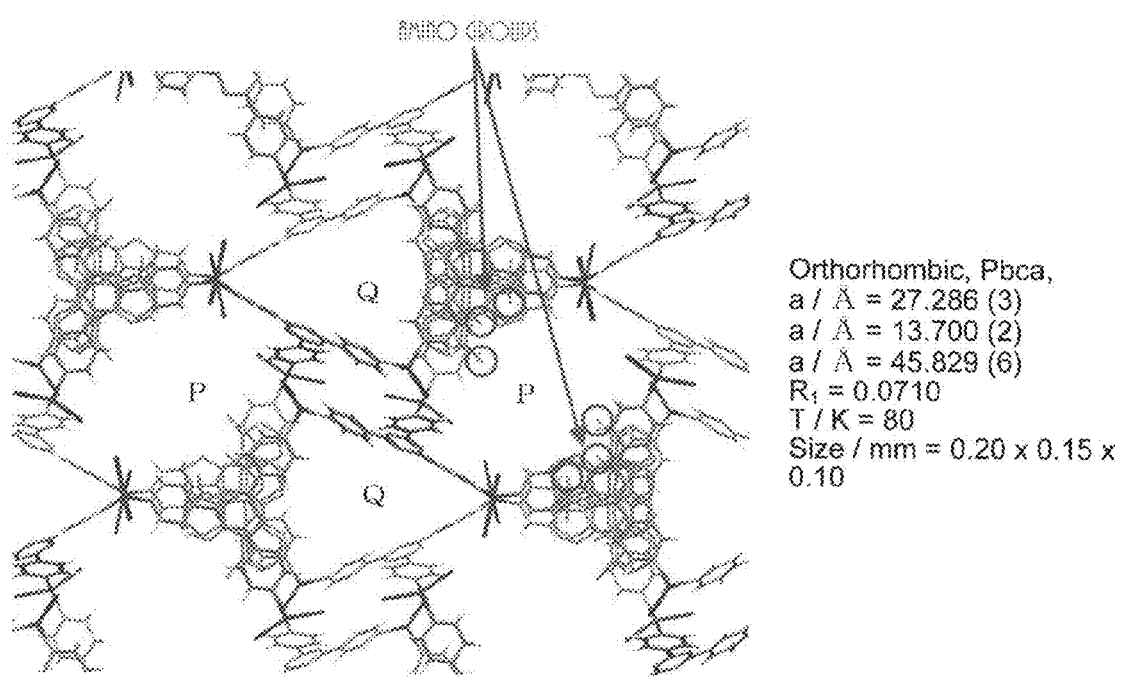
FIG. 10 is a view showing a crystal structure of the polymer complex 1.

The resulting polymer complex 1 was analyzed for its X-ray crystal structure. The results are shown in FIG. 10. FIG. 10 with an axis b in a direction perpendicular to the plane of this figure (crystal 010 plane) shows an interpenetrated structure in the three-dimensional lattice-like structure of the polymer complex 1 along the direction (axis b) in which channels P and Q extend. In FIG. 10, guest molecules incorporated into channels P and Q are not shown.

The polymer complex 1 has two kinds of channels (P and Q) each arranged regularly between stack structures of tris(4-pyridyl)triazine (C) and 1-aminotriphenylene ($D_1$) which are formed in a three-dimensional lattice-like structure constructed by tris(4-pyridyl)triazine (C) and zinc iodide.

The channel P is almost cylindrical and mainly surrounded by hydrogen atoms on the edge of the π-plane of infinitely stacked tris(4-pyridyl)triazine (C) and 1-aminotriphenylene ($D_1$). The amino group of 1-aminotriphenylene ($D_1$) is oriented (disordered) to the inside of channel P to form a part of the inner surface of channel P.

On the other hand, channel Q is in the form of a pseudo-triangular prism, where two of the three walls forming the triangular prism are surrounded by the π-plane of tris(4-pyridyl)triazine (C), and the third is surrounded by hydrogen atoms on the edge of the π-plane of infinitely stacked tris(4-pyridyl)triazine (C) and 1-aminotriphenylene ($D_1$). The amino group of 1-aminotriphenylene ($D_1$) is not oriented to the inside of channel Q.

[Chemical Modification of Inner Surfaces of Channels of Polymer Complex 1]

The polymer complexes 1 synthesized as described above were respectively dipped in an aldehyde compound (salicylaldehyde or formaldehyde), thereby, 1-aminotriphenylene and the aldehyde compound caused a dehydration reaction in the single crystal of the polymer complex 1 to synthesize polymer complexes 2 and 3 having imine in the framework as shown below.

Similarly, the polymer complexes 1 were respectively dipped in acid anhydride (acetic anhydride, propanoic anhydride, or octanoic anhydride), thereby, 1-aminotriphenylene and the acid anhydride caused a reaction in the single crystal of the polymer complex 1 to synthesize polymer complexes 5 to 7 having amide in the framework.

Also, the polymer complex 1 was dipped in isocyanato (phenyl isocyanate), thereby, 1-aminotriphenylene and the isocyanato caused a reaction in the single crystal of the polymer complex 1 to synthesize a polymer complex 8 having amide (urea derivative) in the framework.

(Production of Polymer Complex 2)

By dipping the polymer complex 1 in salicylaldehyde at room temperature for two weeks, 1-aminotriphenylene ($D_1$) constituting the polymer complex 1 and salicylaldehyde incorporated into channels as the guest molecule of the polymer complex 1 caused a dehydration reaction to give a polymer complex 2 [$(ZnI_2)_3(O)_2(D_2)$] being a yellow crystal.

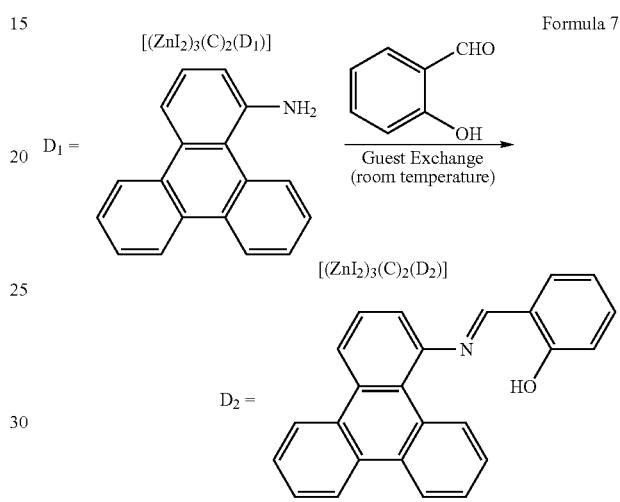

Formula 7

(Analysis of Polymer Complex 2)

Figure 8:
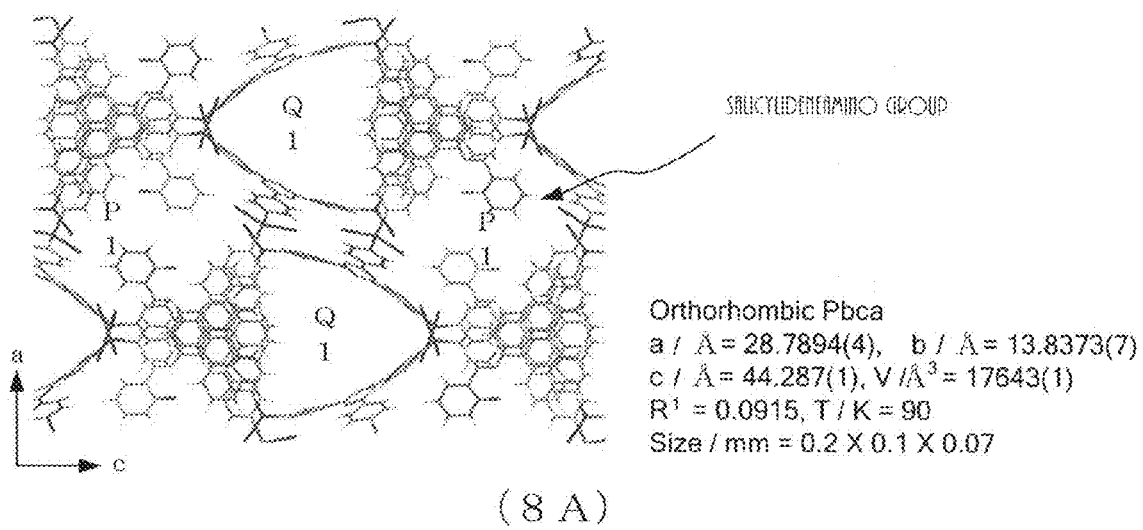
FIG. 8 is a view showing a crystal structure of the polymer complex 2 (FIG. 8A) and 1-salicylidene aminotriphenylene in the polymer complex 2 (8B).
Figure 8:
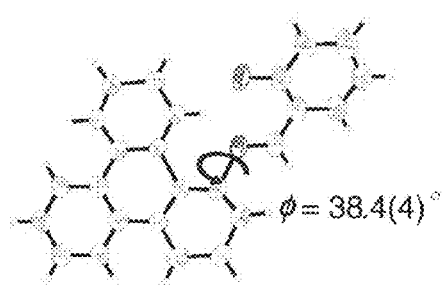

The resulting polymer complex 2 was analyzed for its X-ray crystal structure. The results are shown below. FIG. 8 (8A) with an axis b in a direction perpendicular to the plane of this figure (crystal 010 plane) shows an interpenetrated structure in the three-dimensional lattice-like structure of the polymer complex 2 along the direction (axis b) in which channels P1 and Q1 extend. In FIG. 8, guest molecules incorporated into channels P1 and Q1 are not shown.

The polymer complex 2 has a three-dimensional structure as shown in FIG. 8 (8A) and maintains the three-dimensional structure of the polymer complex 1 (see FIG. 10). That is, the polymer complex 2 has two kinds of channels (P1 and Q1) each arranged regularly between stack structures of tris(4-pyridyl)triazine (C) and 1-salicylideneaminotriphenylene ($D_2$) which are formed in a three-dimensional lattice-like structure constructed by tris(4-pyridyl)triazine (C) and zinc iodide.

The channel P1 is almost cylindrical and mainly surrounded by hydrogen atoms on the edge of the π-plane of infinitely stacked tris(4-pyridyl)triazine (C) and 1-salicylideneaminotriphenylene ($D_2$). The salicylideneamino group of 1-salicylideneaminotriphenylene ($D_2$) is oriented toward an inner surface of channel P1 to form a part of the inner surface of channel P1. The salicylideneamino group was observed in a staggered conformation, and its dihedral angle was 38.4 (4)° (see FIG. (8B)).

On the other hand, channel Q1 is in the form of a pseudo-triangular prism, where two of the three walls forming the triangular prism are surrounded by the π-plane of tris(4-pyridyl)triazine (C), and the third is surrounded by hydrogen atoms on the edge of the π-plane of infinitely stacked tris(4-pyridyl)triazine (C) and 1-salicylideneaminotriphenylene ($D_2$). The salicylideneamino group of 1-salicylidene aminotriphenylene ($D_2$) is not oriented toward an inner surface of channel Q1.

(Production of Polymer Complex 3)

By dipping the polymer complex 1 [$(ZnI_2)_3(C)_2(D_1)$] in fluorolube containing acetaldehyde at room temperature for one day, 1-aminotriphenylene ($D_1$) constituting the polymer complex 1 and acetaldehyde incorporated into channels as the guest molecules of the polymer complex 1 caused a dehydration reaction to give a polymer complex 3 [$(ZnI_2)_3(O)_2(D_3)$] being a yellow crystal.

In the reaction shown in Formula 8, an oil (fluorolube) having high viscosity was used as a solvent in order to protect the crystal structure of the polymer complex by decreasing the rate of the guest exchange and the dehydration reaction.

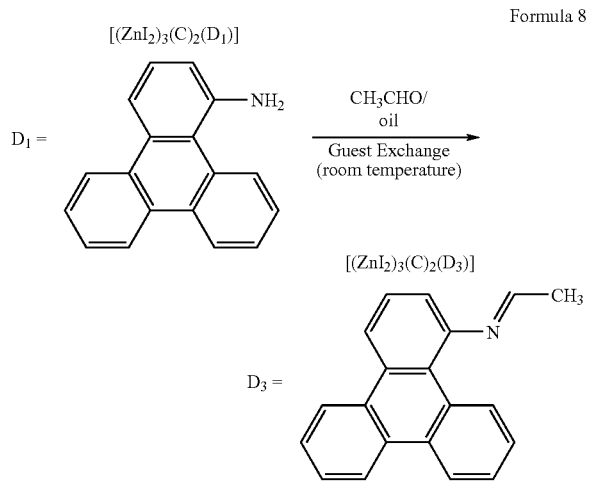

Formula 8

(Analysis of Polymer Complex 3)

Figure 9:
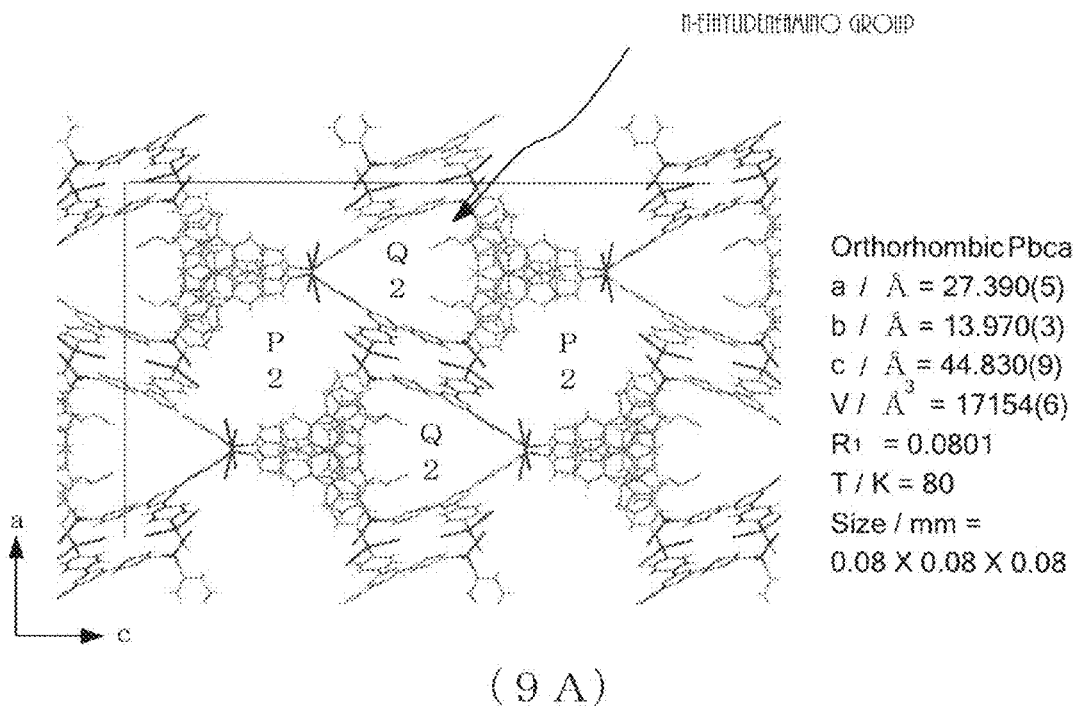
FIG. 9 is a view showing a crystal structure of the polymer complex 3 (FIG. 9A) and 1-N-ethylidene aminotriphenylene in the polymer complex 3 (9B).
Figure 9:
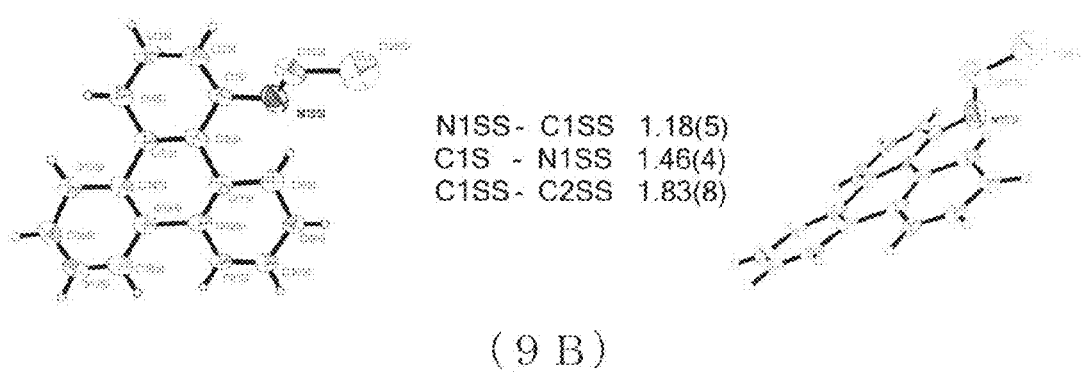

The resulting polymer complex 3 was analyzed for its X-ray crystal structure. The results are shown below. FIG. 9 (9A) with an axis b in a direction perpendicular to the plane of this figure (crystal 010 plane) shows an interpenetrated structure in the three-dimensional lattice-like structure of the polymer complex 3 along the direction (axis b) in which channels P2 and Q2 extend. Also, FIG. 9 (9B) shows 1-N-ethylideneaminotriphenylene ($D_3$) in the polymer complex 3. In FIG. 9, guest molecules incorporated into channels P2 and Q2 are not shown.

The polymer complex 3 has a three-dimensional structure as shown in FIG. 9 (9A) and maintains the three-dimensional structure of the polymer complex 1 (see FIG. 10). That is, the polymer complex 3 has two kinds of channels (P2 and Q2) each arranged regularly between stack structures of tris(4-pyridyl)triazine (C) and 1-N-ethylideneaminotriphenylene ($D_3$) which are formed in a three-dimensional lattice-like structure constructed by tris(4-pyridyl)triazine (C) and zinc iodide. The channel P2 is almost cylindrical and mainly surrounded by hydrogen atoms on the edge of the π-plane of infinitely stacked tris(4-pyridyl)triazine (C) and 1-N-ethylideneaminotriphenylene ($D_3$). The N-ethylideneamino group of 1-N-ethylideneaminotriphenylene ($D_3$) is not oriented toward an inner surface of channel P2.

On the other hand, channel Q2 is in the form of a pseudo-triangular prism, where two of the three walls forming the triangular prism are surrounded by the π-plane of tris(4-pyridyl)triazine (C), and the third is surrounded by hydrogen atoms on the edge of the π-plane of infinitely stacked tris(4-pyridyl)triazine (C) and 1-N-ethylideneaminotriphenylene ($D_3$). The N-ethylideneamino group of 1-N-ethylideneaminotriphenylene ($D_3$) is oriented toward an inner surface of channel Q2 to form a part of the inner surface of channel Q2. The distance between nitrogen and carbon of N-ethylideneamino group (N1SS-C1SS) was 1.18 (5)Å (see FIG. 9 (9B)) and was equivalent to a value of double bond. Thereby, it was confirmed that imine was produced in the crystal.

In the polymer complex 3, before the guest exchange of acetaldehyde, the amino group which is the precursor of the N-ethylideneamino group was oriented toward the inner surface of channel P. However, after the guest exchange of acetaldehyde, the N-ethylideneamino group produced by the dehydration reaction of the amino group with acetaldehyde was oriented toward the inner surface of channel Q2. This result suggests that 1-aminotriphenylene of the polymer complex 1 can rotate to change positions of functional groups in channels. Triphenylene is kept in the polymer complex due to π-π stacking with tris(4-pyridyl)triazine, however, a chemical bond is not formed. Therefore, even if triphenylene rotates in a plane, the three-dimensional structure of the polymer complex can be maintained.

(Production of Polymer Complexes 5 to 7)

<Polymer Complex 5>

By dipping the polymer complex 1 in a cyclohexane solution of acetic anhydride (acetic anhydride: cyclohexane=1:29 (volume ratio)) at room temperature for one to two days, 1-aminotriphenylene ($D_1$) constituting the polymer complex 1 and acetic anhydride incorporated into channels as the guest molecule of the polymer complex 1 caused an acylation reaction to give a polymer complex 5 [$ZnI_2)_3(C)_2(D_5)$] being a yellow crystal (see Formula 9 below).

<Polymer Complex 6>

By dipping the polymer complex 1 in a cyclohexane solution of propionic anhydride (propionic anhydride:cyclohexane=1:29 (volume ratio)) at room temperature for two to three days, 1-aminotriphenylene ($D_1$) constituting the polymer complex 1 and propionic anhydride incorporated into channels as the guest molecule of the polymer complex 1 caused an acylation reaction to give a polymer complex 6 [$(ZnI_2)_3(C)_2(D_6)$] being a yellow crystal (see Formula 10 below).

<Polymer Complex 7>

By dipping the polymer complex 1 in a cyclohexane solution of octanoic anhydride (octanoic anhydride: cyclohexane=1:1 (volume ratio)) at room temperature for three to four weeks, 1-aminotriphenylene ($D_1$) constituting the polymer complex 1 and octanoic anhydride incorporated into channels as the guest molecule of the polymer complex 1 caused an acylation reaction to give a polymer complex 7 [$(ZnI_2)_3 (C)_2 (D_7)$] being a yellow crystal (see the following Formula 11).

Formula 9

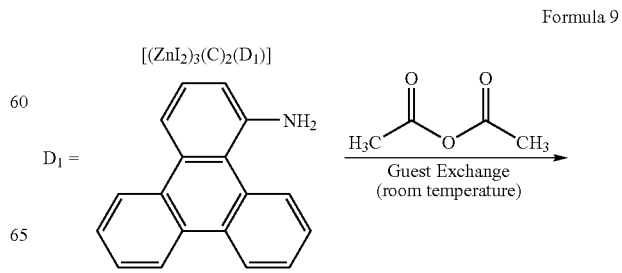

-continued

[(ZnI$_2$)$_3$(C)$_2$(D$_5$)]

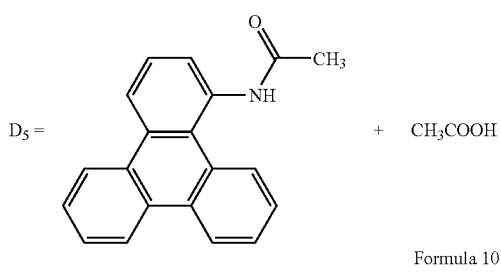

Formula 10

[(ZnI$_2$)$_3$(C)$_2$(D$_1$)]

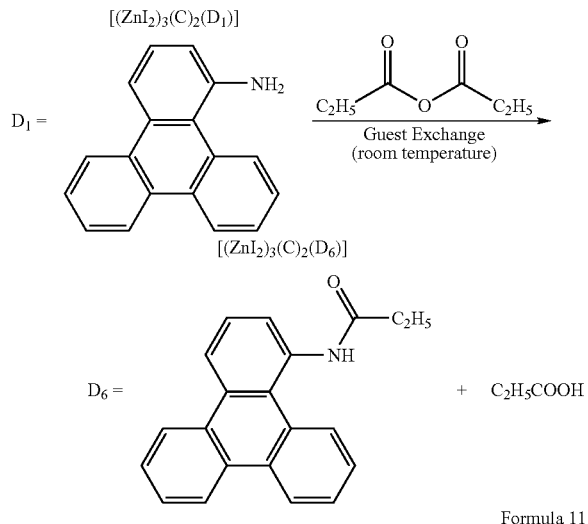

[(ZnI$_2$)$_3$(C)$_2$(D$_1$)]

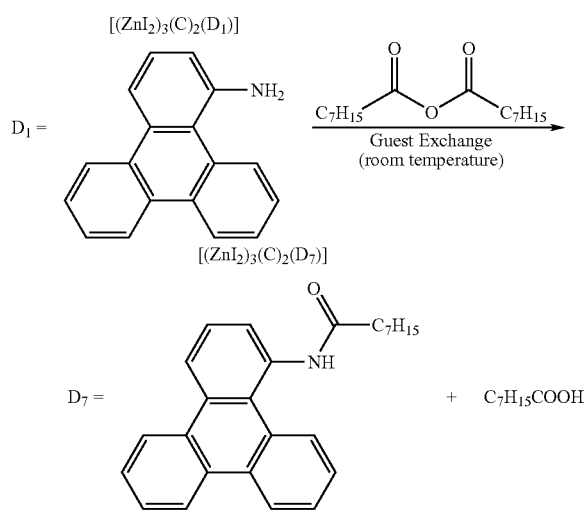

(Analysis of Polymer Complexes 5 to 7)

Figure 11:
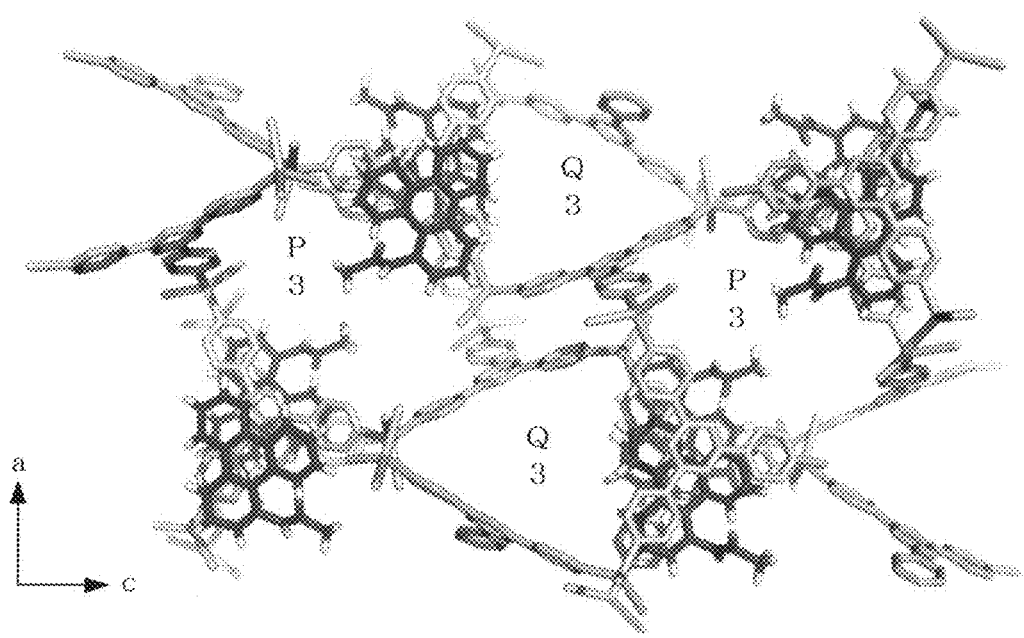
FIG. 11 is a view showing a crystal structure of the polymer complex 5.

The resulting polymer complexes 5 to 7 were analyzed for their X-ray crystal structures. FIG. 11 with an axis b in a direction perpendicular to the plane of this figure (crystal 010 plane) shows an interpenetrated structure in the three-dimensional lattice-like structure of the polymer complex 5 along the direction (axis b) in which channels P3 and Q3 extend. In FIG. 11, guest molecules incorporated into channels P3 and Q3 are not shown.

The polymer complexes 5 to 7 maintain the three-dimensional structure of the polymer complex 1 (see FIG. 10) and have a three-dimensional structure as shown in FIG. 11. Herein, only the three-dimensional structure of the polymer complex 5 is shown in FIG. 11 as a representative, however, the polymer complexes 6 and 7 also have a similar three-dimensional structure. That is, the polymer complexes 5 to 7 have two kinds of channels (P3 and Q3) each arranged regularly between stack structures of tris(4-pyridyl)triazine (C) and 1-triphenyleneamide (D$_6$, D$_6$ and D$_7$) [polymer complex 5: 1-(acetylamino)triphenylene (D$_5$); polymer complex 6: 1-(propionylamino)triphenylene (D$_6$); and polymer complex 7: 1-(octanoylamino)triphenylene (D$_7$)] which are formed in a three-dimensional lattice-like structure constructed by tris(4-pyridyl)triazine (C) and zinc iodide.

The channel P3 is almost cylindrical and mainly surrounded by hydrogen atoms on the edge of the π-plane of infinitely stacked tris(4-pyridyl)triazine (C) and 1-triphenyleneamide (D$_5$, D$_6$ and D$_7$). The amide group of 1-triphenyleneamide (D$_5$, D$_6$ and D$_7$) is oriented toward an inner surface of channel P3 to form a part of the inner surface of channel P3.

On the other hand, channel Q3 is in the form of a pseudo-triangular prism, where two of the three walls forming the triangular prism are surrounded by the π-plane of tris(4-pyridyl)triazine (C), and the third is surrounded by hydrogen atoms on the edge of the π-plane of infinitely stacked tris(4-pyridyl)triazine (C) and 1-triphenyleneamide (D$_5$, D$_6$ and D$_7$). The amide group of 1-triphenyleneamide (D$_5$, D$_6$ and D$_7$) is not oriented toward an inner surface of channel Q3.

(Production of Polymer Complex 8)

By dipping the polymer complex 1 in a cyclohexane solution of phenyl isocyanate (phenyl isocyanate: cyclohexane=1:9 (volume ratio)) at room temperature for three to four days, 1-aminotriphenylene (D$_1$) constituting the polymer complex 1 and phenyl isocyanate incorporated into channels as the guest molecule of the polymer complex 1 caused a nucleophilic addition reaction to give a polymer complex 8 [(ZnI$_2$)$_3$(C)$_2$(D$_8$)] being a yellow crystal (see the following Formula 12).

Formula 12

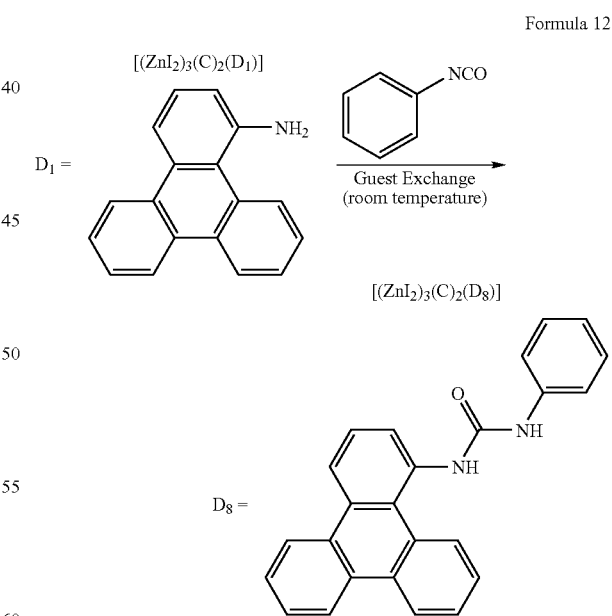

(Analysis of Polymer Complex 8)

Figure 12:
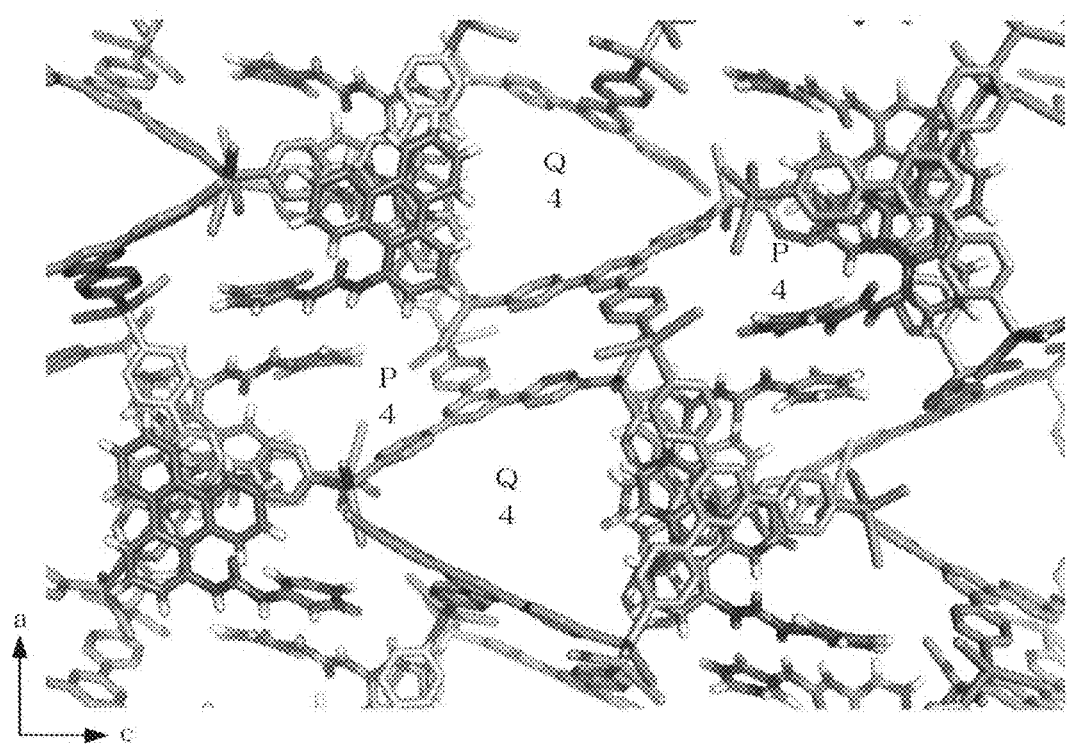
FIG. 12 is a view showing a crystal structure of the polymer complex 8.

The resulting polymer complex 8 was analyzed for its X-ray crystal structure. FIG. 12 with an axis b in a direction perpendicular to the plane of this figure (crystal 010 plane) shows an interpenetrated structure in the three-dimensional lattice-like structure of the polymer complex 8 along the direction (axis b) in which channels P4 and Q4 extend. In FIG. 12, guest molecules incorporated into channels P4 and Q4 are not shown.

The polymer complex 8 maintains the three-dimensional structure of the polymer complex 1 (see FIG. 10) and has a three-dimensional structure as shown in FIG. 12. That is, similarly as the polymer complexes 5 to 7, the polymer complex 8 has two kinds of channels (P4 and Q4) each arranged regularly between stack structures of tris(4-pyridyl)triazine (C) and 1-(3-phenylureido)triphenylene ($D_8$) which are formed in the three-dimensional lattice-like structure constructed by tris(4-pyridyl)triazine (C) and zinc iodide.

The channel P4 is almost cylindrical and mainly surrounded by hydrogen atoms on the edge of the π-plane of infinitely stacked tris(4-pyridyl)triazine (C) and 1-(3-phenylureido)triphenylene ($D_8$). The phenylureido group of 1-(3-phenylureido)triphenylene ($D_8$) is oriented toward an inner surface of channel P4 to form a part of the inner surface of channel P4. On the other hand, channel Q4 is in the form of a pseudo-triangular prism, where two of the three walls forming the triangular prism are surrounded by the π-plane of tris(4-pyridyl)triazine (C), and the third is surrounded by hydrogen atoms on the edge of the π-plane of infinitely stacked tris(4-pyridyl)triazine (C) and 1-(3-phenylureido) triphenylene ($D_8$). The phenylureido group of 1-(3-phenylureido)triphenylene ($D_8$) is not oriented toward an inner surface of channel Q4.

(Production of Polymer Complex 1')

4 ml of nitrobenzene and 1 ml of methanol were placed in a test tube, and 6.3 mg (0.02 mmol) of 2,4,6-tris(4-pyridyl)-1,3,5-triazine (C) was dissolved therein, and 2-aminotriphenylene ($D_1'$) was added thereto.

Then, the solution obtained above was used as a bottom layer, and 0.5 ml of methanol as a buffer was added quietly as a middle layer thereon. Finally, a solution of 9.6 mg (0.03 mmol) $ZnI_2$ in 0.5 ml of methanol was added quietly as a top layer, left at about 23 to 25° C. (room temperature) for about 3 days to give a polymer complex 1' [$(ZnI_2)_3(C)_2(D_1')$].

(Analysis of Polymer Complex 1')

Figure 13:
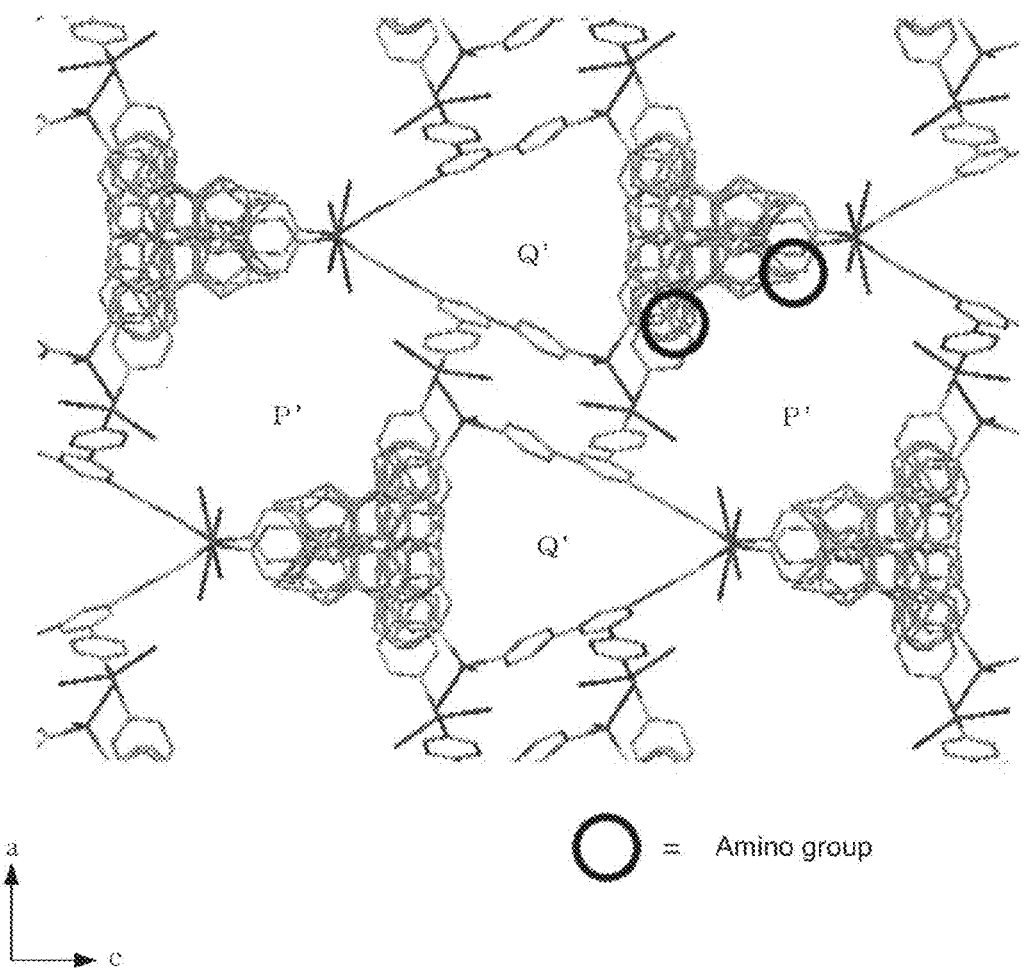
FIG. 13 is a view showing a crystal structure of the polymer complex 1'.

The resulting polymer complex 1' was analyzed for its X-ray crystal structure. The results are shown in FIG. 13. FIG. 13 with an axis b in a direction perpendicular to the plane of this figure (crystal 010 plane) shows an interpenetrated structure in the three-dimensional lattice-like structure of the polymer complex 1' along the direction (axis b) in which channels P' and Q' extend. In FIG. 13, guest molecules incorporated into channels P' and Q' are not shown.

The polymer complex 1' has a similar three-dimensional structure as the polymer complex 1. That is, the polymer complex 1' has two kinds of channels (P' and Q') each arranged regularly between stack structures of tris(4-pyridyl)triazine (C) and 2-aminotriphenylene ($D_1'$) which are formed in a three-dimensional lattice-like structure constructed by tris(4-pyridyl)triazine (C) and zinc iodide.

The channel P' is almost cylindrical and mainly surrounded by hydrogen atoms on the edge of the π-plane of infinitely stacked tris(4-pyridyl)triazine (C) and 2-aminotriphenylene ($D_1'$). The amino group of 2-aminotriphenylene ($D_1'$) is oriented (disordered) to the inside of channel P' to form a part of the inner face of channel P'.

On the other hand, channel Q' is in the form of a pseudo-triangular prism, where two of the three walls forming the triangular prism are surrounded by the π-plane of tris(4-pyridyl)triazine (C), and the third is surrounded by hydrogen atoms on the edge of the π-plane of infinitely stacked tris(4-pyridyl)triazine (C) and 2-aminotriphenylene ($D_1'$). The amino group of 2-aminotriphenylene ($D_1'$) is not oriented toward an inner surface of channel Q'.

[Chemical Modification of Inner Surfaces of Channels of Polymer Complex 1']

The polymer complexes 1' synthesized as described above were respectively dipped in acid anhydride (acetic anhydride, propionic anhydride or octanoic anhydride), thereby, 2-aminotriphenylene and the acid anhydride caused a reaction in the single crystal of the polymer complex 1' to synthesize polymer complexes 9 to 11 having amide in the framework as shown below.

Similarly, the polymer complexes 1' were respectively dipped in cyclic acid anhydride (succinic anhydride or maleic anhydride), thereby, 2-aminotriphenylene and the cyclic acid anhydride caused a reaction in the single crystal of the polymer complex 1' to synthesize polymer complexes 12 and 13 having amide in the framework.

Also, the polymer complex 1' was dipped in isocyanato (phenyl isocyanate), thereby, 2-aminotriphenylene and the isocyanato caused a reaction in the single crystal of the polymer complex 1' to synthesize a polymer complex 14 having amide (urea derivative) in the framework.

(Production of Polymer Complexes 9 to 11)

<Polymer Complex 9>

By dipping the polymer complex 1' in a cyclohexane solution of acetic anhydride (acetic anhydride:cyclohexane=1:29 (volume ratio)) at room temperature for one to two days, 1-aminotriphenylene ($D_1'$) constituting the polymer complex 1' and acetic anhydride incorporated into channels as the guest molecule of the polymer complex 1' caused an acylation reaction to give a polymer complex 9 [$(ZnI_2)_3(C)_2(D_9)$] being a yellow crystal (see Formula 13 below).

<Polymer Complex 10>

By dipping the polymer complex 1' in a cyclohexane solution of propionic anhydride (propionic anhydride: cyclohexane=1:29 (volume ratio)) at room temperature for two to three days, 2-aminotriphenylene ($D_1'$) constituting the polymer complex 1' and propionic anhydride incorporated into channels as the guest molecule of the polymer complex 1' caused an acylation reaction to give a polymer complex [$(ZnI_2)_3(C)_2(D_{10})$] being a yellow crystal (see Formula 14 below).

<Polymer Complex 11>

By dipping the polymer complex 1' in a cyclohexane solution of octanoic anhydride (octanoic anhydride: cyclohexane=1:1 (volume ratio)) at room temperature for three to four weeks, 2-aminotriphenylene ($D_1'$) constituting the polymer complex 1' and octanoic anhydride incorporated into channels as the guest molecule of the polymer complex 1' caused an acylation reaction to give a polymer complex [$(ZnI_2)_3(C)_2(D_{11})$] being a yellow crystal (see the following Formula 15).

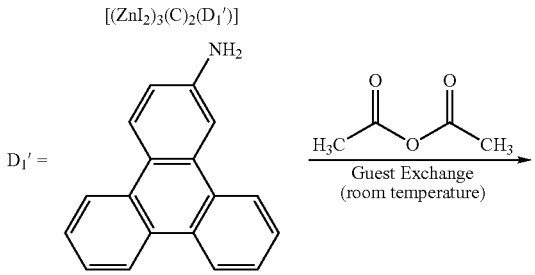

Formula 13

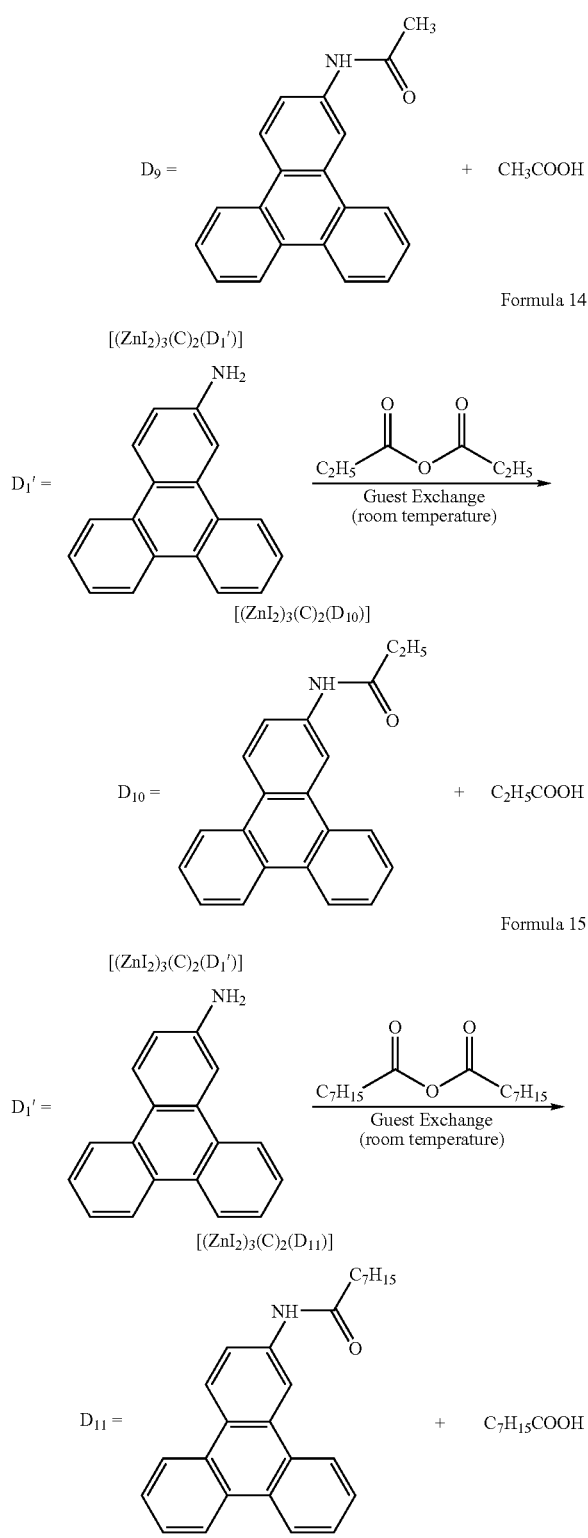

(Analysis of Polymer Complexes 9 to 11)

Figure 14:
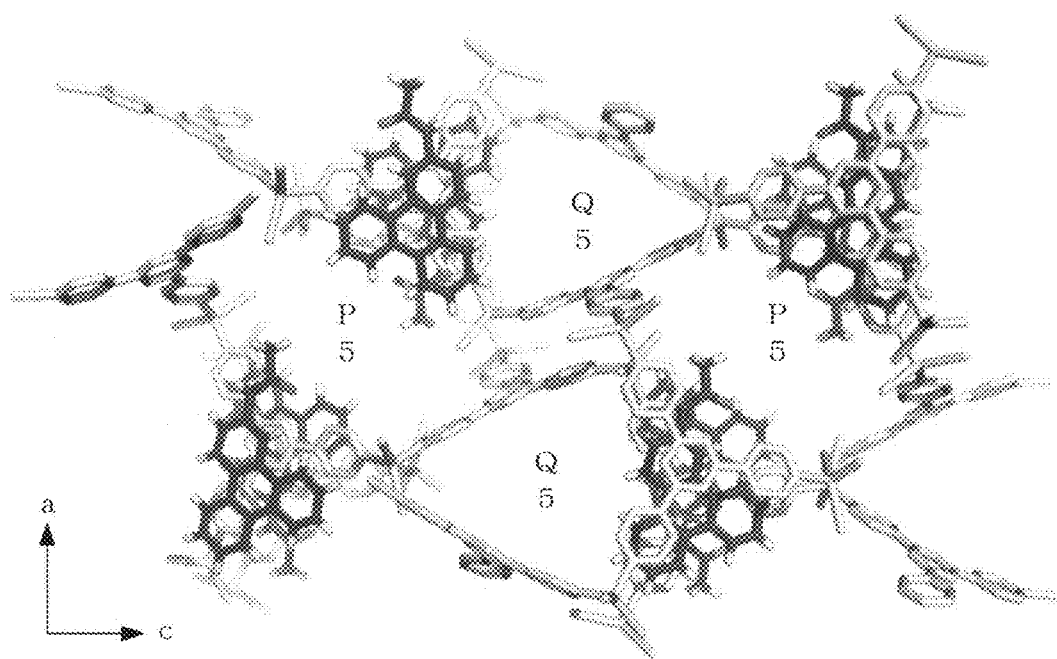
FIG. 14 is a view showing a crystal structure of the polymer complex 9.

The resulting polymer complexes 9 to 11 were analyzed for their X-ray crystal structures. FIG. 14 with an axis b in a direction perpendicular to the plane of this figure (crystal 010 plane) shows an interpenetrated structure in the three-dimensional lattice-like structure of the polymer complex 9 along the direction (axis b) in which channels P5 and Q5 extend. In FIG. 14, guest molecules incorporated into channels P5 and Q5 are not shown.

The polymer complexes 9 to 11 maintain the three-dimensional structure of the polymer complex 1' (see FIG. 13) and have a three-dimensional structure as shown in FIG. 14. Herein, only the three-dimensional structure of the polymer complex 9 is shown in FIG. 14 as a representative, however, the polymer complexes 10 and 11 also have a similar three-dimensional structure. That is, the polymer complexes 9 to 11 have two kinds of channels (P5 and Q5) each arranged regularly between stack structures of tris(4-pyridyl) triazine (C) and 2-triphenyleneamide ($D_9$, $D_{10}$ and $D_{11}$) [polymer complex 9: 2-(acetylamino)triphenylene ($D_9$); polymer complex 10: 2-(propionylamino)triphenylene ($D_{10}$); and polymer complex 11: 2-(octanoylamino)triphenylene ($D_{11}$)] which are formed in a three-dimensional lattice-like structure constructed by tris(4-pyridyl)triazine (C) and zinc iodide.

The channel P5 is almost cylindrical and mainly surrounded by hydrogen atoms on the edge of the π-plane of infinitely stacked tris(4-pyridyl)triazine (C) and 2-triphenylene amide ($D_9$, $D_{10}$ and $D_{11}$). The amide group of 2-triphenylene amide ($D_9$, $D_{10}$ and $D_{11}$) is oriented to the inside of channel P5 to form a part of the inner surface of channel P5.

On the other hand, channel Q5 is in the form of a pseudo-triangular prism, where two of the three walls forming the triangular prism are surrounded by the π-plane of tris(4-pyridyl)triazine (C), and the third is surrounded by hydrogen atoms on the edge of the π-plane of infinitely stacked tris(4-pyridyl)triazine (C) and 2-triphenylene amide ($D_9$, $D_{10}$ and $D_{11}$). The amide group of 2-triphenylene amide ($D_9$, $D_{10}$ and $D_{11}$) is not oriented toward an inner surface of channel Q5.

(Production of polymer complexes 12 to 13)

<Polymer complex 12>

By dipping the polymer complex 1' in an ethyl acetate solution of 10 mM succinic anhydride at room temperature for three to four days, 2-aminotriphenylene (D1') constituting the polymer complex 1' and succinic anhydride incorporated into channels as the guest molecule of the polymer complex 1' caused an acylation reaction to give a polymer complex 12 [$(ZnI_2)_3(C)_2(D_{12})$] being a yellow crystal (see Formula 16 below).

<Polymer complex 13>

Figure 15:
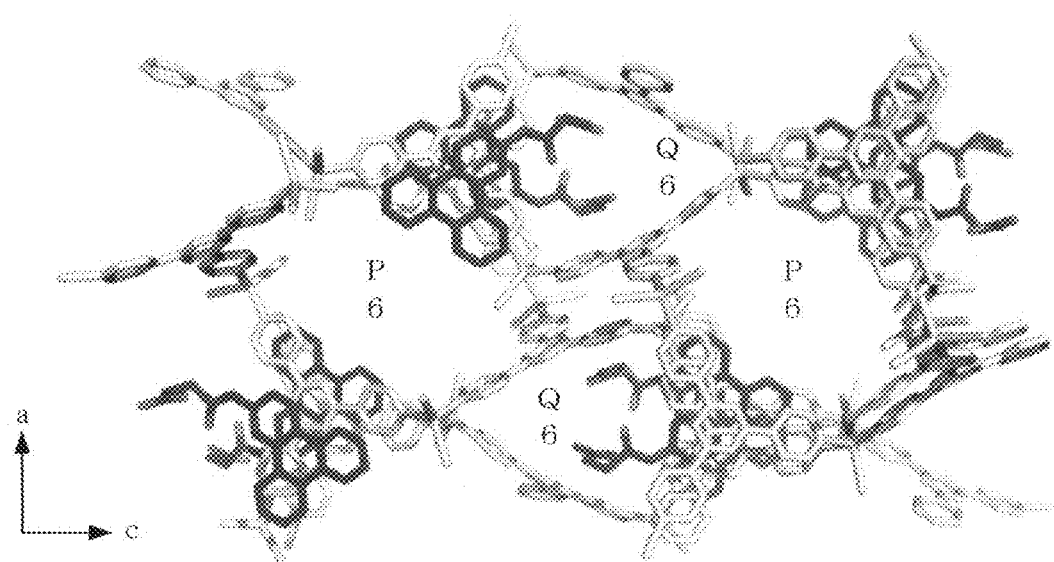
FIG. 15 is a view showing a crystal structure of the polymer complex 12.

By dipping the polymer complex 1' in an ethyl acetate solution of 10 mM maleic anhydride at room temperature for three to four days, 2-aminotriphenylene (D1') constituting the polymer complex 1' and maleic anhydride incorporated into channels as the guest molecule of the polymer complex 1' caused an acylation reaction to give a polymer complex 13 [$(ZnI_2)_3(C)_2(D_{13})$] being a yellow crystal (see the following Formula 17). for their X-ray crystal structures. FIG. 15 with an axis b in a direction perpendicular to the plane of this figure (crystal 010 plane) shows an interpenetrated structure in the three-dimensional lattice-like structure of the polymer complex 12 along the direction (axis b) in which channels P6 and Q6 extend. In FIG. 15, guest molecules incorporated into channels P6 and Q6 are not shown.

The polymer complexes 12 and 13 maintain the three-dimensional structure of the polymer complex 1' (see FIG. 10) and have a three-dimensional structure as shown in FIG. 15. Herein, only the three-dimensional structure of the polymer complex 12 is shown in FIG. 15 as a representative, however, the polymer complex 13 also has a similar three-dimensional structure. That is, the polymer complexes 12 and 13 have two kinds of channels (P6 and Q6) each arranged regularly between stack structures of tris(4-pyridyl)triazine (C) and 2-triphenyleneamide ($D_{12}$ and $D_{13}$) [polymer complex 12: 2-(succinylamino)triphenylene ($D_{12}$); and polymer complex 13: 2-(maleylamino)triphenylene ($D_{13}$)] which are formed in a three-dimensional lattice-like structure constructed by tris(4-pyridyl)triazine (C) and zinc iodide.

The channel P6 is almost cylindrical and mainly surrounded by hydrogen atoms on the edge of the π-plane of infinitely stacked tris(4-pyridyl)triazine (C) and 2-(succinylamino)triphenylene ($D_{12}$) or 2-(maleylamino)triphenylene ($D_{13}$). The carboxyl group of amidobutanoic acid of 2-(succinylamino)triphenylene ($D_{12}$) or amidobutenoic acid of 2-(maleylamino)triphenylene ($D_{13}$) is not oriented toward an inner surface of channel P5 to form a part of the inner surface of channel P5.

On the other hand, channel Q6 is in the form of a pseudo-triangular prism, where two of the three walls forming the triangular prism are surrounded by the π-plane of tris(4-pyridyl)triazine (C), and the third is surrounded by hydrogen atoms on the edge of the π-plane of infinitely stacked tris(4-pyridyl)triazine (C) and Formula 16

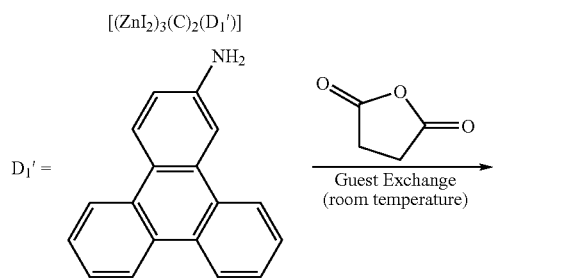

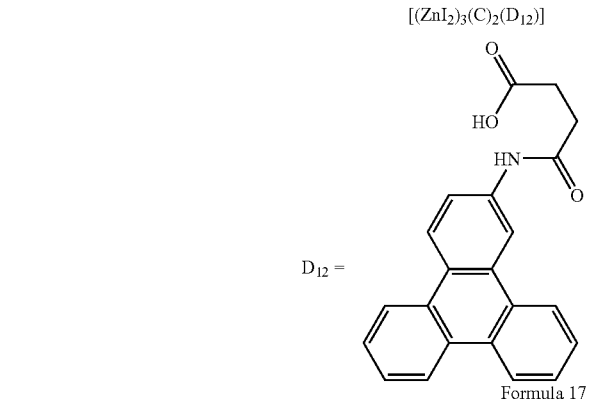

Formula 17

(Analysis of Polymer Complexes 12 and 13)

The resulting polymer complexes 12 and 13 were analyzed 2-(succinylamino)triphenylene ($D_{12}$) or 2-(maleylamino)triphenylene ($D_{13}$). The carboxyl group of amidobutanoic acid of 2-(succinylamino)triphenylene ($D_{12}$) or amidobutenoic acid of 2-(maleylamino)triphenylene ($D_{13}$) is oriented toward an inner surface of channel Q6 to form a part of the inner surface of channel Q6.

Similarly as the polymer complex 3, in the polymer complexes 12 and 13, before the guest exchange of cyclic acid anhydride, the amino group which is the precursor of the amidobutanoic acid group or the amidobutenoic acid group was oriented toward the inner surface of channel P'. However, after the guest exchange of cyclic acid anhydride, the amidobutanoic acid group or the amidobutenoic acid group produced by the amide reaction of the amino group with cyclic acid anhydride was oriented toward the inner surface of channel Q6.

(Production of Polymer Complex 14)

By dipping the polymer complex 1' in a cyclohexane solution of phenyl isocyanate (phenyl isocyanate: cyclohexane=1:9 (volume ratio)) at room temperature for three to four days, 2-aminotriphenylene ($D_1$') constituting the polymer complex 1' and phenyl isocyanate incorporated into channels as the guest molecule of the polymer complex 1' caused a nucleophilic addition reaction to give a polymer complex 14 [$(ZnI_2)_3 (C)_2 (D_{14})$] being a yellow crystal (see the following Formula 18).

Formula 18

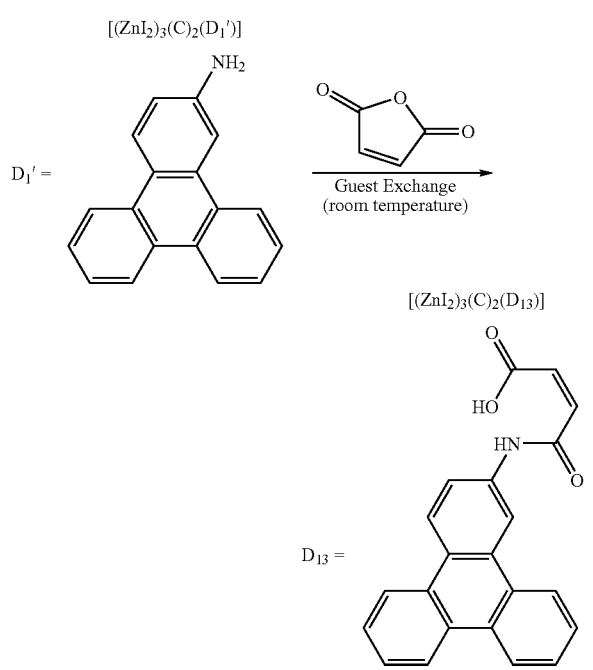

(Analysis of Polymer Complex 14)

Figure 16:
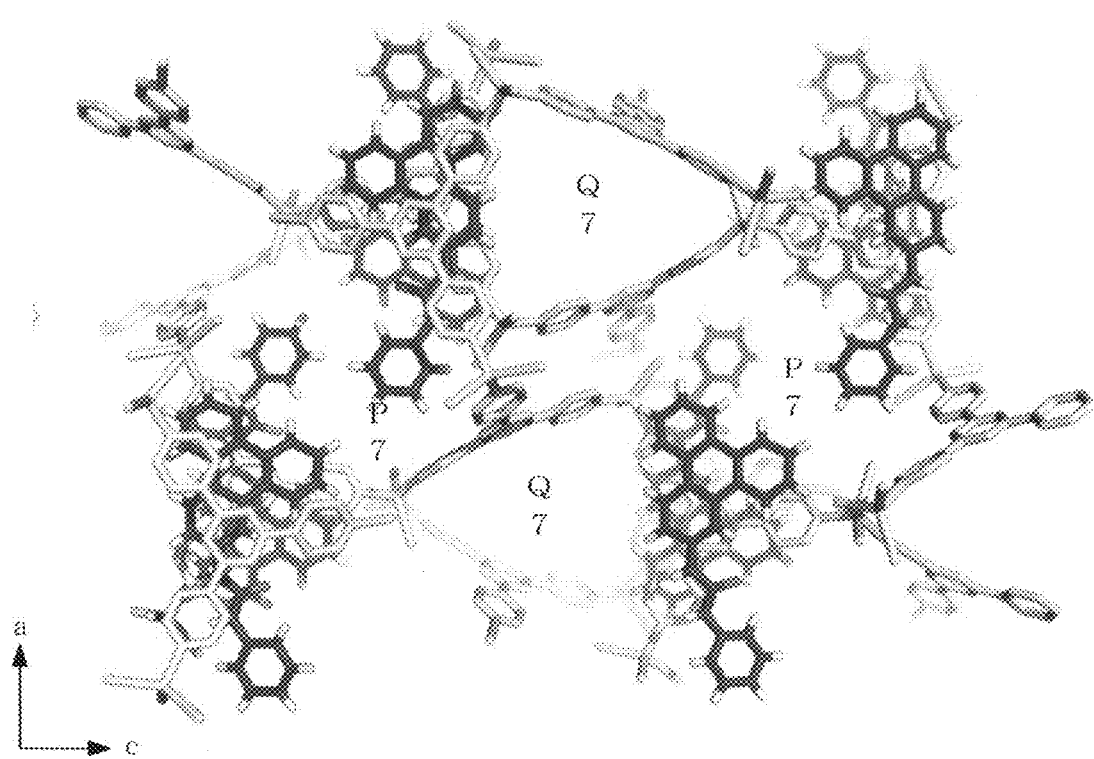
FIG. 16 is a view showing a crystal structure of the polymer complex 14.

The resulting polymer complex 14 was analyzed for its X-ray crystal structure. FIG. 16 with an axis b in a direction perpendicular to the plane of this figure (crystal 010 plane) shows an interpenetrated structure in the three-dimensional lattice-like structure of the polymer complex 14 along the direction (axis b) in which channels P7 and Q7 extend. In FIG. 16, guest molecules incorporated into channels P7 and Q7 are not shown.

The polymer complex 14 maintains the three-dimensional structure of the polymer complex 1' (see FIG. 10) and has a three-dimensional structure as shown in FIG. 16. That is, similarly as the polymer complexes 9 to 11, the polymer complex 14 has two kinds of channels (P7 and Q7) each arranged regularly between stack structures of tris(4-pyridyl)triazine (C) and 2-(3-phenylureido)triphenylene ($D_{14}$) which are formed in a three-dimensional lattice-like structure constructed by tris(4-pyridyl)triazine (C) and zinc iodide.

The channel P7 is almost cylindrical and mainly surrounded by hydrogen atoms on the edge of the π-plane of infinitely stacked tris(4-pyridyl)triazine (C) and 2-(3-phenylureido)triphenylene ($D_{14}$). The phenylureido group of 2-(3-phenylureido)triphenylene ($D_{14}$) is oriented toward an inner surface of channel P7 to form a part of the inner surface of channel P7. On the other hand, channel Q7 is in the form of a pseudo-triangular prism, where two of the three walls forming the triangular prism are surrounded by the π-plane of tris(4-pyridyl)triazine (C), and the third is surrounded by hydrogen atoms on the edge of the π-plane of infinitely stacked tris(4-pyridyl)triazine (C) and 2-(3-phenylureido)triphenylene ($D_{14}$). The phenylureido group of 2-(3-phenylureido)triphenylene ($D_{14}$) is not oriented toward an inner surface of channel Q7.

[Production of Polymer Complex 15]

(Synthesis of 2-formyltriphenylene ($D_{15}$))

2-formyltriphenylene was synthesized with reference to J. Am. Chem. Soc. 1995, 117, 9408, as follows.

Firstly, 0.1 g (0.44 mmol, white powder) of triphenylene was placed in a recovery flask. The inside thereof was vacuated, and then replaced by argon. Next, dehydrated dichloromethane was added to the recovery flask and the flask was cooled to 0° C. (in iced water). While cooling, 1.8 ml (1.8 mmol) of dichloromethane solution of 14% tetrachlorotitanium was added thereto (the solution was changed to an orange colored suspended solution) and 0.4 ml (4.3 mmol) of dichloromethyl methyl ether was further added (the orange colored suspended solution was changed to a purple colored suspended solution).

In order to prevent dichloromethyl methyl ether from decomposing before the reaction, the obtained purple colored suspended solution was agitated for 0.5 hours at 0° C. (in iced water) followed by agitating for 0.5 hours at room temperature. Then, reflux was carried out for 1.5 hours at 50° C., and further agitation was performed for 24 hours at room temperature.

Next, 15 ml of water was added thereto to deactivate tetrachlorotitanium followed by separating organic layers by means of a separating funnel. After rinsing separated organic layers with water, sodium sulfate was added and water in the organic layers was removed. The obtained solution was filtered and the filtered substance therefrom was concentrated and dried to obtain brown powder. The brown powder was purified by column chromatography (using silica and chloroform) to obtain orange colored powder (yield: 0.086 g, 76%).

Figure 17:
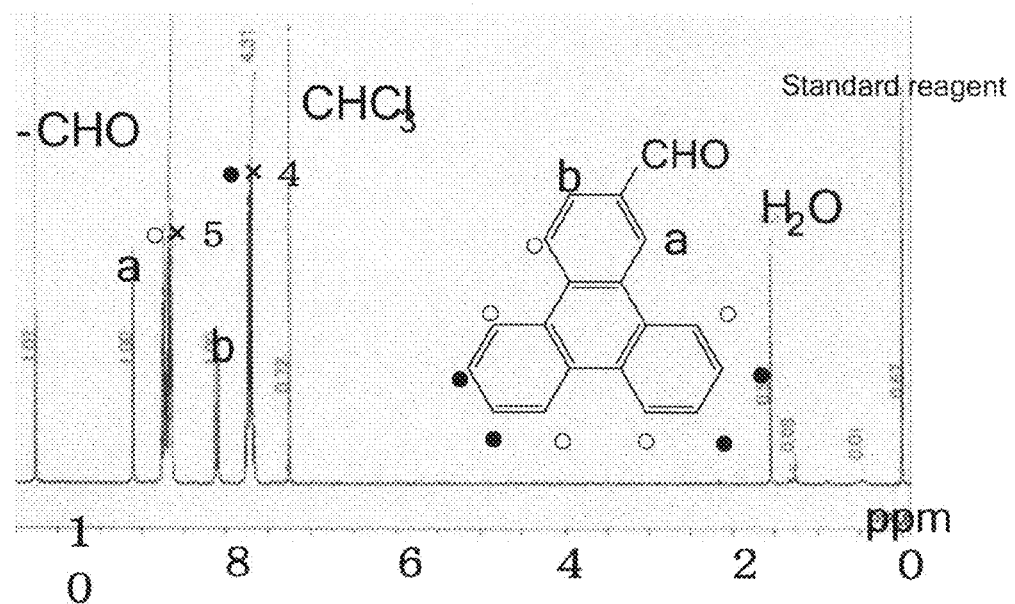
FIG. 17 is a view showing a $^1$HNMR measurement result of 2-formyltriphenylene.
Figure 18:
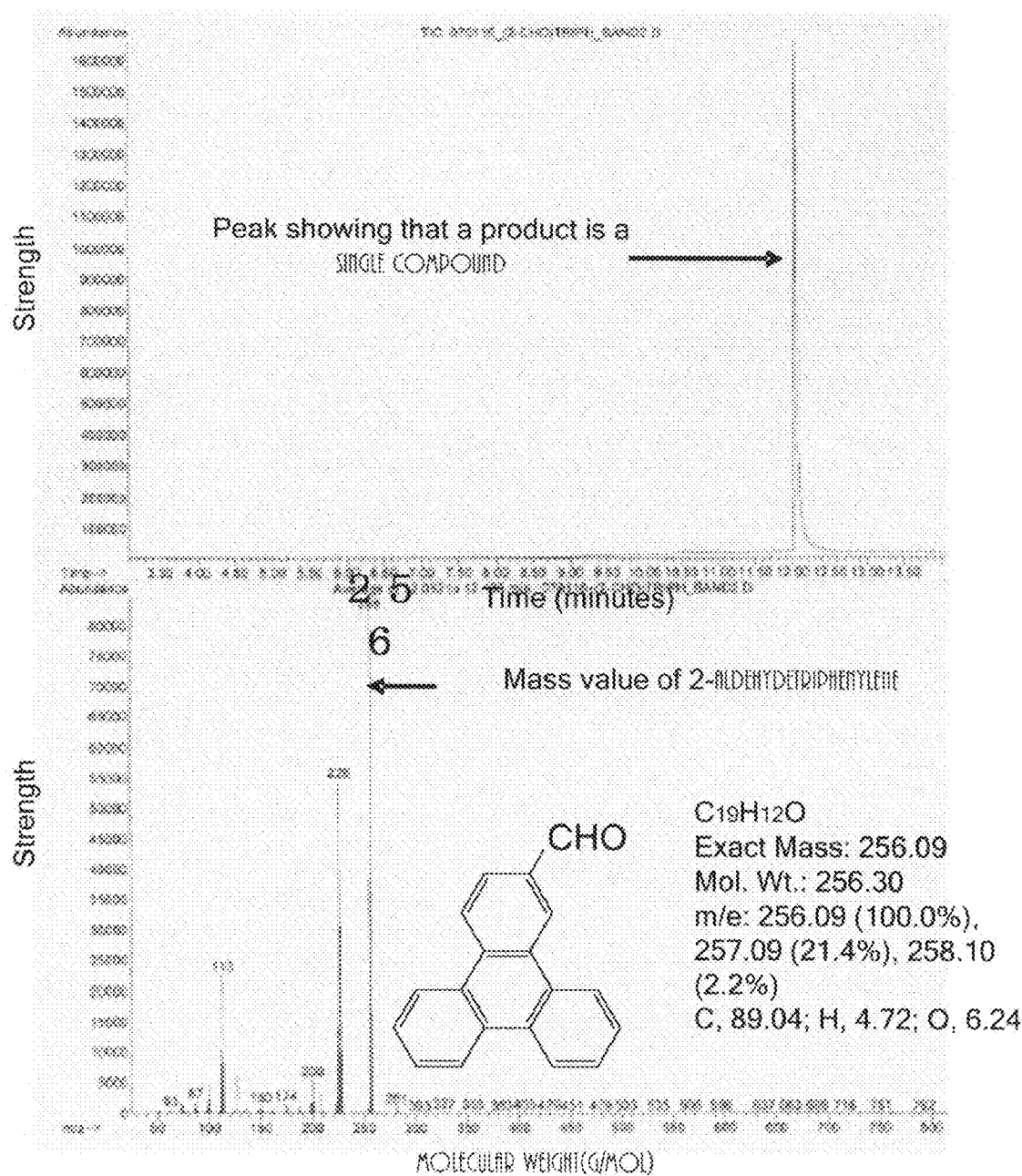
FIG. 18 is a view showing a GCMS measurement result of 2-formyltriphenylene.

The obtained orange colored powder was analyzed by means of $^1$HNMR and GCMS. The results are shown in FIGS. 17 and 18. As shown in FIG. 17, peaks derived from triphenylene and formyl group were assigned. As shown in FIG. 18, molecular weight equivalent to formyltriphenylene was also detected. Thereby, it was confirmed that 2-formyltriphenylene was obtained as a single compound.

(Production of Polymer Complex 15)

4 ml of nitrobenzene and 1 ml of methanol were placed in a test tube, and 6.3 mg (0.02 mmol) of 2,4,6-tris(4-pyridyl)-1,3,5-triazine (C) was dissolved therein, and 2-formyltriphenylene ($D_{15}$) was added thereto. Then, the solution obtained above was used as a bottom layer, and a solution of 9.6 mg (0.03 mmol) $ZnI_2$ in 1.0 ml of methanol was added quietly thereon, and left at about 23 to 25° C. (room temperature) for about 3 days to give a polymer complex 15 [$(ZnI_2)_3$ $(C)_2(1)_{15}$)] (yellow crystal).

(Analysis of Polymer Complex 15)

Figure 19:
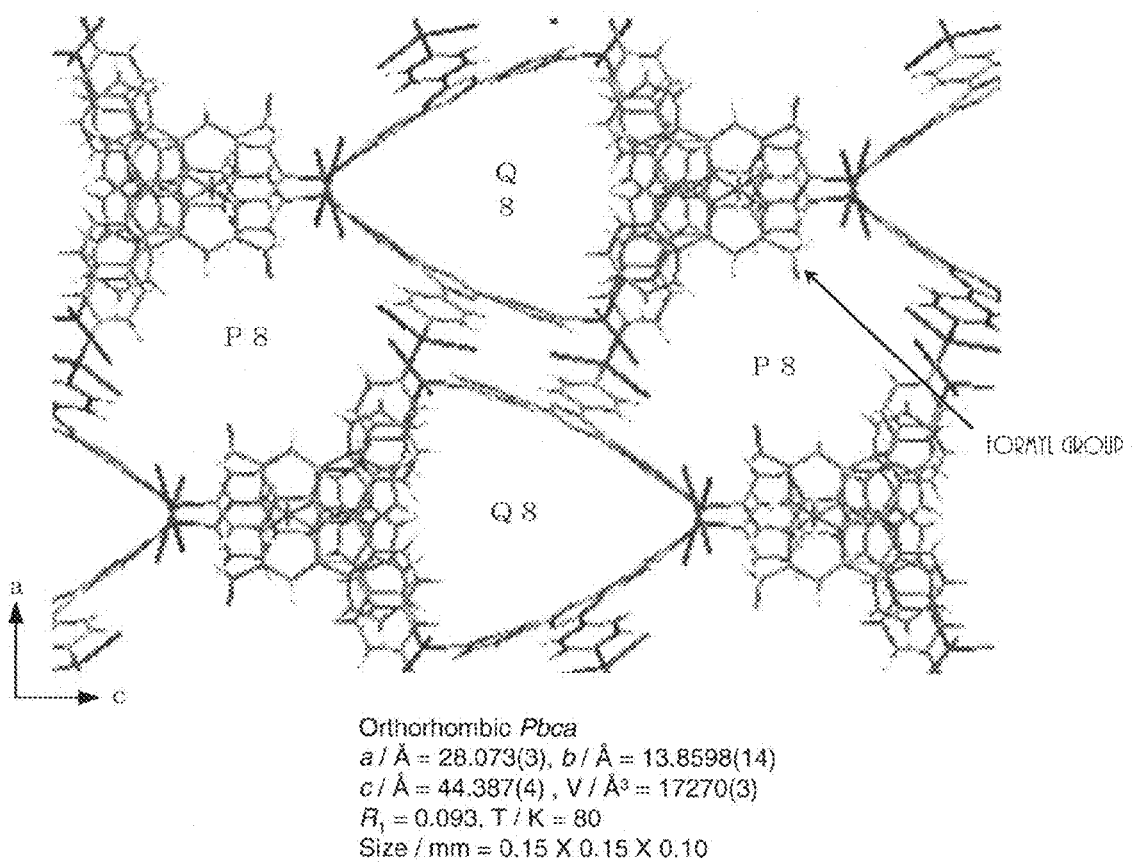
FIG. 19 is a view showing a crystal structure of the polymer complex 15.

The resulting polymer complex 15 (yellow crystal) was analyzed for its X-ray crystal structure by means of CCD X-ray analyzation equipment. The results are shown in FIG. 19. FIG. 19 with an axis b in a direction perpendicular to the plane of this figure (crystal 010 plane) shows an interpenetrated structure in the three-dimensional lattice-like structure of the polymer complex 15 along the direction (axis b) in which channels P8 and Q8 extend. In FIG. 19, guest molecules incorporated into channels P8 and Q8 are not shown.

The polymer complex 15 has two kinds of channels (P8 and Q8) each arranged regularly between stack structures of tris(4-pyridyl)triazine (C) and 2-formyltriphenylene ($D_{15}$) which are formed in a three-dimensional lattice-like structure constructed by tris(4-pyridyl)triazine (C) and zinc iodide.

The channel P8 is almost cylindrical and mainly surrounded by hydrogen atoms on the edge of the π-plane of infinitely stacked tris(4-pyridyl)triazine (C) and 2-formyltriphenylene ($D_{15}$). The formyl group of 2-formyltriphenylene ($D_{15}$) is oriented toward an inner surface of channel P8 to form a part of the inner surface of channel P8.

On the other hand, channel Q8 is in the form of a pseudo-triangular prism, where two of the three walls forming the triangular prism are surrounded by the π-plane of tris(4-pyridyl)triazine (C), and the third is surrounded by hydrogen atoms on the edge of the π-plane of infinitely stacked tris(4-pyridyl)triazine (C) and 2-formyltriphenylene ($D_{15}$). The formyl group of 2-formyltriphenylene ($D_{15}$) is not oriented toward an inner surface of channel Q8.

[Chemical Modification of Inner Surfaces of Channels of Polymer Complex 15]

The polymer complexes 15 synthesized as described above were respectively dipped in a solution having an amine compound (3-aminobenzoic acid or aniline) dissolved, thereby, 2-formyltriphenylene ($D_{15}$) and the amine compound caused a dehydration reaction in the single crystal of the polymer complex 15 to synthesize polymer complexes 16 and 17 having imine in the framework as shown below.

(Production of Polymer Complexes 16 and 17)

<Production of Polymer Complex 16>

By dipping the polymer complex 15 in an ethyl acetate solution of 0.11 M 3-aminobenzoic acid for four hours while heating at 60° C., 2-formyltriphenylene ($D_{15}$) constituting the polymer complex 15 and 3-aminobenzoic acid incorporated into channels as the guest molecule of the polymer complex 15 caused a dehydration reaction to give a polymer complex 16 [$(ZnI_2)_3(C)_2(D_{16})$] being a yellow crystal (see Formula 19 below).

<Production of Polymer Complex 17>

By dipping the polymer complex 15 in a cyclohexane solution of 0.11 M aniline for 24 hours while heating at 60° C., 2-formyltriphenylene ($D_{15}$) constituting the polymer complex 15 and aniline incorporated into channels as the guest molecule of the polymer complex 15 caused a dehydration reaction to give a polymer complex 17 [$(ZnI_2)_3(C)_2(D_{17})$] being an orange-colored crystal (see the following Formula 20).

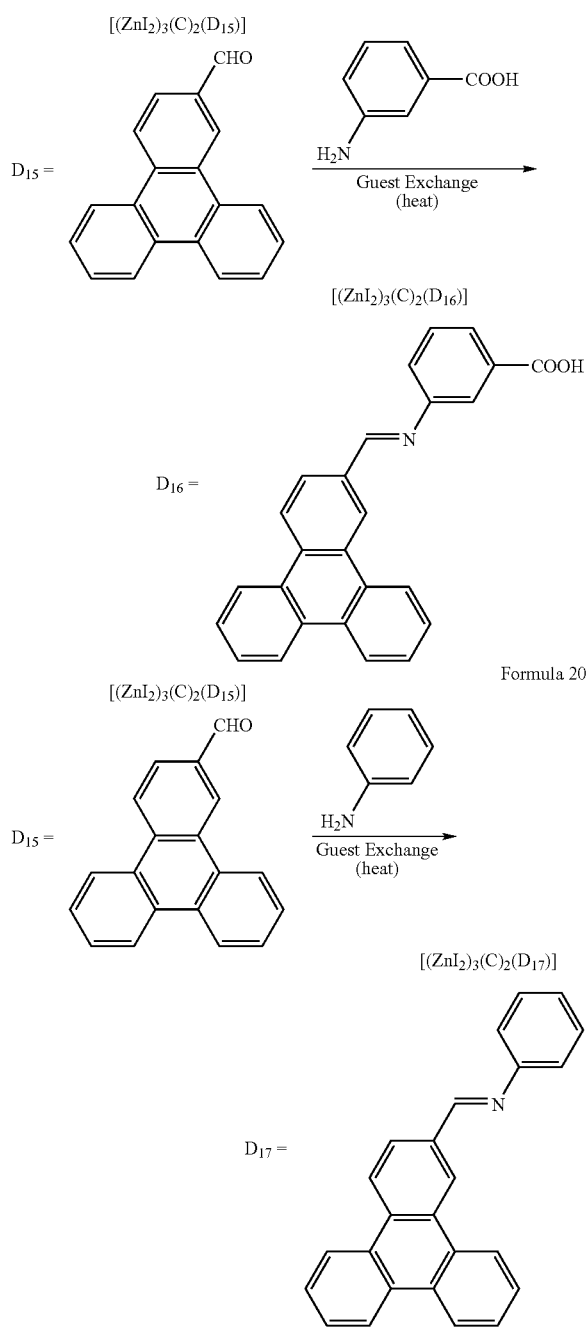

(Analysis of Polymer Complexes 16 and 17)

Figure 20:
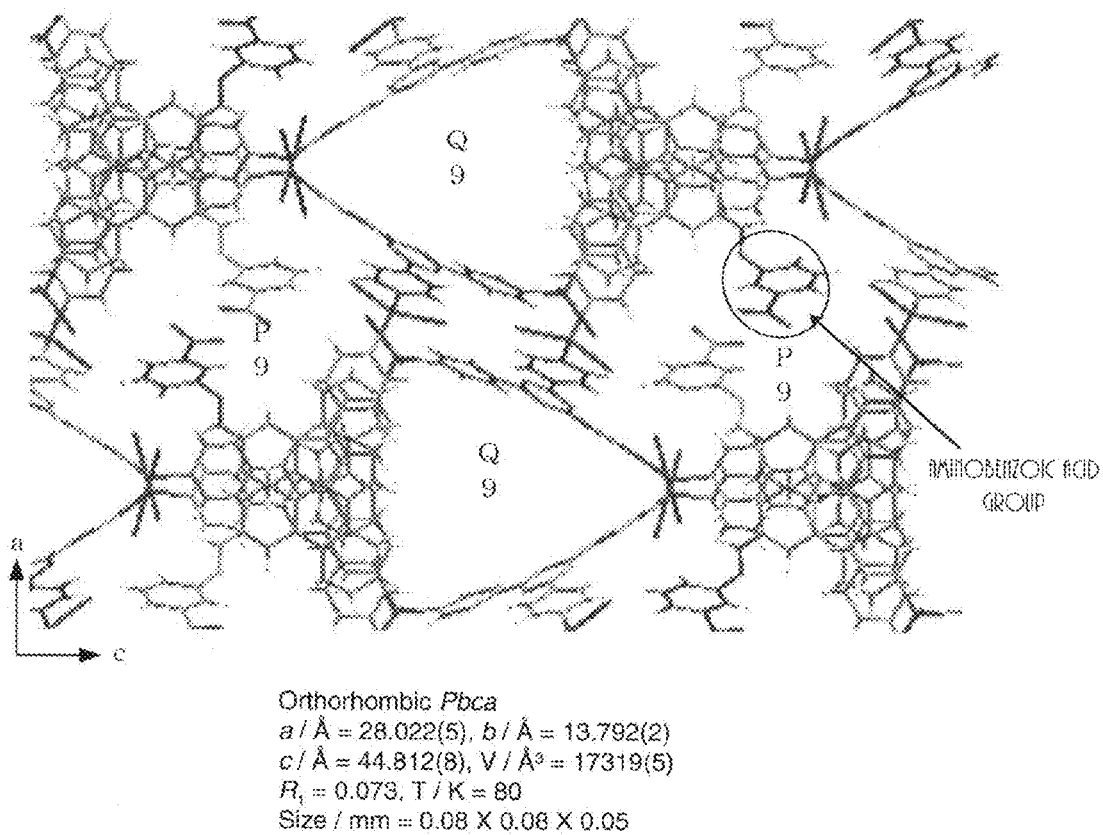
FIG. 20 is a view showing a crystal structure of the polymer complex 16.
Figure 21:
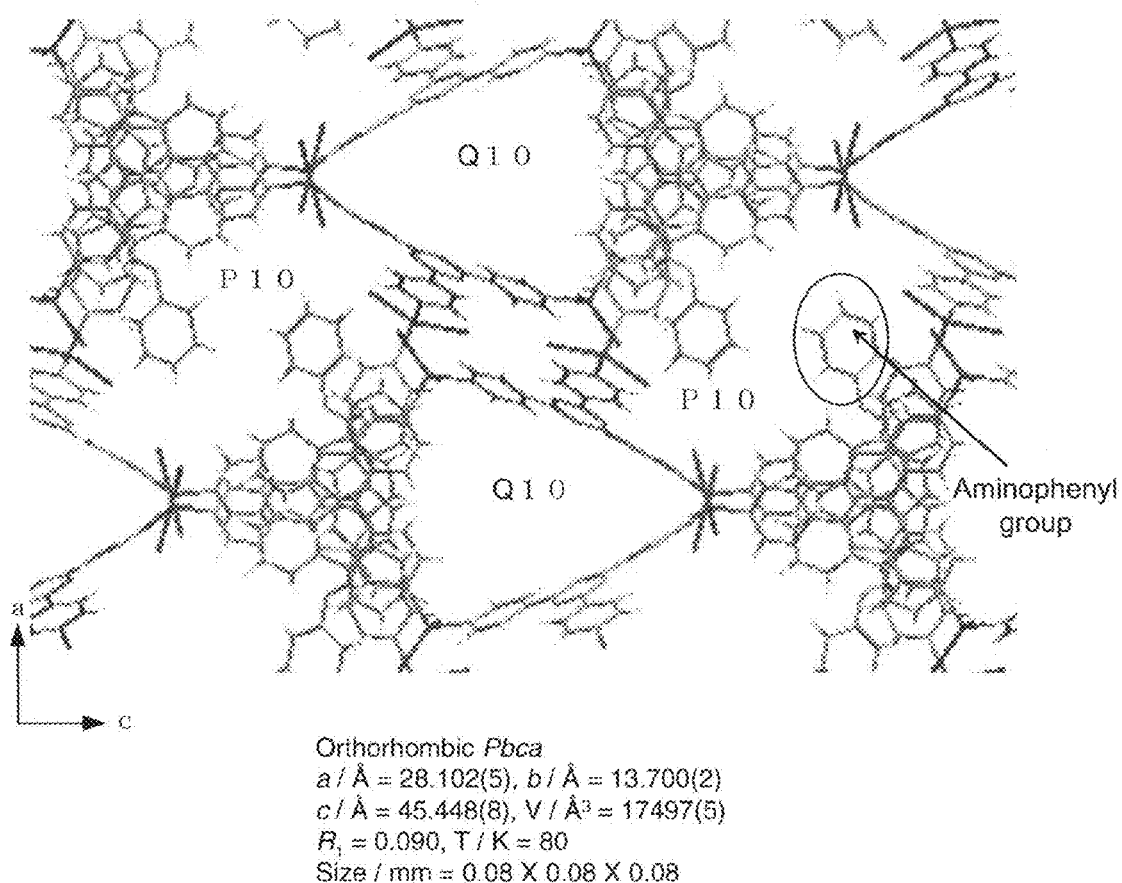
FIG. 21 is a view showing a crystal structure of the polymer complex 17.

The resulting polymer complex 16 (yellow crystal) and polymer complex 17 (orange-colored crystal) were analyzed for their X-ray crystal structures. FIGS. 20 and 21 with an axis b in a direction perpendicular to the plane of these figures (crystal 010 plane) show an interpenetrated structure in the three-dimensional lattice-like structure of the polymer complexes 16 and 17 along the direction (axis b) in which channels P9, P10, Q9, and Q10 extend. In FIGS. 20 and 21, guest molecules incorporated into each channel are not shown.

The polymer complexes 16 and 17 maintain the three-dimensional structure of the polymer complex 15 (see FIG. 19) and have a three-dimensional structure as shown in FIGS. 20 and 21. That is, the polymer complexes 16 and 17 have two kinds of channels (P9 and Q9 or P10 and Q10) each arranged regularly in a stack structure between tris(4-pyridyl)triazine (C) and an imine compound (2-iminomethyltriphenylene) ($D_{16}$, $D_{17}$) [polymer complex 16: 2-{(3-carboxyphenylimino)methyl}triphenylene ($D_{16}$); and polymer complex 17: 2-{(phenylimino)methyl}triphenylene ($D_{17}$)] which are formed in a three-dimensional lattice-like structure constructed by tris(4-pyridyl)triazine (C) and zinc iodide.

The channels P9 and P10 are almost cylindrical and mainly surrounded by hydrogen atoms on the edge of the π-plane of infinitely stacked tris(4-pyridyl)triazine (C) and 2-iminomethyltriphenylene ($D_{16}$, $D_{17}$). The imino group (3-carboxyphenyliminomethyl group, phenyliminomethyl group) of 2-iminomethyltriphenylene ($D_{16}$, $D_{17}$) is oriented toward an inner face of channels P9 and P10 to form a part of the inner face of channels P9 and P10.

On the other hand, channels Q9 and Q10 are in the form of a pseudo-triangular prism, where two of the three walls forming the triangular prism are surrounded by the π-plane of tris(4-pyridyl)triazine (C), and the third is surrounded by hydrogen atoms on the edge of the π-plane of infinitely stacked tris(4-pyridyl)triazine (C) and 2-iminomethyltriphenylene ($D_{16}$, $D_{17}$). The imino group of 2-iminomethyltriphenylene ($D_{16}$, $D_{17}$) is not oriented toward an inner face of channels Q9 and Q10.

The invention claimed is:

1. A method for chemically modifying inner surfaces of channels of at least one kind of channel group in a polymer complex provided with two or more kinds of channel groups each composed of channels identical with one another and having similar affinity to a guest molecule,
    wherein the polymer complex comprises an aromatic compound having two or more coordinating sites as a ligand, a metal ion as a central metal, and an uncoordinating aromatic compound, has a three-dimensional lattice-like structure containing a stack structure comprising the uncoordinating aromatic compound intercalated between aromatic compound ligands in a three-dimensional coordination network formed by coordinating the aromatic compound ligands to the central metal ion, and is provided with two or more kinds of the channel groups in the three-dimensional coordination network;
    wherein the aromatic compound ligands are aromatic compounds represented by the following formula (1);
    wherein the central metal is at least one selected from zinc, copper, nickel, cobalt, iron and silver;
    wherein the uncoordinating aromatic compounds have, at one or more positions on the aromatic ring of aromatic compounds selected from the following formulae 5(a) to 5(i), the position or positions being the same between the uncoordinating aromatic compounds forming the stack structure, substituents A of at least one kind selected from —$CH_2$—OH, —$CH_2CH_2$—OH, —OH, —$CH_2$—$NH_2$, —$CH_2CH_2$—$NH_2$, —$NH_2$, —$CH_2$—$NO_2$, —$CH_2CH_2$—$NO_2$, —$NO_2$, —$CH_2$—$CH_3$, —$CH_2CH_2$—$CH_3$, —$CH_3$, —$CH_2CH_2$—$OCOCH_3$, —$CH_2CH_2$—$OCOCH_3$, —$OCOCH_3$, —O—$CH_3$, —O—$CH_2CH_3$, —S—$CH_3$, —S—$CH_2CH_3$, —O—$CH_2CH_2$—OH, —$CH_2$—CHO, —$CH_2CH_2$—CHO, and —CHO, the substituents A being the same between the uncoordinating aromatic compounds forming the stack structure and the substituents A are arranged regularly such that the substituents A are directed to the inside of a specific channel group B out of the two or more kinds of channel groups; and wherein the method comprising the steps of: including the guest molecule in the channel of the channel group B in which the substituents A are arranged; and reacting the guest molecule with the substituent A in the channel to convert the substituent A to a substituent A', and to arrange the substituent A' regularly directing to the inside of the channel of the channel group B or any channel of other channel groups;

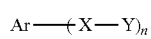

Formula 1 wherein Ar is a structure having an aromatic ring; X is a divalent organic group or a single bond through which Ar and Y are directly bound to each other; Y is a coordinating atom or a coordinating atom-containing atomic group; n is a number of 3 to 6; and a plurality of Xs contained in one molecule may be different from one another, and a plurality of Ys may be different from one another Formula 5

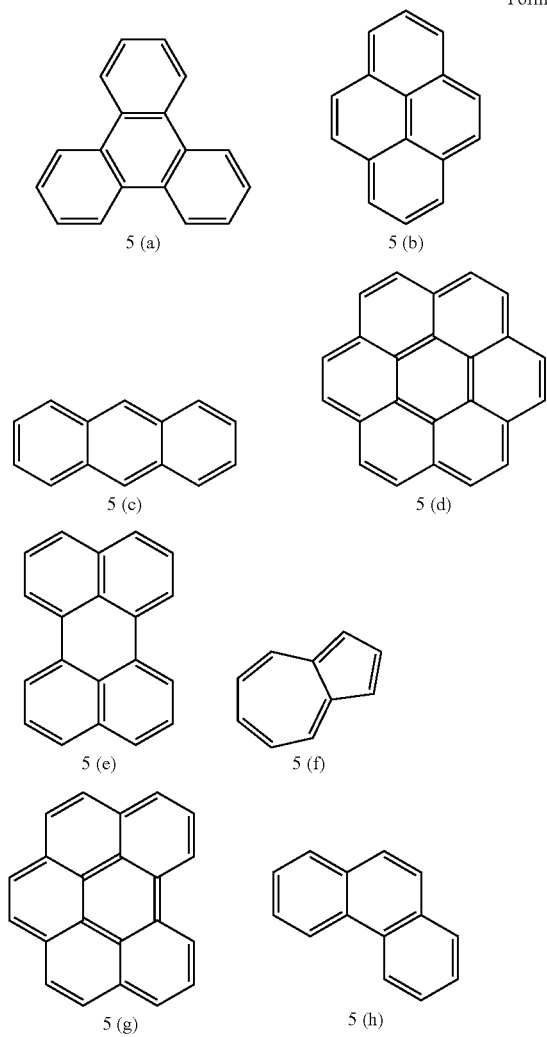

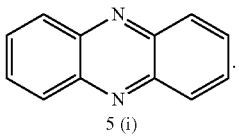

5 (i)

2. The method for chemically modifying channels according to claim 1, wherein the polymer complex can selectively incorporate, release and/or transport guest molecules.

3. The method for chemically modifying channels according to claim 1, wherein, in the polymer complex, the three-dimensional coordination network is a complexed three-dimensional coordination network comprising two or more independent three-dimensional coordination networks complexed with one another.

4. The method for chemically modifying channels according to claim 3, wherein, in the polymer complex, the complexed three-dimensional coordination network is an interpenetrated structure.

5. The method for chemically modifying channels according to claim 1, wherein two channel groups selected arbitrarily from the two or more kinds of channel groups in the polymer complex are different from each other in at least one factor selected from the size of a channel, the shape of a channel and the ratio of a region over which the π-plane of the aromatic compound ligands and/or uncoordinating aromatic compounds is exposed to an inner face of the wall, to a region over which hydrogen atoms of the aromatic compound are exposed to the inner face of the wall in a channel in comparison therebetween.

6. The method for chemically modifying channels according to claim 1, wherein, in the polymer complex, a channel contained in a channel group selected from the two or more kinds of channel groups is in a long and thin channel form.

7. The method for chemically modifying channels according to claim 1, wherein, in the polymer complex, the aromatic compound represented by the formula (1) as the aromatic compound ligand is tris(4-pyridyl)triazine, and the condensed polycyclic aromatic compound as the uncoordinating aromatic compound is at least one member selected from triphenylene and perylene.

8. The method for chemically modifying channels according to claim 1, wherein, in the polymer complex, the substituent A can exhibit an intramolecular interaction higher than van der Waals' force.

9. The method for chemically modifying channels according to claim 1, wherein the HOMO (highest occupied molecular orbital) of the uncoordinating aromatic compound and the LUMO (lowest unoccupied molecular orbital) of the aromatic compound ligand have an overlapping of orbital shape in the stack structure in the three-dimensional coordination network in the polymer complex, thereby stabilizing the stack structure.

10. The method for chemically modifying channels according to claim 1, wherein, in the polymer complex, at least one of the substituents A is $-NH_2$.

11. The method for chemically modifying channels according to claim 10, wherein $-NH_2$ being the substituent A is converted to $-N=Q1$, Q1 representing a divalent organic group.

12. The method for chemically modifying channels according to claim 11, wherein the guest molecule is an aldehyde compound, and incorporation of the aldehyde compound by the channel of the channel group B can cause a dehydration reaction of $-NH_2$ being the substituent A with the aldehyde compound to convert the —NH₂ to —N=Q1, Q1 representing a divalent organic group.

13. The method for chemically modifying channels according to claim 10, wherein —NH₂ being the substituent A is converted to —NHC(=O)-Q2, Q2 representing a monovalent organic group.

14. The method for chemically modifying channels according to claim 13, wherein the guest molecule is acid anhydride or isocyanato, and incorporation of the acid anhydride or the isocyanato by the channel of the channel group B can cause a reaction of —NH₂ being the substituent A with the acid anhydride or the isocyanato to convert the —NH₂ to —NHC(=O)-Q2, Q2 representing a monovalent organic group.

15. The method for chemically modifying channels according to claim 1, wherein at least one of the substituents A is —CHO and the guest molecule is an amino compound, incorporation of the amino compound by the channel of the channel group B can cause a dehydration reaction of the —CHO with the amino compound to convert the —CHO to —CHN-Q3, Q3 representing a monovalent organic group.

16. The method for chemically modifying channels according to claim 1, wherein at least one of the substituents A is converted to -Q4-COON, Q4 representing a divalent organic group in the polymer complex.

17. A polymer complex comprising an aromatic compound having two or more coordinating sites as a ligand, a metal ion as a central metal, and an uncoordinating aromatic compound,
   wherein the polymer complex has a three-dimensional lattice-like structure containing a stack structure comprising the uncoordinating aromatic compound intercalated between aromatic compound ligands in a three-dimensional coordination network formed by coordinating the aromatic compound ligands to the central metal ion, and is provided with two or more kinds of channel groups each composed of channels identical with one another and having similar affinity to a guest molecule in the three-dimensional coordination network;
   wherein the aromatic compound ligands are aromatic compounds represented by the following formula (1);
   wherein the central metal is at least one selected from zinc, copper, nickel, cobalt, iron and silver;
   wherein the uncoordinating aromatic compounds have groups A'i represented by —N=Q1, Q1 representing a divalent organic group, at one or more positions on the aromatic ring of aromatic compounds selected from the following formulae 5(a) to 5(i), the position or positions being the same between the uncoordinating aromatic compounds forming the stack structure, and are arranged regularly such that the groups A'i are directed to the inside of a specific channel group B' out of the two or more kinds of channel groups;

Ar—(X—Y)ₙ  Formula 1 wherein Ar is a structure having an aromatic ring; X is a divalent organic group or a single bond through which Ar and Y are directly bound to each other; Y is a coordinating atom or a coordinating atom-containing atomic group; n is a number of 3 to 6; and a plurality of Xs contained in one molecule may be different from one another, and a plurality of Ys may be different from one another

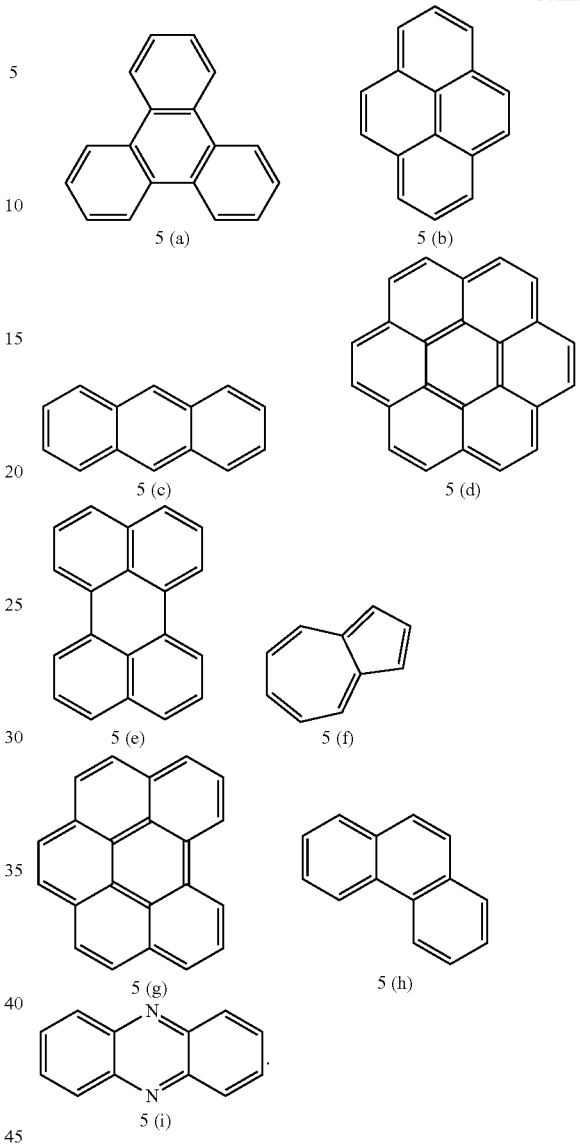

Formula 5

5(a)   5(b)

5(c)   5(d)

5(e)   5(f)

5(g)   5(h)

5(i)

18. A polymer complex comprising an aromatic compound having two or more coordinating sites as a ligand, a metal ion as a central metal, and an uncoordinating aromatic compound,
   wherein the polymer complex has a three-dimensional lattice-like structure containing a stack structure comprising the uncoordinating aromatic compound intercalated between aromatic compound ligands in a three-dimensional coordination network formed by coordinating the aromatic compound ligands to the central metal ion, and is provided with two or more kinds of channel groups each composed of channels identical with one another and having similar affinity to a guest molecule in the three dimensional coordination network;
   wherein the aromatic compound ligands are aromatic compounds represented by the following formula (1);
   wherein the central metal is at least one selected from zinc, copper, nickel, cobalt, iron and silver;
   wherein the uncoordinating aromatic compounds have groups A'a represented by —NHC(=O)-Q2, Q2 representing a monovalent organic group, at one or more positions on the aromatic ring of aromatic compounds selected from the following formulae 5(a) to 5(i), the position or positions being the same between the uncoordinating aromatic compounds forming the stack structure, and are arranged regularly such that the groups A'a are directed to the inside of a specific channel group B' out of the two or more kinds of channel groups;

$$Ar\text{---}(X\text{---}Y)_n \qquad \text{Formula 1}$$

wherein Ar is a structure having an aromatic ring; X is a divalent organic group or a single bond through which Ar and Y are directly bound to each other; Y is a coordinating atom or a coordinating atom-containing atomic group; n is a number of 3 to 6; and a plurality of Xs contained in one molecule may be different from one another, and a plurality of Ys may be different from one another Formula 5

5 (a)  5 (b)  5 (c)  5 (d)  5 (e)  5 (f)  5 (g)  5 (h)  5 (i)

19. A polymer complex comprising an aromatic compound having two or more coordinating sites as a ligand, a metal ion as a central metal, and an uncoordinating aromatic compound, wherein the polymer complex has a three-dimensional lattice-like structure containing a stack structure comprising the uncoordinating aromatic compound intercalated between aromatic compound ligands in a three-dimensional coordination network formed by coordinating the aromatic compound ligands to the central metal ion, and is provided with two or more kinds of channel groups each composed of channels identical with one another and having similar affinity to a guest molecule in the three-dimensional coordination network;

wherein the aromatic compound ligands are aromatic compounds represented by the following formula (1);

wherein the central metal is at least one selected from zinc, copper, nickel, cobalt, iron and silver;

wherein the uncoordinating aromatic compounds have groups A'im represented by —CHN-Q3, Q3 representing a monovalent organic group, at one or more positions on the aromatic ring of aromatic compounds selected from the following formulae 5(a) to 5(i), the position or positions being the same between the uncoordinating aromatic compounds forming the stack structure, and are arranged regularly such that the groups A'im are directed to the inside of a specific channel group B' out of the two or more kinds of channel groups;

$$Ar\text{---}(X\text{---}Y)_n \qquad \text{Formula 1}$$

wherein Ar is a structure having an aromatic ring; X is a divalent organic group or a single bond through which Ar and Y are directly bound to each other; Y is a coordinating atom or a coordinating atom-containing atomic group; n is a number of 3 to 6; and a plurality of Xs contained in one molecule may be different from one another, and a plurality of Ys may be different from one another Formula 5

5 (a)  5 (b)  5 (c)  5 (d)

-continued

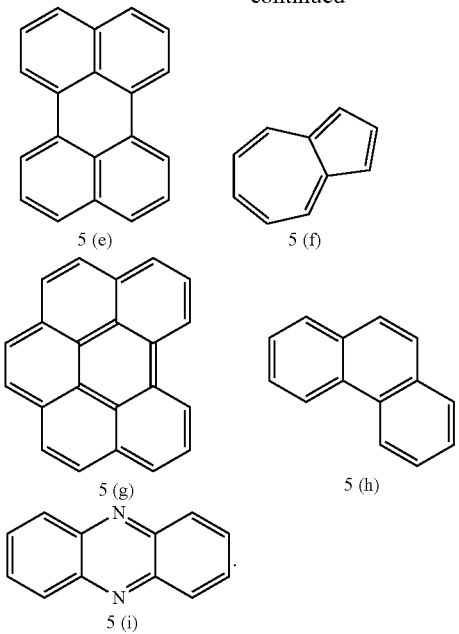

5 (e)
5 (f)
5 (g)
5 (h)
5 (i)

20. A polymer complex comprising an aromatic compound having two or more coordinating sites as a ligand, a metal ion as a central metal, and an uncoordinating aromatic compound,
   wherein the polymer complex has a three-dimensional lattice-like structure containing a stack structure comprising the uncoordinating aromatic compound intercalated between aromatic compound ligands in a three-dimensional coordination network formed by coordinating the aromatic compound ligands to the central metal ion, and is provided with two or more kinds of channel groups each composed of channels identical with one another and having similar affinity to a guest molecule in the three-dimensional coordination network;
   wherein the aromatic compound ligands are aromatic compounds represented by the following formula (1);
   wherein the central metal is at least one selected from zinc, copper, nickel, cobalt, iron and silver;
   wherein the uncoordinating aromatic compounds have groups A'c represented by -Q4-COOH, Q4 representing a divalent organic group, at one or more positions on the aromatic ring of aromatic compounds selected from the following formulae 5(a) to 5(i), the position or positions being the same between the uncoordinating aromatic compounds forming the stack structure, and are arranged regularly such that the groups A'c are directed to the inside of a specific channel group B' out of the two or more kinds of channel groups;

$$Ar-(X-Y)_n$$ Formula 1 wherein Ar is a structure having an aromatic ring; X is a divalent organic group or a single bond through which Ar and Y are directly bound to each other; Y is a coordinating atom or a coordinating atom-containing atomic group; n is a number of 3 to 6; and a plurality of Xs contained in one molecule may be different from one another, and a plurality of Ys may be different from one another Formula 5

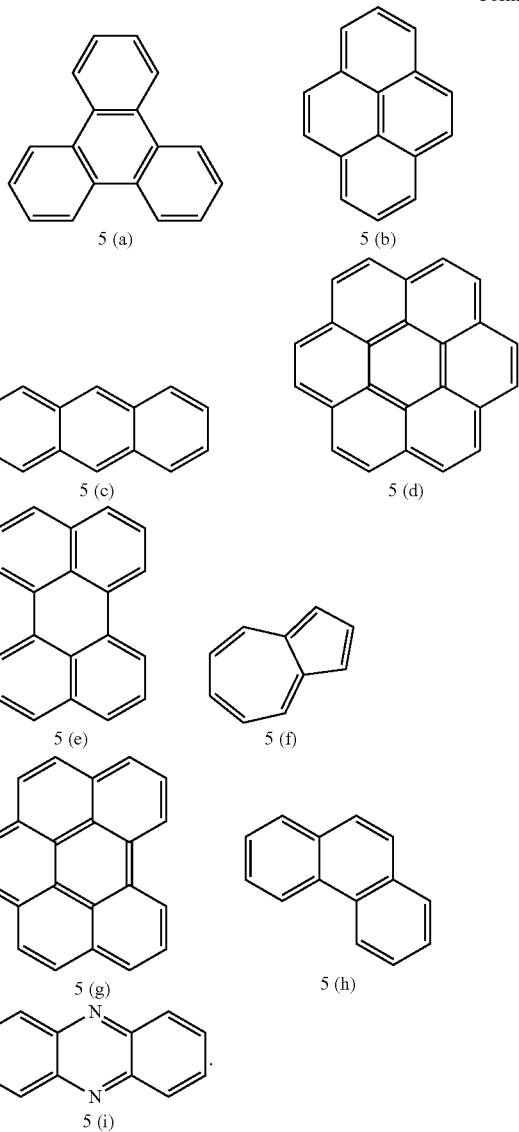

5 (a)
5 (b)
5 (c)
5 (d)
5 (e)
5 (f)
5 (g)
5 (h)
5 (i)

* * * * *